(12) United States Patent
Liu et al.

(10) Patent No.: US 11,851,455 B2
(45) Date of Patent: Dec. 26, 2023

(54) ACIDIC DYSTROGLYCAN OLIGOSACCHARIDE COMPOUND AND METHOD FOR MAKING SAME

(71) Applicant: UNIVERSITY OF PITTSBURGH - OF THE COMMONWEALTH SYSTEM OF HIGHER EDUCATION, Pittsburgh, PA (US)

(72) Inventors: Xinyu Liu, Wexford, PA (US); Aniruddha Sasmal, San Diego, CA (US)

(73) Assignee: University of Pittsburgh Of The Commonwealth System of Higher Education, Pittsburgh, PA (US)

( * ) Notice: Subject to any disclaimer, the term of this patent is extended or adjusted under 35 U.S.C. 154(b) by 287 days.

(21) Appl. No.: 16/960,271

(22) PCT Filed: Jan. 7, 2019

(86) PCT No.: PCT/US2019/012577
§ 371 (c)(1),
(2) Date: Dec. 10, 2020

(87) PCT Pub. No.: WO2019/136399
PCT Pub. Date: Jul. 11, 2019

(65) Prior Publication Data
US 2022/0081463 A1 Mar. 17, 2022

Related U.S. Application Data

(60) Provisional application No. 62/614,173, filed on Jan. 5, 2018.

(51) Int. Cl.
*C07H 15/04* (2006.01)
(52) U.S. Cl.
CPC .................................. *C07H 15/04* (2013.01)
(58) Field of Classification Search
None
See application file for complete search history.

(56) References Cited

U.S. PATENT DOCUMENTS 8,119,766 B2   2/2012   Campbell et al.

OTHER PUBLICATIONS

Inamori et al., Science, 2012, 335(6064), pp. 93-96. (Year: 2012).*
Form PCT/ISA/220, PCT Notification of Transmittal of the International Search Report and the Written Opinion of the International Searching Authority, or the Declaration, PCT/US2019/012577, dated Mar. 25, 2019.
Form PCT/ISA/210, PCT International Search Report for International Application No. PCT/US2019/012577, dated Mar. 25, 2019.
Form PCT/ISA/237, PCT Written Opinion of the International Searching Authority for International Application No. PCT/US2019/012577, dated Mar. 25, 2019.
Form PCT/IB/326, PCT Notification Concerning Transmittal of International Preliminary Report on Patentability, PCT/US2019/012577, dated Jul. 16, 2020.
Form PCT/IB/373, PCT International Preliminary Report on Patentability for International Application No. PCT/US2019/012577, dated Jul. 16, 2020.
Sasmal, Aniruddha, Development of Catalytic Glycosylation Method for Oligosaccharide Assembly and Total Synthesis of Acidic α-Dystroglycan Oligosaccharides, University of Pittsburgh, Ph.D. Dissertation, Mar. 31, 2017, See Summary, pp. 82, 97, 110-114, 122-124.
Praissman, Jeremy L., et al, B4GAT1 is the priming enzyme for the LARGE-dependent functional glycosylation of α-dystroglycan, eLife, vol. 3, Oct. 3, 2014, entire document.
Briggs, David C., et al, Structural basis of laminin binding to the LARGE glycans on dystroglycan, Nature Chemical Biology, vol. 12, Oct. 1, 2016, pp. 810-814.

* cited by examiner

*Primary Examiner* — Traviss C McIntosh, III
(74) *Attorney, Agent, or Firm* — Paul D. Bangor, Jr., Esquire; Clark Hill PLC

(57) ABSTRACT

A synthetic dystroglycan oligosaccharide comprising:

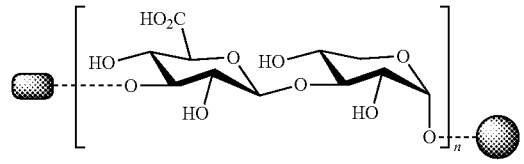

wherein a repeating disaccharide motif consists of Glucuronic Acid (ClcA) and Xylose (Xyl) having a defined glycosyl connection GlcA-β-(1→3)-Xyl-α-(1→3)-GlcA; wherein either end of the synthetic dystroglycan oligosaccharide is conjugatable with chemical or biological vehicle or support; wherein the non-reducing terminal (shown as ▨)

is conjugatable win any oligosaccharides or groups that can modify a hydroxyl functionality; and wherein the reducing terminal is conjugatable with any tags, oligosaccharides or anything that can modify a hydroxyl functionality.

5 Claims, 10 Drawing Sheets

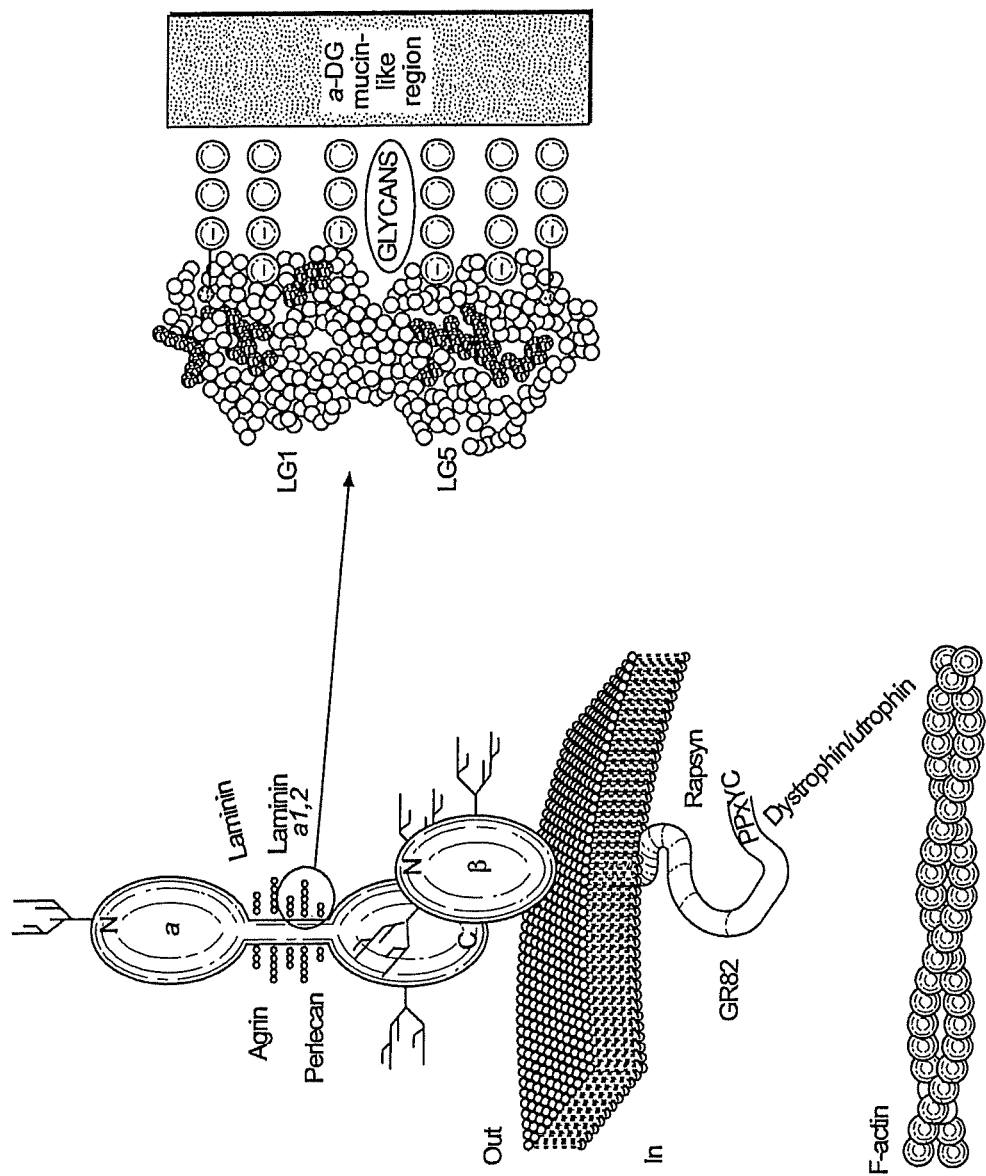
FIG. 1 Dystrophin-glycoprotein complex

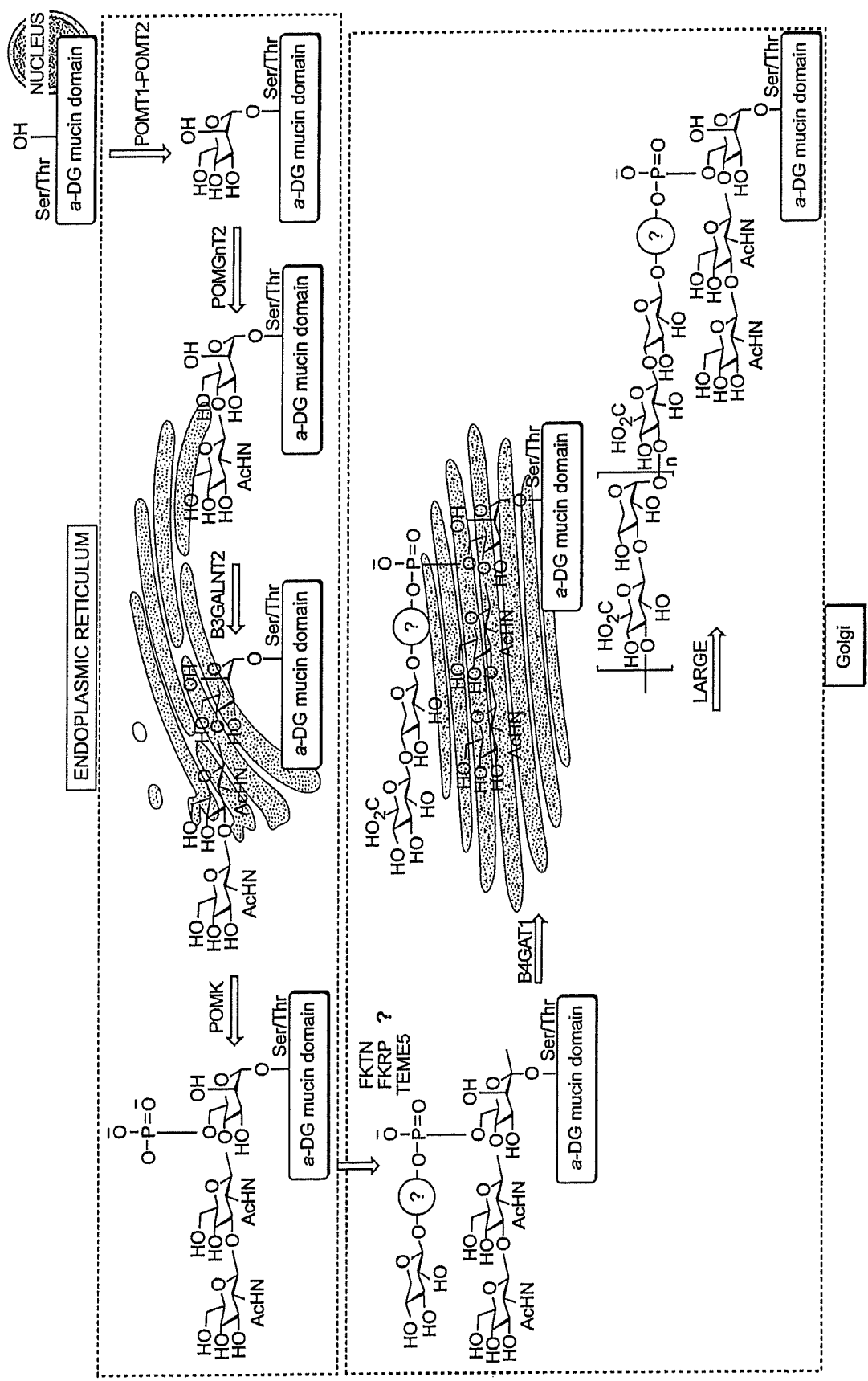
FIG. 2 Glycosylation of α-dystroglycan and localization of glycosyltransferases involved in the o-glycosylation pathway

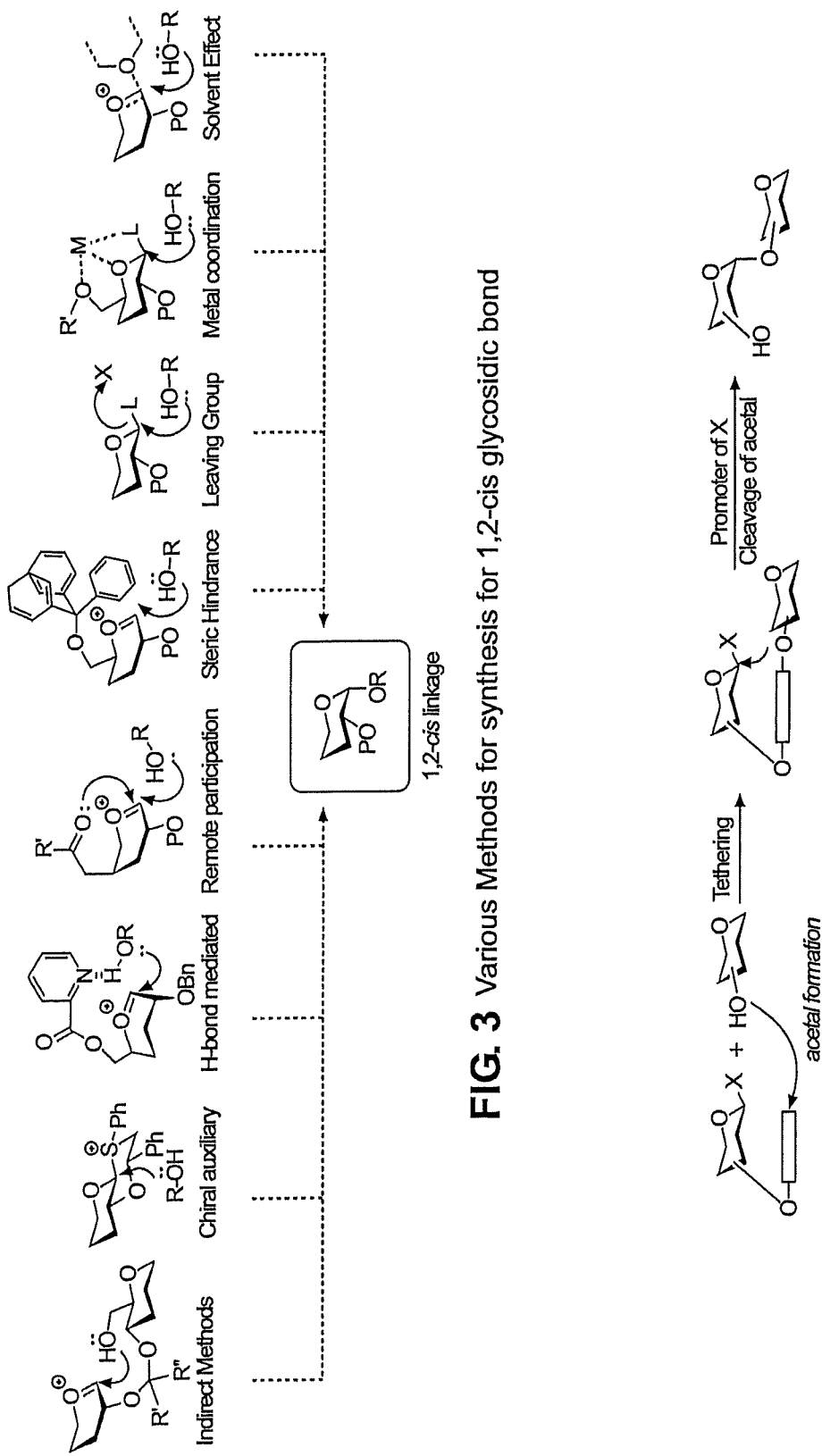
FIG. 3 Various Methods for synthesis for 1,2-cis glycosidic bond
FIG. 4 Intramolecular Aglycon Delivery

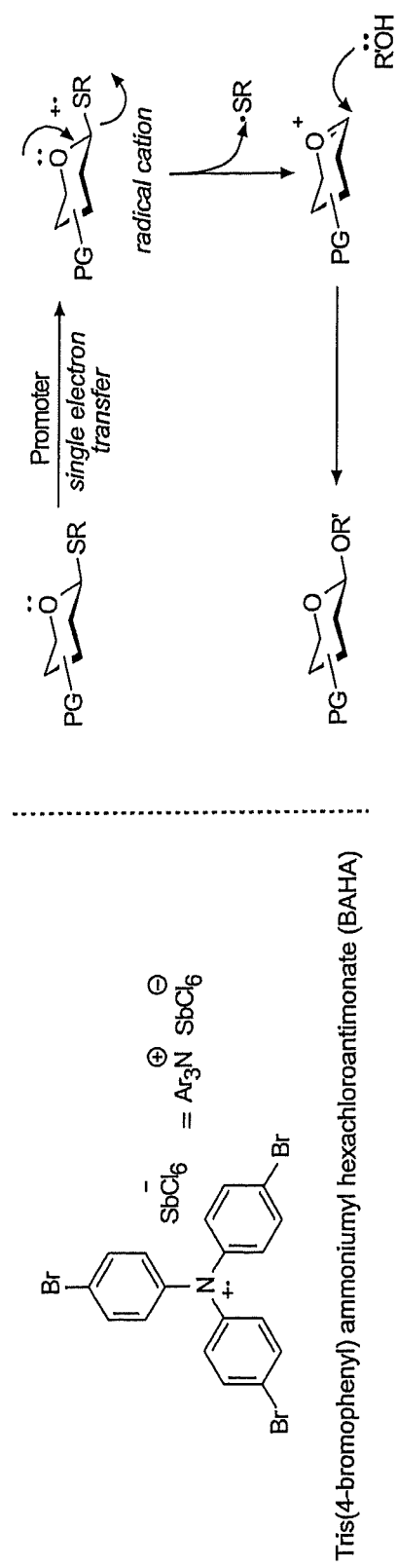
FIG. 5 Oxidative activation of thioglycoside
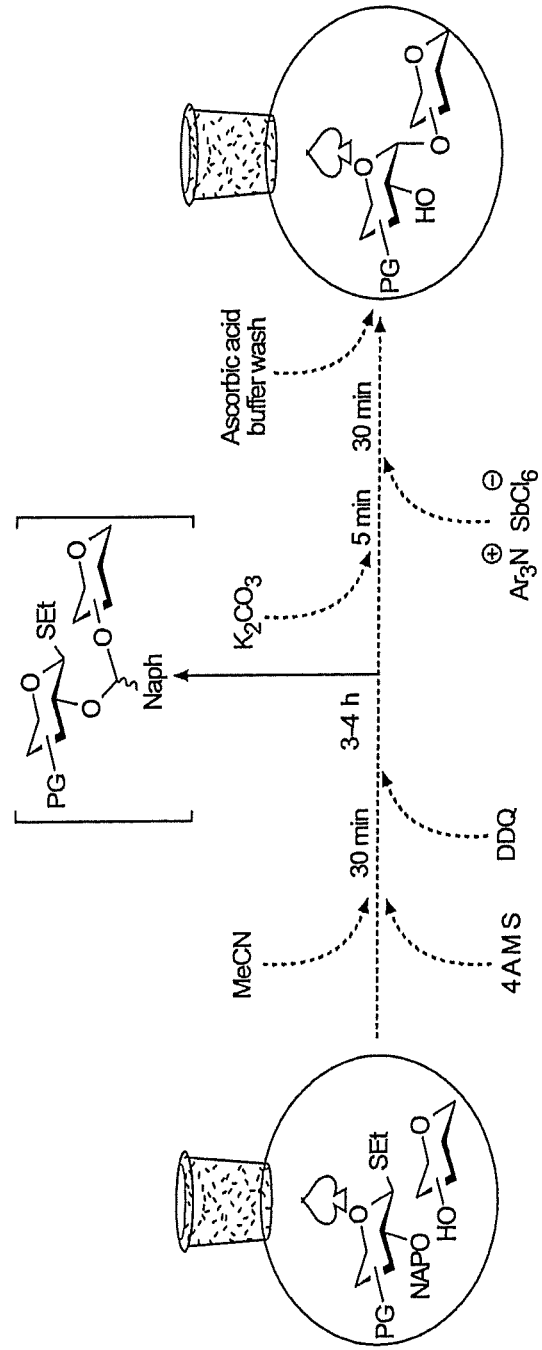
FIG. 6 NAP-mediated rapid one-pot IAD

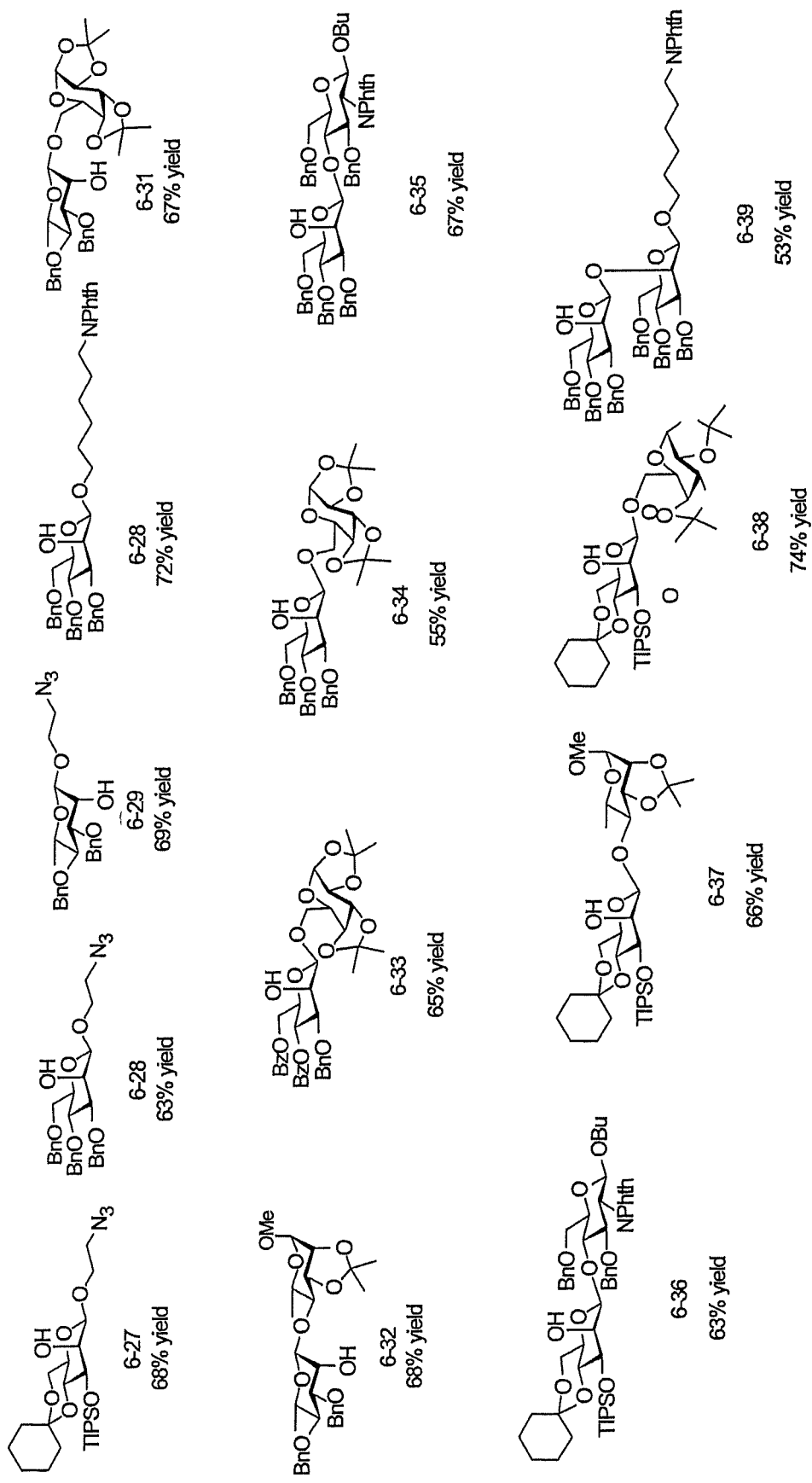
FIG. 7 1,2-cis disaccharide and disaccharide-linker sythesized via one-pot IAD

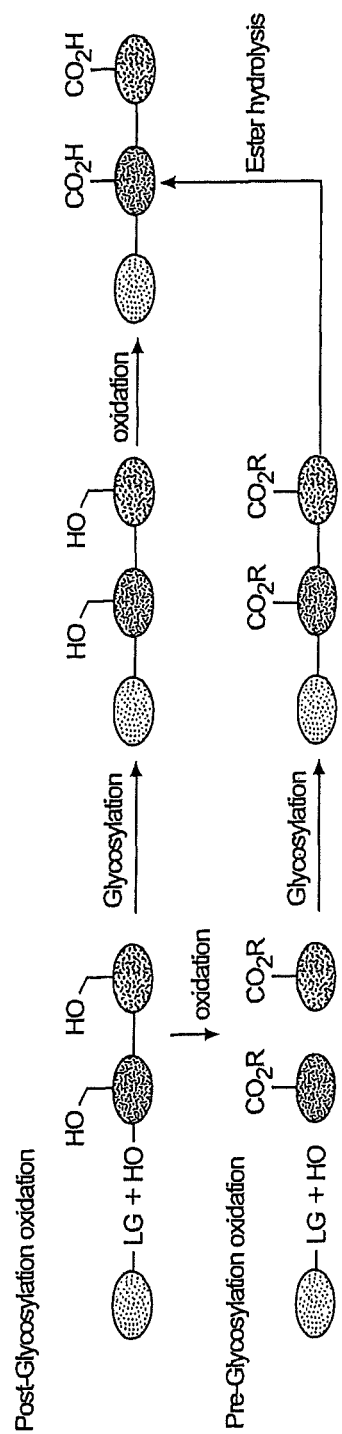
FIG. 8 Pre- and post- glycosylation to install uronic acid in oligosaccharide

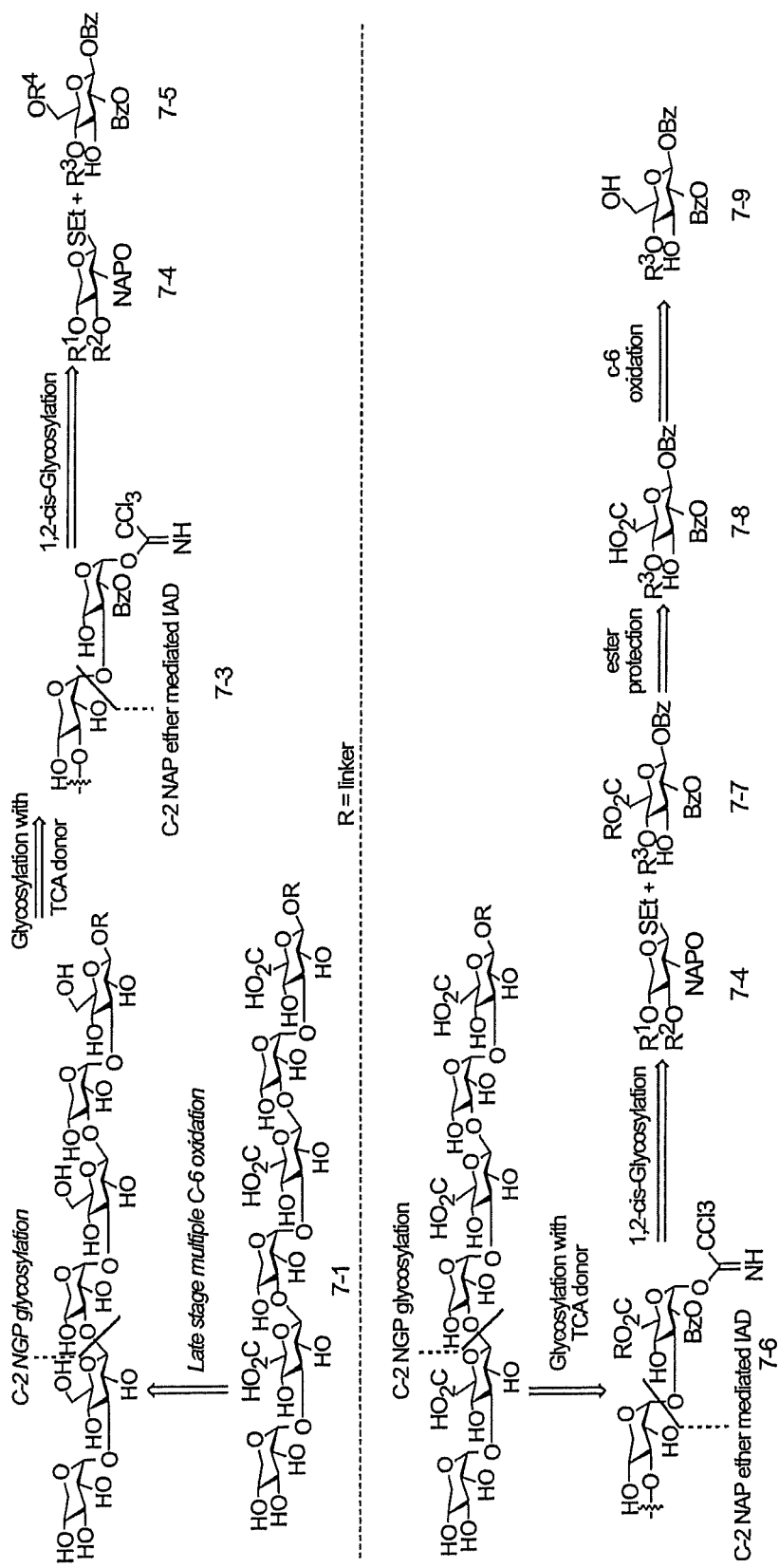
FIG. 9 Retrosynthetic approach towards LARGE glycan.
a) Post-glycosylation oxidation strategy,
b) Pre-glycosylation oxidation strategy.

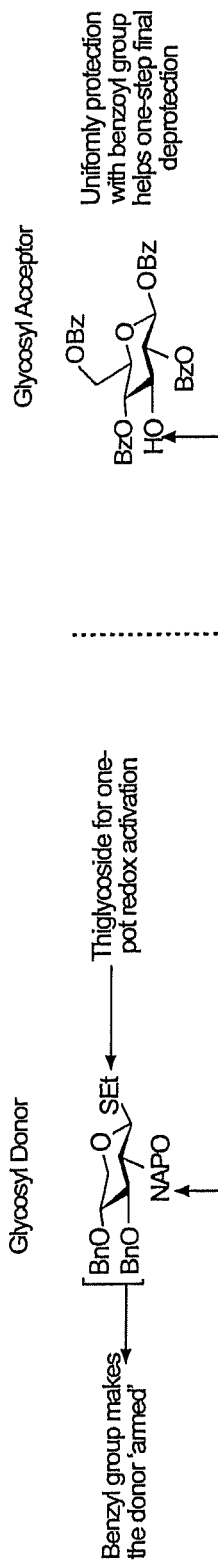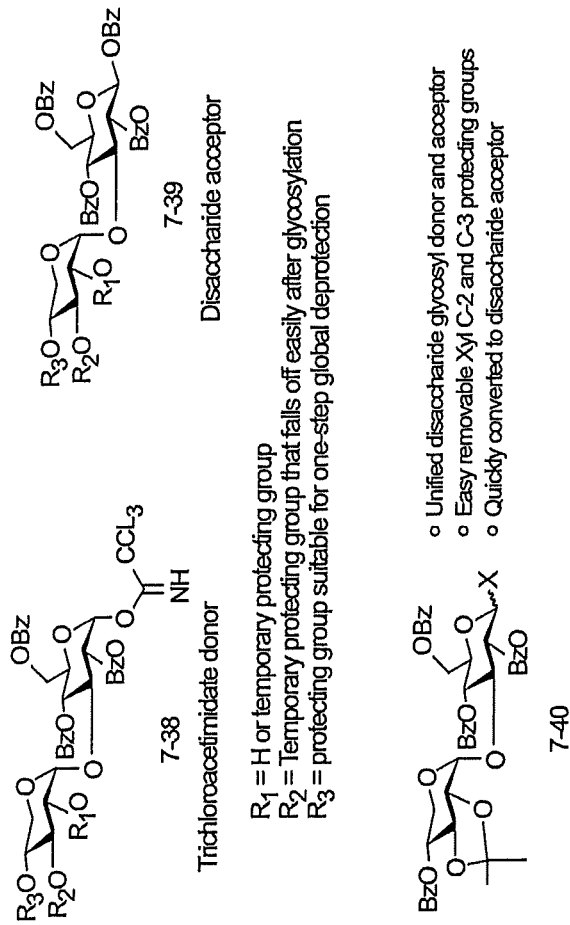
FIG. 10 Donor and acceptor by design for post-glycosylation oxidation strategy
FIG. 11 Synthesis of modified disaccharide for unified donor-acceptor strategy

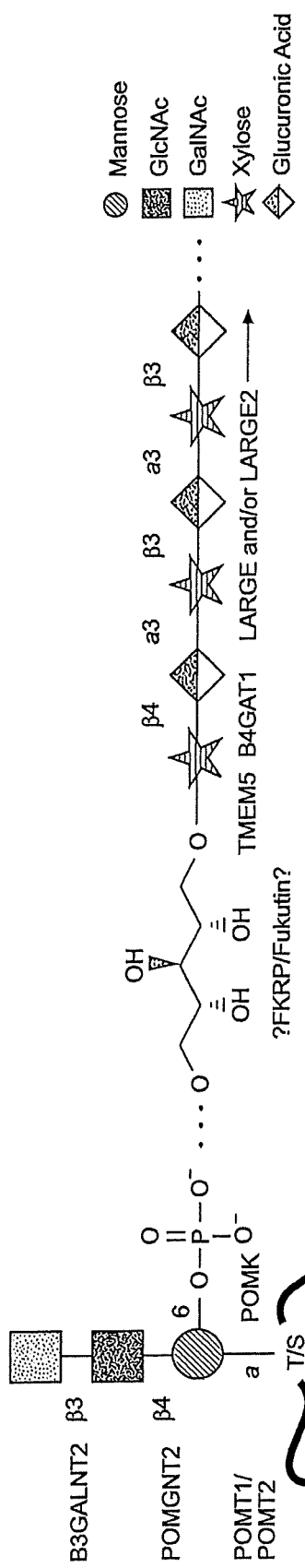
FIG. 12 Glysosyl modification of α-DG core with B4GAT1 and LARGE enzymes
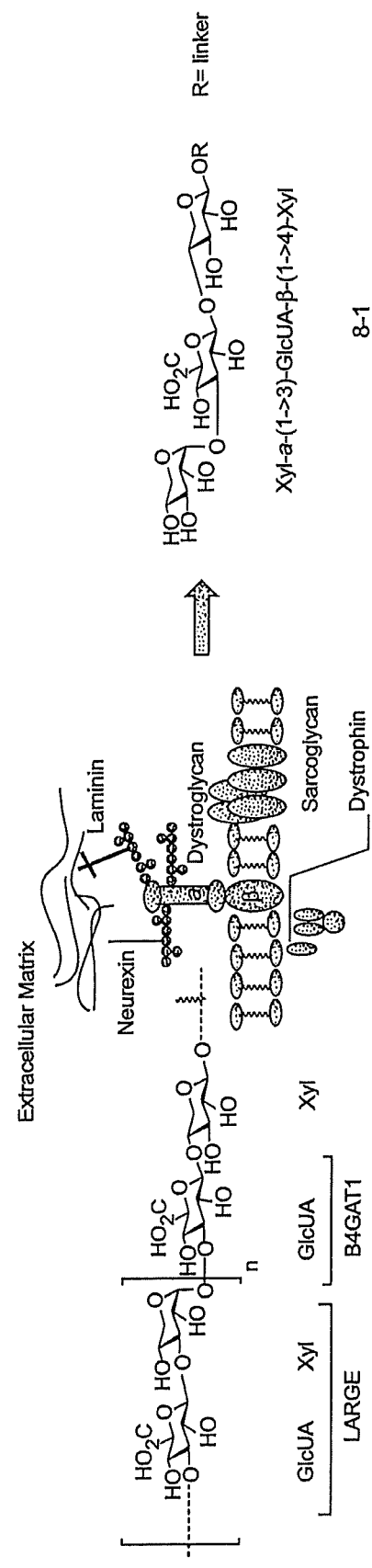
FIG. 13 Xyl-α-(1→3)-GlcA-β-(1→4)-Xyl as target trisaccharide motif

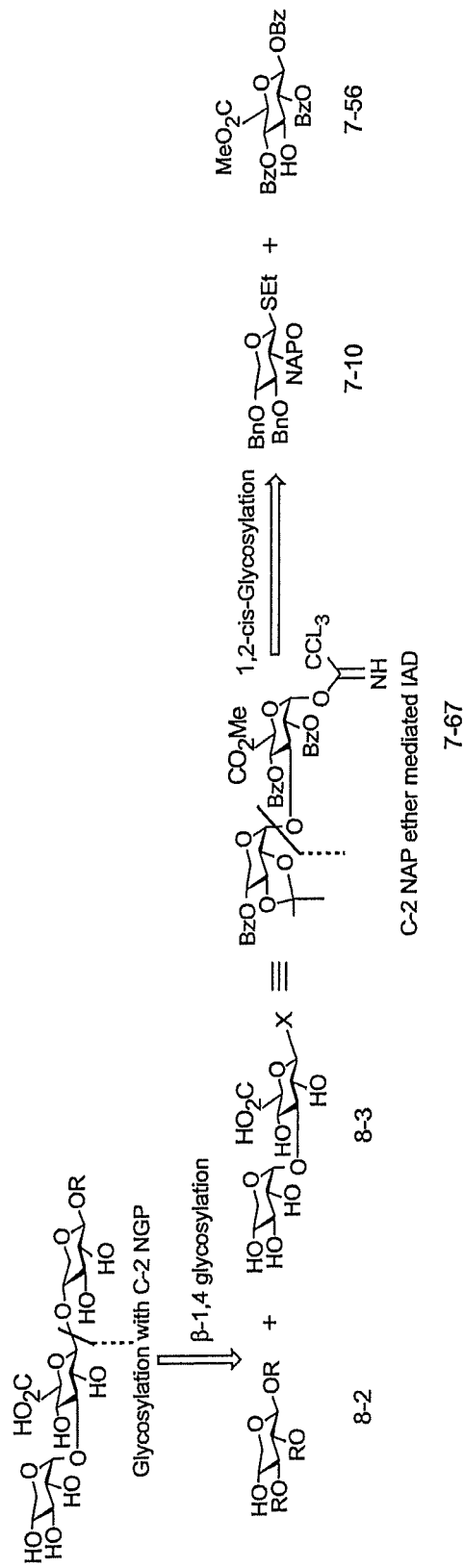
FIG. 14 Retrosynthesis of B4GAT1-trisaccharide motif 8-1

ACIDIC DYSTROGLYCAN OLIGOSACCHARIDE COMPOUND AND METHOD FOR MAKING SAME

The present application claims the benefit of provisional patent application U.S. patent application Ser, No. 62/614,173 entitled "METHOD FOR SYNTHETIC ASSEMBLY OF ACIDIC DYSTROGLYCAN OLIGOSACCHARIDES" and filed Jan. 5, 2018, the entirety of which is incorporated herein by reference for all purposes.

TECHNICAL FIELD

The present disclosure generally relates to dystroglycan oligosaccharide compounds and methods for synthetic assembly of the same.

BACKGROUND

The field of glycoscience explores the structures and functions of carbohydrates that calls for the rapid access of structurally defined oligosaccharides. In contrast to the synthesis of nucleic acids and peptides/proteins, synthetic preparation of carbohydrates remains a laborious process that necessitates the development of novel yet robust synthetic strategy to achieve automated oligosaccharide synthesis.

1.0 Synthesis of α-Dystroglycan Associated Oligosaccharides 1.1 Structure and Biological Importance of Dystrophin-glycoprotein Complex Muscular dystrophies (MDs) are a group of genetic muscle diseases that cause muscle weakness and result in a multi-system disorder in the heart, nervous system, eyes and brain. Dystrophin-glycoprotein complex (DGC)(FIG. 1), a multimeric transmembrane protein and glycoprotein complex is known to be involved in these diseases.[1] An important component of DGC is dystroglycan (DG), which connects the extracellular matrix and cytoskeleton. DG plays a critical role in organizing extracellular matrix molecules on the cell surface and in basement membranes to keep muscle membrane integrity. DG has been found in all vertebrate tissues[2] and was originally isolated from skeletal muscle as an integral membrane component of the DGC.[3] Glycosylation is the crucial post-translational modification that modulates the function of DG. Interactions between DG and its extracellular binding partners heavily rely on the carbohydrate side chains.

DG consists of two subunits, namely α-dystroglycan and β-dystroglycan. Post-translational processing through cleavage of DG yields these two differentially glycosylated non-covalently associated proteins.[4] α-Dystroglycan is a peripheral membrane protein that interacts with laminin and β-dystroglycan. On the other hand, β-Dystroglycan connects intracellularly to dystrophin, which binds to the actin cytoskeleton, and extracellularly to α-dystroglycan. β-Dystroglycan is reported to be involved in signal transduction pathways and in the maintenance of the neuromuscular junction. α-DG acts as a receptor for laminin-G (LG) domain-containing extracellular matrix proteins such as laminin, agrin, and perlecan. In addition, it serves as a receptor and entry site for most Old-World arenaviruses.[5] The size of α-dystroglycan ranges widely from 120 kDa (in brain) to 156 kDa (in skeletal muscle) due to species-specific 0-glycosylation within the mucin domain.[1b] The α-dystroglycanlaminin interaction is known to be calcium-dependent and the presence of incompletely coordinated $Ca^{2+}$ ions favors the interaction with negatively charged α-dystroglycan associated glycans.[6]

Disruption of the dystroglycan-dystrophin interaction leads to a Duchenne muscular dystrophy (DMD), and mutations disrupting the laminindystroglycan interaction lead to congenital muscular dystrophy (CMDs), collectively classified as dystroglycanopathies.[7] To date, no mutations in the dystroglycan gene have been identified in any human muscular dystrophies. The post-translational aberrant glycosylation of α-DG results in loss of receptor function, and in a broad spectrum of congenital muscular dystrophies (CMDs) that are accompanied by a variety of brain and eye malformations. In addition, perturbations of dystroglycan processing are associated with severe congenital disorders and cancer progression.[8] The knowledge of α-dystroglycan glycosyl modification has potential application in the development of therapies for CMDs.

1.2 Post-Translational Modification of α-DG and Glycan Structure Elucidation

Although α-DG is the most well-known O-mannosylated protein, the complete glycosylation pathway is not known. The endoplasmic reticulum-localized enzymes POMGNT2, B3GALNT2 and POMK contribute to the synthesis of the phosphorylated Core M3 trisaccharide (GalNAc-β-1,3-GlcNAc-β-1,4-Man) on α-DG.[9] The trisaccharide platform is used for further modification with the golgi-resident enzymes that helps binding laminin. There are several additional genes whose functions are still not known.

Recently, the bi-functional glycosyltransferase LARGE and glucuronyltransferase B4GAT1 are found to be involved in the O-mannosyl post-phosphoryl modification of α-DG.[10] (See FIG. 2). It has been reported that one of the two domains of LARGE belongs to glycosyltransferase family 8 (GT8), whose members generate products with an α-linked glycosidic bond.[11] Consequently, the enzymatic oligosaccharide product from LARGE consists of a repeating Xyl-α-(1→3)-GlcA-β-(1→3)-Xyl (GlcA=glucuronic acid, Xyl=xylose) disaccharide unit. B4GAT1 is the priming enzyme for LARGE, which uses Xyl as an acceptor. Other than the repeating sequence, the mode of glucuronyltransfer differ in LARGE from B4GAT1 on Xyl. The bi-functional LARGE installs GlcA in β-(1→3)-Xyl fashion whereas B4GAT1 has regioselective preference for C-4 position of Xyl (GlcA-β-(1→4)-Xyl).

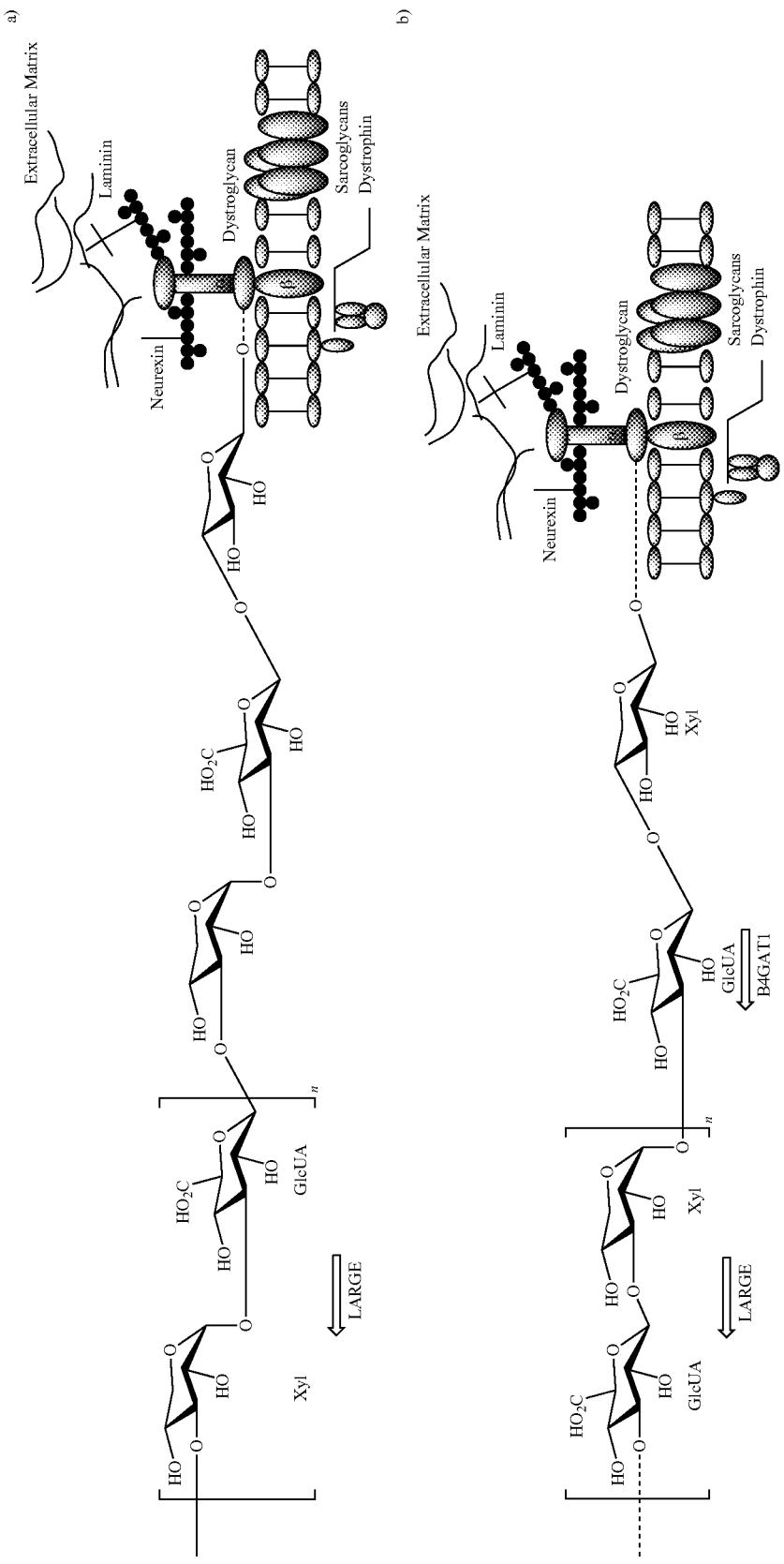

Formulas (a) and (b) Structures of LARGE and B4GAT1 glycan, respectively.

The structure of the LARGE-glycan is of specific interest because the repeating presence of a xylose unit in mammalian polysaccharide is unknown. The glycans installed after post-translational phosphoryl modification of mannose in Core M3 are attributed with interesting structural features—

1. Mammalian oligosaccharides with acidic glycan
2. Xylose at non-reducing end in mammalian glycome.
3. Multiple 1,2-cis glycocidic linkage.

1.2.1 Acidic Glycan and their Presence in Mammalian Oligosaccharides

In general, oligosaccharides possess acidic character due to the presence of one or more sugar acids in its structure. Sugar acids are monosaccharides with a carboxylic acid group in it. Depending upon the carbohydrate linear-chain length and position of carboxylic acid group, there are four types of sugar acids, i.e aldonic acid 6-1, ulosonic acid 6-2, uronic acid 6-3, and aldaric acid 6-4 (Formula 1.2.1.1).

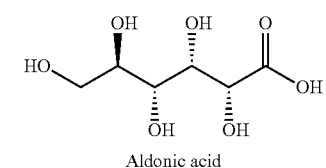

6-1

Aldonic acid

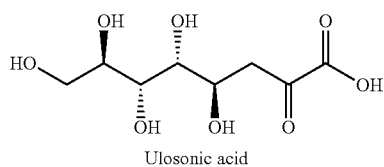

6-2

Ulosonic acid

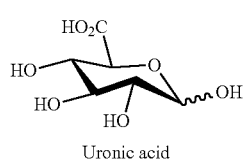

6-3

Uronic acid

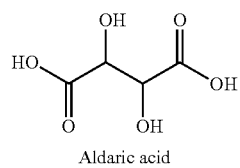

6-4

Aldaric acid

Formula 1.2.1.1 Types of Sugar Acids

The naturally occurring oligosaccharides generally contain the uronic acids. Gram-positive and Gram-negative bacteria contain a peptidoglycan layer consisting of β-(1→4)-linked N-acetylglucosamine and N-acetylmuramic acid residues. To evade attack by mammalian defense mechanisms, many bacterial pathogens mimic the mammalian sialic acid cap by developing nonoses 5-acetyl neuraminic acid (Neu5Ac), which is characterized as terminal monosaccharide in vertebrate lineage.[12] The most abundant acidic glycans found in the mammalian glycome are: Glucuronic acid (GlcA), Iduronic acid (IdoA), and Sialic acid (Sia) (Formula 1.2.1.2) although the relative abundance of these acidic glycans are comparatively small.[13]

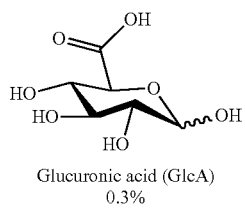

6-3

Glucuronic acid (GlcA)
0.3%

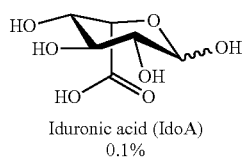

6-5

Iduronic acid (IdoA)
0.1%

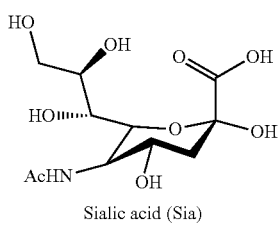

6-6

Sialic acid (Sia)
8.3%

Formula 1.2.1.2 Mammalian Acidic Glycan and their Abundance

In mammals, uronic acid is found on various O- and N-linked glycans, as well as on glycosaminoglycans (GAGs) and Glycosphingolipids, some major classes of glycopolymers. Apart from the uronic acids, sialic acids (a nine carbon backbone monosaccharides/nonoses) are also present as terminal monosaccharides on most of the mammalian glycans (Formula 1.2.1.3).

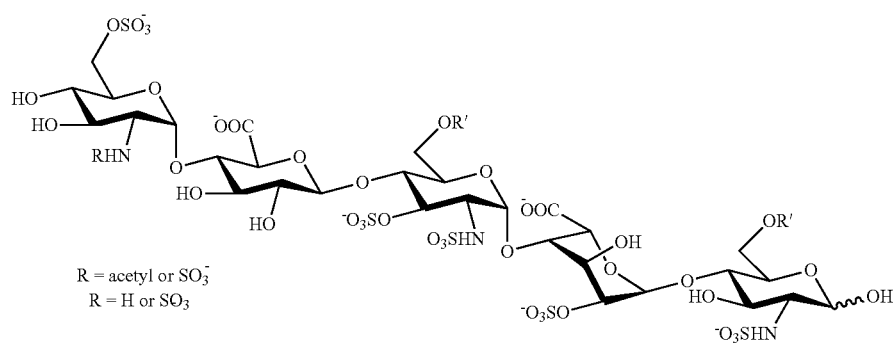

Heparan Sulfate

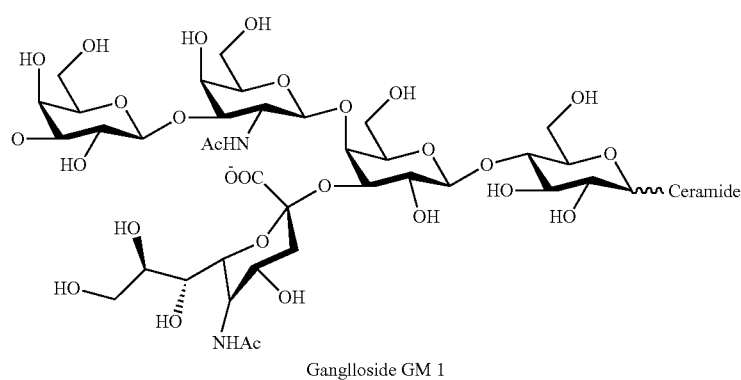

Ganglioside GM 1

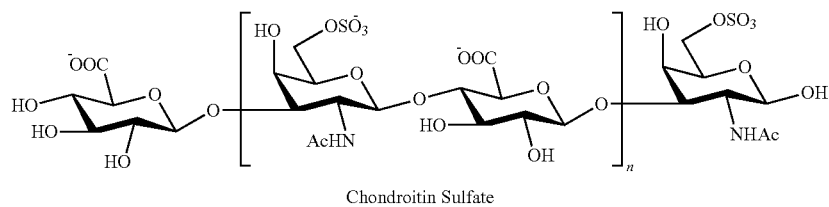

Chondroitin Sulfate

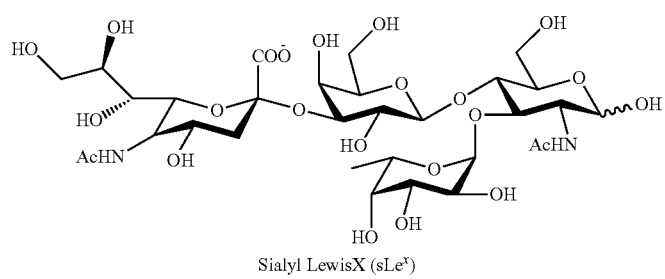

Sialyl LewisX (sLe$^x$)

Formula 1.2.1.3 Representative Mammalian Acidic Oligosaccharide

1.2.2 Xylose in Mammalian Glycome

N-linked oligosaccharides obtained from plants and animals contain xylose very frequently.[14] The most common hemicellulose in hardwood is glucuronoxylan, which consists of a β-(1→4)-linked D-xylopyranose (Xyl) unit.[15] On the contrary, the presence of Xyl in the mammalian glycome is rare; relative abundance of only 0.1%.[13]

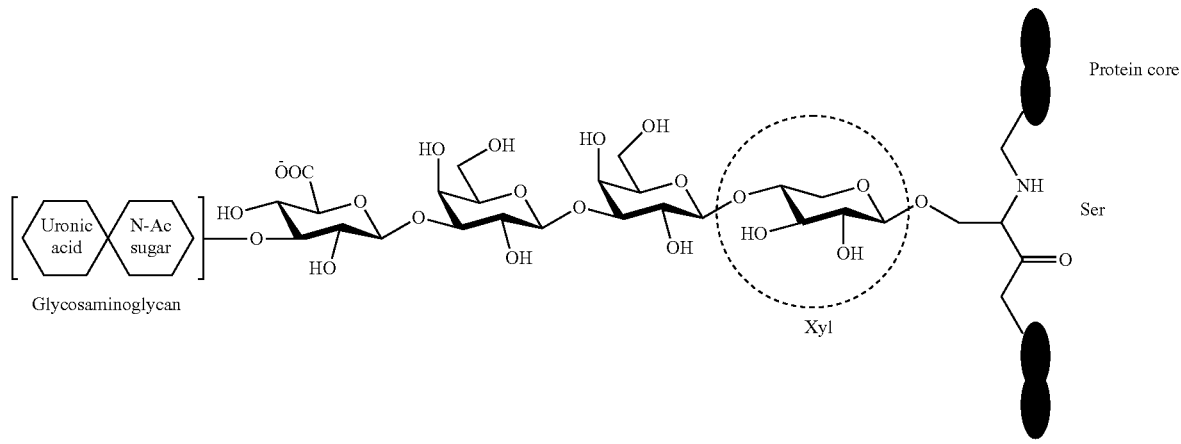

Formula 1.2.2.1 Xylosyltransferase Initiates Biosynthesis of GAG Linker on Serine of Protein Core Most often Xyl appears as an anchoring monosaccharide in post-translational glycosyl-modification. The most common linkage type found is Xyl O-glycosidically linked to serine. Xylosyltransferase initiates the biosynthesis of various glycoproteins. Glycosaminoglycans (heparin, chondroitin sulfate, and dermatan sulfate) are common glycol-conjugates with Xyl as anchoring monosaccharide. Xyl linkages are predominantly found to be β-linked in core residue of mammalian proteoglycan. The occurrence of α-linked Xyl as a terminal or repeating monosaccharide unit is extremely limited and consequently of special interest.

1.2.3 1,2-Cis Glycosidic Linkage

There are two major types of O-glycosides, considering their stereochemical orientation. Those isomers are most commonly known as α- and β-, or 1,2-cis and 1,2-trans glycosides. Both 1,2-cis and 1,2-trans glycosides are important and abundant classes of linkages in a variety of natural compounds. The compounds lacking a C-2 functional group can neither be defined as 1,2-cis nor 1,2-trans and are commonly referred to as α- and β-glycosides (Formula 1.2.3.1).

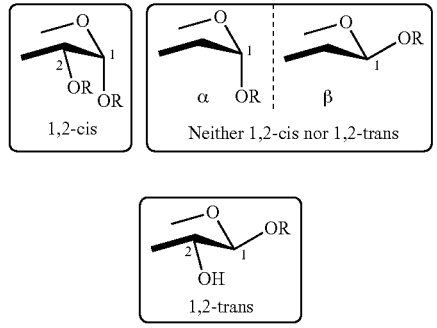

Formula 1.2.3.1 1,2-Cis Glycosidic Linkage in Natural Oligosaccharide

There are numerous natural oligosaccharides that contain 1,2-cis glycosyl linkages. High mannose-type N-linked glycans, glycosphingo-lipids of the globoside family, and Globo-H bear an important 1,2-cis-linkage.[16] A few naturally occurring oligosaccharides, which contain 1,2-cis linkages are listed in Formula 1.2.3.2.

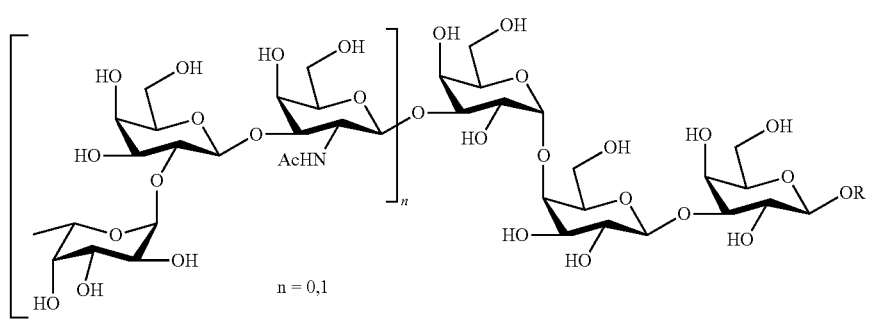

-continued

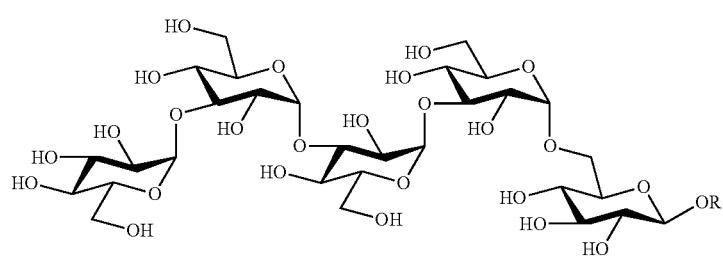

6-13

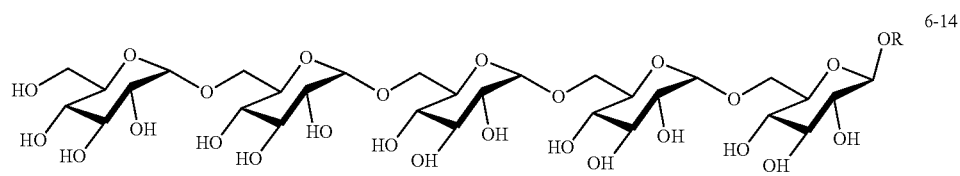

6-14

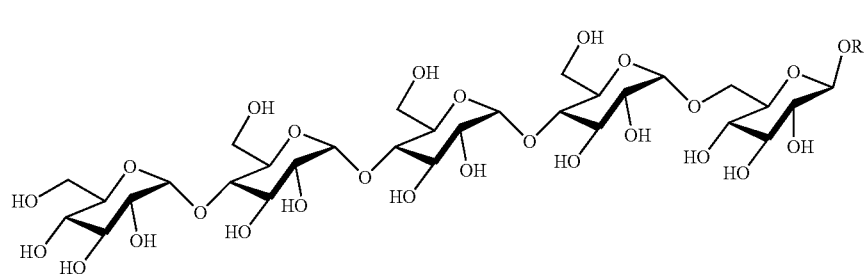

6-15

Formula 1.2.3.2 1,2-Cis Glycosidic Linkage in Natural Oligosaccharide

α-L-Fucose is the most common 1,2-cis linakge found in mammalian oligosaccharides.[13] 1,2-cis or α-linked Xyl moieties are not commonly found in mammalian oligosaccharides. Very unusual α-linked Xyl (Xyl-α-(1→3)-Xyl-α-(1→3)-Glc-β1-O-Ser) has been reported to be present in the xylosyl-glucose motif in epidermal growth factor-like domain of blood coagulation factor IX.[17]

1.3 Chemical Synthesis of 1,2-Cis Glycosides

The chemical synthesis of the 1,2-cis glycosyl linkage is always challenging.[18] The presence of a non-participating group is required, but not enough for the stereoselective synthesis of 1,2-cis glycosides. The presence of a C-2 neighbouring participating group ensures exclusive trans-glycosylations. Anomeric effect favors the α-product,[19] although the stereoselectivity of glycosylation can be poor. The selective formation of a 1,2-cis-glycosylic bonds are known to rely on leaving group effects and conformational influences.[20] Various strategies for the stereoselective synthesis of 1,2-cis-glycosides have been reported in literature (FIG. 3).

Intramolecular aglycon delivery (IAD),[18a] utilizes the transfer of a nucleophile from the adjacent C-2 carbon to the anomeric position. Hydrogen bond-mediated aglycon delivery (HAD) method takes advantage of picolinyl and picoloyl protecting groups on the C-6 position.[18b] Chiral auxiliaries at C-2 provide selectivity,[21] but require two additional steps to be removed. Additives can improve stereoselectivity by forming a less reactive intermediate in situ,[22] which may not be practical in multiple one-pot glycosylation method. Remote participation by protecting groups placed at the C-3, C-4 and/or C-6 positions of glucose (Glc) and galactose (Gal) building blocks can control the stereoselectivity of glycosylations.[23]

1.3.1 Intramolecular Aglycon Delivery

Intramolecular aglycon delivery (IAD) is a 2-step process where first an acetal linkage between O-2 of the glycosyl donor and free hydroxyl of the glycosyl acceptor is established and then activation of the donor favors intramolecular structurally restricted glycosylation (FIG. 4).

Ole Hindsagaul et al, first developed the idea of IAD in 1991 by using isopropylidene acetal as a tether for 1,2-cis-mannopyranosylation,[24] Later, Stork et. al. developed a method using silyl acetal for a tether.[25] Further Fairbanks employed allyl ether as the precursor of enol ether' which was converted to mixed acetal by using iodonium salt.[26] Later he used vinyl ether as a tether with a less hindered group.

A different approach was taken by Ito and Ogawa by employing a 4-methoxy benzyl protecting group on the C-2 position.[27] Ito utilized the oxidation of a PMB group with single electron oxidant 2,3-Dichloro-5,6-dicyano-1,4-benzoquinone (DDQ) which gives an oxycarbenium ion 6-17 that can be attacked by a free hydroxyl of the glycosyl acceptor to give a mixed acetal 6-18. An intramolecular glycosylation reaction upon promoting the thioglycoside afforded the 1,2-cis glycoside products 6-21 (Scheme 1.3.1.1).

Scheme 1.3.1.1 PMB-tether mediated IAD

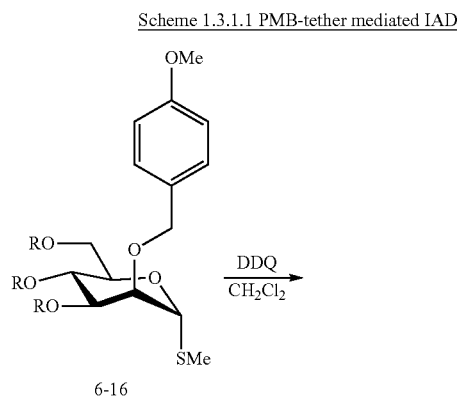

glucose 6-22 with acceptor 6-23 resulted in a mixed acetal 6-24 and subsequent promotion of methylthioglycoside with MeOTf-DTBMP yielded selective α-anomer 6-25 in 63% yield (Scheme 1.3.1.2).

Scheme 1.3.1.2 NAP-tethered IAD and activation of thioglycoside with MeOTf

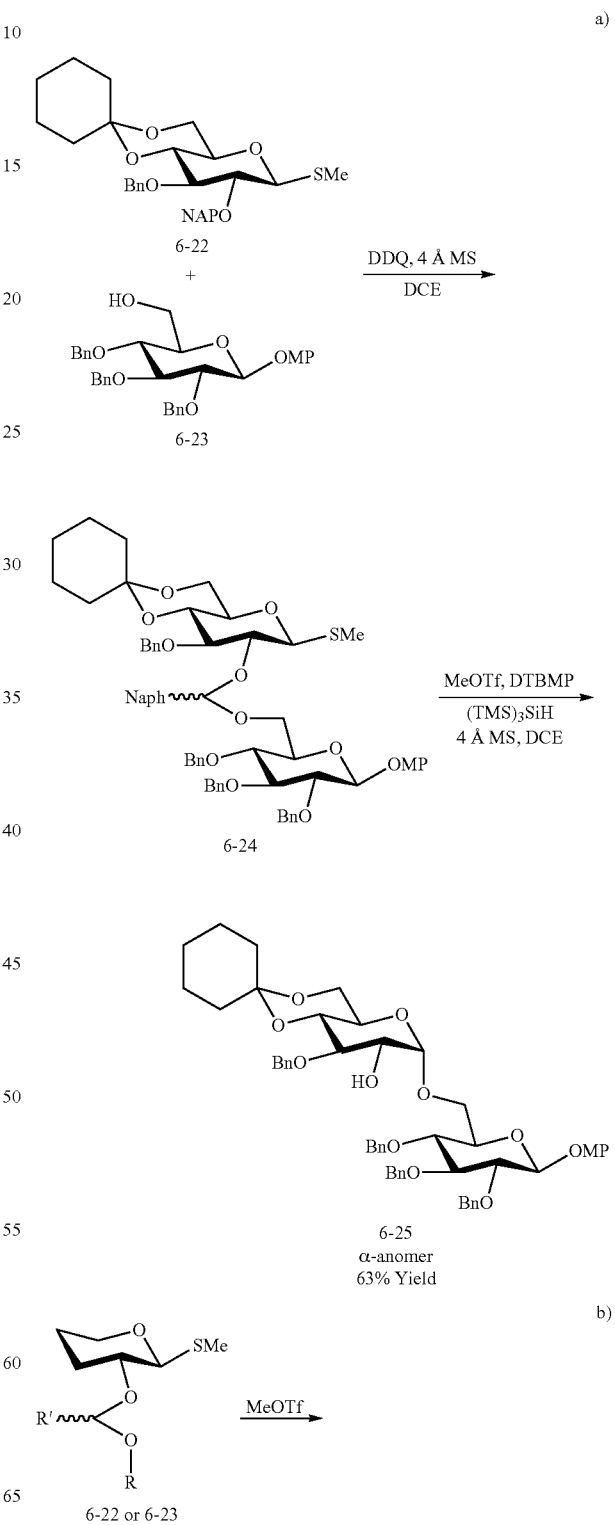

Using the same strategy Ito also reported 1,2-cis IAD by using 2-napthylmethyl (NAP) as a tether,[28] The NAP group underwent similar oxidization in presence of DDQ. In anhydrous conditions, the reaction of 2-O-NAP protected 15
-continued

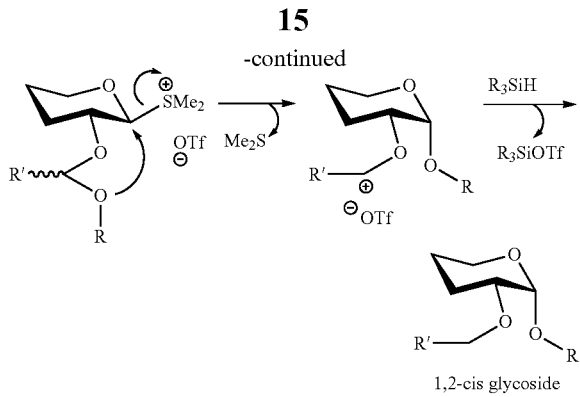

R' = PMB, NAP

Although Ito's process showed promising results in 1,2-cis glycosylation, the major drawbacks for this sequence are i) 2-step process that requires intermediate work-up and purification, ii) use of acidic MeOTf which may interrupt acid-sensitive protecting groups, and iii) the activation of thioglycoside with MeOTf is very sluggish (takes more than 16-20 h), iv) the activation might require warming of the reaction mixture.

BRIEF SUMMARY OF THE DISCLOSURE

One aspect of a preferred embodiment of the present disclosure comprises a synthetic dystroglycan oligosaccharide comprising:

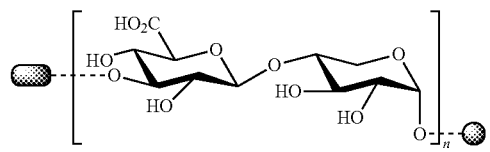

wherein a repeating disaccharide motif consists of Glucuronic Acid (ClcA) and Xylose (Xyl) having a defined glycosyl connection GlcA-β-(1→3)-Xyl-α-(1→3)-GlcA; wherein either end of the synthetic dystroglycan oligosaccharide is conjugatable with chemical or biological vehicle or support; wherein the non-reducing terminal (shown as ▨)

is conjugatable with any oligosaccharides or groups that can modify a hydroxyl functionality; and wherein the reducing terminal (shown as ●)

is conjugatable with any tags, oligosaccharides or anything that can modify a hydroxyl functionality.

In another aspect of a preferred synthetic dystroglycan oligosaccharide of the present disclosure, the non-reducing terminal

16

(shown as ▨)

is conjugatable win one or more of an acyl group and a lipid chain.

In yet another aspect of a preferred synthetic dystroglycan oligosaccharide of the present disclosure, the reducing terminal (shown as ●)

is conjugatable with one or more of (i) a tag selected from the group comprising a linker, a fluorophore, an affinity agent, a peptide, and a protein, (ii) an acyl group and (iii) a lipid chain.

Another aspect of a preferred embodiment of the present disclosure comprises a synthetic dystroglycan oligosaccharide comprising:

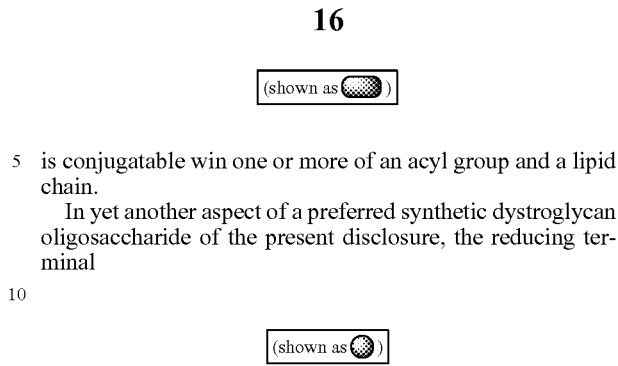

wherein a repeating disaccharide motif consists of Glucuronic Acid (ClcA) and Xylose (Xyl) having a defined glycosyl connection GlcA-β-(1→3)-Xyl-α-(1→3)-GlcA; wherein either end of the synthetic dystroglycan oligosaccharide is conjugatable with chemical or biological vehicle or support; wherein the non-reducing terminal (shown as ▨)

is conjugatable with any oligosaccharides or groups that can modify a hydroxyl functionality including one or more of acyl groups and lipid chains; and wherein the reducing terminal (shown as ●)

is conjugatable with any tags including one or more of linkers, fluorophores, affinity agents, peptides and proteins or any oligosaccharides or anything that can modify a hydroxyl functionality including one or more of acyl groups and lipid chains.

Yet another aspect of a preferred embodiment of the present disclosure comprises a synthetic dystroglycan oligosaccharide comprising:

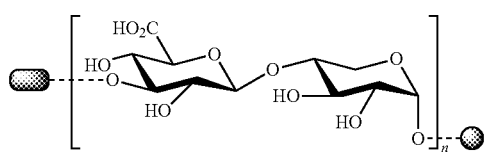

wherein a repeating disaccharide motif consists of Glucuronic Acid (GlcA) and Xylose (Xyl) having a defined glycosyl connection GlcA-β-(1→4)-Xyl-α-(1→3)-GlcA; wherein either end of the synthetic dystroglycan oligosaccharide is conjugatable with chemical or biological vehicle or support; wherein the non-reducing terminal

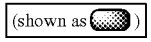

is conjugatable with any oligosaccharides or groups that can modify a hydroxyl functionality including one or more of acyl groups and lipid chains; and wherein the reducing terminal is

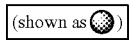

is conjugatable with any tags including one or more of linkers, fluorophores, affinity agents, peptides and proteins or any oligosaccharides or anything that can modify a hydroxyl functionality including one or more of acyl groups and lipid chains.

Another aspect of a preferred embodiment of the present disclosure comprises a synthetic dystroglycan oligosaccharide comprising:

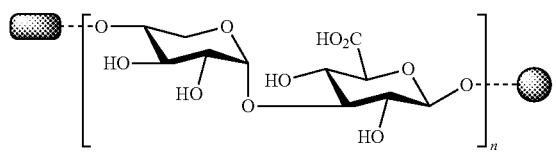

wherein a repeating disaccharide motif consists of Glucuronic Acid (GlcA) and Xylose (Xyl) having a defined glycosyl connection GlcA-β-(1→4)-Xyl-α-(1→3)-GlcA; wherein either end of the synthetic dystroglycan oligosaccharide is conjugatable with chemical or biological vehicle or support; wherein the non-reducing terminal

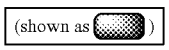

is conjugatable with any oligosaccharides or groups that can modify a hydroxyl functionality including one or more of acyl groups and lipid chains; and wherein the reducing terminal

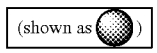

is conjugatable with any tags including one or more of linkers, fluorophores, affinity agents, peptides and proteins or any oligosaccharides or anything that can modify a hydroxyl functionality including one or more of acyl groups and lipid chains.

In another aspect, the synthetic dystroglycan oligosaccharide of the present disclosure preferably further comprises a disaccharide having the structure:

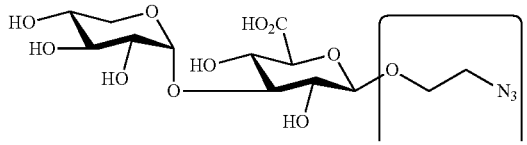

wherein the

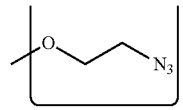

chemical modulation serves a handle for further conjugation.

In another aspect, the synthetic dystroglycan oligosaccharide of the present disclosure preferably further comprises a tetrasaccharide having the structure:

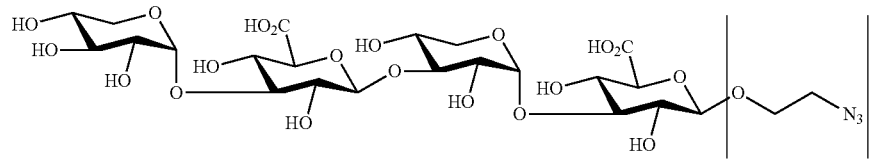

wherein the

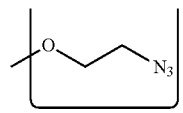

chemical modulation serves a handle for further conjugation.

In another aspect, the synthetic dystroglycan oligosaccharide of the present disclosure preferably further comprises a hexasaccharide having the structure:

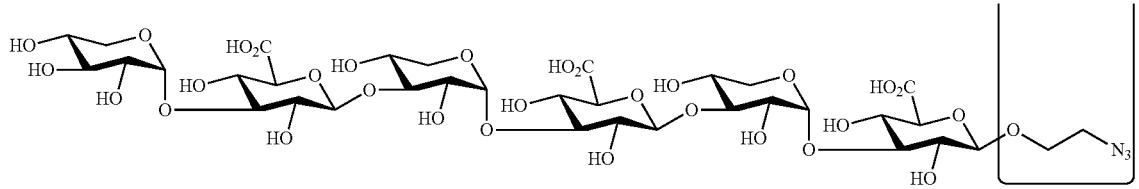

wherein the

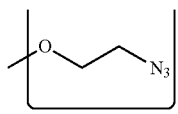

chemical modulation serves a handle for further conjugation.

In another aspect, the synthetic dystroglycan oligosaccharide of the present disclosure preferably further comprises a trisaccharide having the structure:

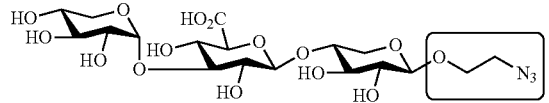

wherein the

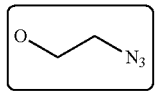

chemical modulation serves a handle for further conjugation.

A further aspect of a preferred embodiment of the present disclosure comprises a method for preparing a synthetic dystroglycan oligosaccharide comprising:

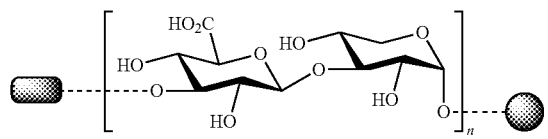

with a repeating disaccharide motif consisting of Glucuronic Acid (GlcA) and Xylose (Xyl) having a defined glycosyl connection GlcA-β-(1→3)-Xyl-α-(1→3)-GlcA comprising: employing a Schmidt's glycosylation reaction with glucuronyl trichloroacetimidate as a donor with a C-2 neighboring participating group; driving the Schmidt's glycosylation reaction in regioselective manner using an acceptor having a 2,3-dihydroxy xylose moiety to produce a GlcA-β-(1→3)-Xyl connection; and using a base mediated deprotection method to remove protecting groups from the product of the Schmidt's glycosylation reaction to produce the synthetic dystroglycan oligosaccharide.

A further aspect of a preferred embodiment of the present disclosure comprises a method for preparing a synthetic dystroglycan oligosaccharide comprising:

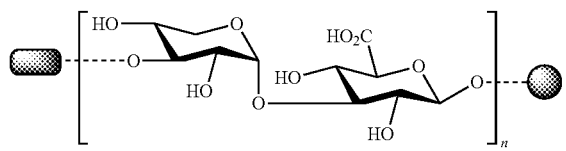

with a repeating disaccharide motif consists of Glucuronic Acid (GlcA) and Xylose (Xyl) having a defined glycosyl connection GlcA-β-(1→3)-Xyl-α-(1→3)-GlcA, comprising: using a redox mediated one-pot intramolecular aglycon delivery (IAD) reaction comprising activating xylose thioglycoside with 2,3-Dichloro-5,6-dicyano-p-benzoquinone (DDQ) to produce a mixed acetal; reacting the mixed acetal with tris-(4-bromophenyl) ammoniumyl hexachloroantimonate (BAHA), a single electron transfer reagent and 3-OH glucuronic acid acceptor to produce a 1,2-cis glycosylated product; and using a base mediated deprotection method to remove protecting groups from the 1,2-cis glycosylated product to produce the synthetic dystroglycan oligosaccharide.

Another aspect of a preferred embodiment of the present disclosure comprises a method for preparing a synthetic dystroglycan oligosaccharide comprising:

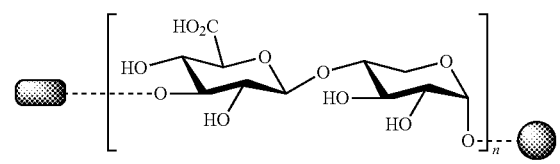

with a repeating disaccharide motif consists of Glucuronic Acid (GlcA) and Xylose (Xyl) having a defined glycosyl connection GlcA-β-(1→4)-Xyl-α-(1→3)-GlcA, comprising: employing a Schmidt's glycosylation reaction with glucuronyl trichloroacetimidate as a donor with a C-2 neighboring participating group; driving the Schmidt's glycosylation reaction using a 4-OH Xyl acceptor to produce a β-(1→4) glycosyl connection; and using a base mediated deprotection method to produce the synthetic dystroglycan oligosaccharide having the defined glycosyl connection GlcA-β-(1→4)-Xyl-α-(1→3)-GlcA.

A further aspect of a preferred embodiment of the present disclosure comprises a method for preparing a synthetic dystroglycan oligosaccharide comprising:

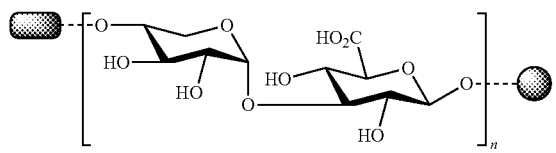

with a repeating disaccharide motif consists of Glucuronic Acid (GlcA) and Xylose (Xyl) having a defined glycosyl connection GlcA-β-(1→4)-Xyl-α-(1→3)-GlcA, comprising: using a redox mediated one-pot intramolecular aglycon delivery (IAD) reaction comprising activating xylose thioglycoside with 2,3-Dichloro-5,6-dicyano-p-benzoquinone (DDQ) to produce a mixed acetal; reacting the mixed acetal with tris-(4-bromophenyl) ammoniumyl hexachloroantimonate (BAHA), a single electron transfer reagent and 3-OH glucuronic acid acceptor to produce a 1,2-cis glycosylated product; and using a base mediated deprotection method to remove protecting groups from the 1,2-cis glycosylated product to produce the synthetic dystroglycan oligosaccharide.

Another aspect of a preferred embodiment of the present disclosure comprises a method for preparing a synthetic dystroglycan disaccharide having the structure:

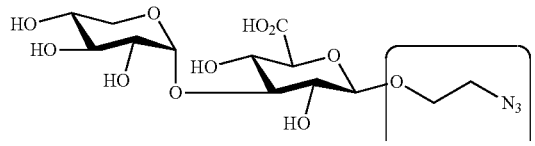

with a disaccharide motif consisting of Glucuronic Acid (GlcA) and Xylose (Xyl) having a defined glycosyl connection Xyl-α-(1→3)-GlcA, comprising: employing a Schmidt's glycosylation reaction with protected disaccharide [Xyl-α-(1→3)-GlcA] trichloroacetimidate as a donor with a C-2 neighboring participating group on reducing end GlcA; driving the Schmidt's glycosylation reaction using a 2-azidoethanol acceptor to produce a chemical modulation serving as a handle for further conjugation; and using a base mediated deprotection method to produce the synthetic dystroglycan oligosaccharide having the defined synthetic dystroglycan disaccharide.

A further aspect of a preferred embodiment of the present disclosure comprises a method for preparing a synthetic dystroglycan tetrasaccharide having the structure:

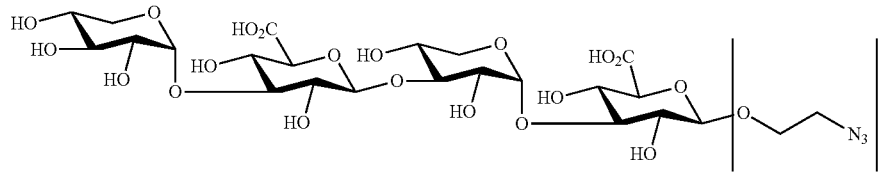

with a tetrasaccharide motif consisting of a repeating disaccharide motif consisting of Glucuronic Acid (GlcA) and Xylose (Xyl) having a defined glycosyl connection Xyl-α-(1→3)-GlcA-β-(1→3)-Xyl-α-(1→3)-GlcA, comprising: employing a Schmidt's glycosylation reaction with a protected disaccharide [Xyl-α-(1→3)-GlcA] trichloroacetimidate as a donor with a C-2 neighboring participating group on reducing end GlcA; driving the Schmidt's glycosylation reaction using a protected 2-azidoethyl-2,3-di-hydroxy-Xyl-α-(1→3)-GlcA acceptor to produce a chemical modulation serving as a handle for further conjugation; and using a base mediated deprotection method to produce the synthetic dystroglycan tetrasaccharide having the defined glycosyl connection Xyl-α-(1→3)-GlcA-β-(1→3)-Xyl-α-(1→3)-GlcA.

Another aspect of a preferred embodiment of the present disclosure comprises a method for preparing a synthetic dystroglycan hexasaccharide having the structure:

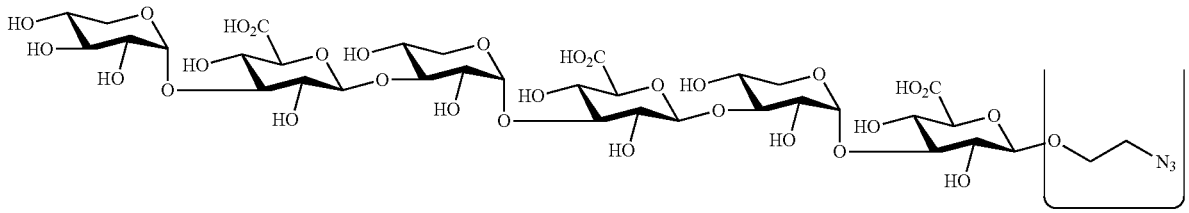

with a hexasaccharide motif consisting of a repeating disaccharide motif consisting of Glucuronic Acid (GlcA) and Xylose (Xyl) having a defined glycosyl connection Xyl-α-(1→3)-GlcA-β-(1→3)-Xyl-α-(1→3)-GlcA-β-(1→3)-Xyl-α-(1→3)-GlcA, comprising: employing a Schmidt's glycosylation reaction with a protected tetrasaccharide [Xyl-α-(1→3)-GlcA-β-(1→3)-Xyl-α-(1→3)-GlcA] trichloroacetimidate as a donor with a C-2 neighboring participating group on reducing end GlcA; driving the Schmidt's glycosylation reaction using a protected 2-azidoethyl-2,3-dihydroxy-Xyl-α-(1→3)-GlcA acceptor to produce a chemical modulation serving as a handle for further conjugation; and using a base mediated deprotection method to produce the synthetic dystroglycan hexasaccharide having the defined glycosyl connection Xyl-α-(1→6)-GlcA-β-(1→3)-Xyl-α-(1→3)-GlcA-β-(1→3)-Xyl-α-(1→3)-GlcA.

A further aspect of a preferred embodiment of the present disclosure comprises a method for preparing a synthetic dystroglycan trisaccharide having the structure:

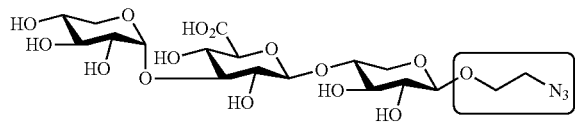

with a trisaccharide motif consisting of Glucuronic Acid (GlcA) and Xylose (Xyl) having a defined glycosyl connection Xyl-α-(1→3)-GlcA-β-(1→4)-Xyl, comprising: employing a Schmidt's glycosylation reaction with a protected disaccharide [Xyl-α-(1→3)-GlcA] trichloroacetimidate as a donor with a C-2 neighboring participating group on the reducing end GlcA; driving the Schmidt's glycosylation reaction using a protected 2-azidoethyl-4-hydroxy-Xyl acceptor to produce a chemical modulation serving as a handle for further conjugation; and using a oxidative debenzylation (sodium bromate+sodium dithionate) followed by the base mediated deprotection method to produce the synthetic dystroglycan trisaccharide having the defined glycosyl connection Xyl-α-(1→3)-GlcA-β-(1→4)-Xyl.

It is to be understood that both the foregoing general description and the following detailed description are exemplary, but not restrictive, of the present disclosure.

BRIEF DESCRIPTION OF THE SEVERAL VIEWS OF THE DRAWINGS

For the present disclosure to be easily understood and readily practiced, the present disclosure will now be described for purposes of illustration and not limitation in connection with the following figures, wherein:

FIG. 1 shows a dystrophin-glycoprotein complex;

FIG. 2 shows glycosylation of α-dystroglycan and localization of glycosyltransferases involved in the O-glycosylation pathway;

FIG. 3 schematically shows Various methods for synthesis of a 1,2-cis glycosidic bond;

FIG. 4 shows an Intramolecular Aglycon Delivery (IAD) reaction;

FIG. 5 shows oxidative activation of thioglycoside;

FIG. 6 shows a 2-napthylmethyl (NAP)-mediated rapid one-pot IAD;

FIG. 7 shows 1,2-cis disaccharide and disaccharide-linker synthesized via one-pot IAD;

FIG. 8 shows pre- and post-glycosylation to install uronic acid in an oligosaccharide;

FIG. 9 shows retrosynthetic approach towards LARGE glycan including (a) post-glycosylation oxidation strategy and (b) pre-glycosylation oxidation strategy;

FIG. 10 shows a donor and acceptor by design for post-glycosylation oxidation strategy;

FIG. 11 shows synthesis of a modified disaccharide for unified donor-acceptor strategy;

FIG. 12 shows glycosyl modification of α-DG core with B4GAT1 and LARGE enzymes;

FIG. 13 shows Xyl-α-(1→3)-GlcA-β-(1→4)-Xyl as a target trisaccharide motif; and FIG. 14 shows retrosynthesis of B4GAT1-trisaccharide motif 8-1.

DETAILED DESCRIPTION

The following description, taken in conjunction with the referenced drawings, is presented to enable one of ordinary skill in the art to make and use the disclosure and to incorporate it in the context of particular applications. Various modifications, as well as a variety of uses in different applications, will be readily apparent to those skilled in the art, and the general principles, defined herein, may be applied to a wide range of aspects. The present disclosure is not intended to be limited to the aspects disclosed herein. Instead, it is to be afforded the widest scope consistent with the disclosed aspects.

In the present disclosure, addressed is the important issue associated with the functions of carbohydrate modification in dystroglycan (DG) in muscular dystrophies (MDs), a group of muscle diseases, for which currently no cure is available. Sorting out the relationships between the various molecular defects in glycosylation and the modes of disease presentation is challenging. The enzymatic oligosaccharide product from LARGE gene has been recently identified, which consists of a repeating α(1→3)-GlcUA-β-(1→3)-Xyl disaccharide unit. According to the present disclosure, a template directed 1,2-cis glycosylation was preferably utilized to synthesize a series of α-DG associated glycans. Additionally, a successful synthesis is demonstrated for B4GAT1 enzymatic trisaccharide, which is also found to be involved in post-translational modification. The present disclosure preferably may serve as the basis for finding novel medical solutions to neurological diseases that commonly causes cardiac muscle dystrophies and brain diseases.

According to the present disclosure, the shortfalls of the prior art are addressed via an oxidative promotion of thioglycoside to enable a one-pot rapid IAD. The mixed acetal formation under oxidative DDQ condition and a suitable oxidative promotion of thioglycoside is well in sync according to the present disclosure (Scheme 1.3.1.3).

Scheme 1.3.1.3 One-pot IAD under oxidative condition

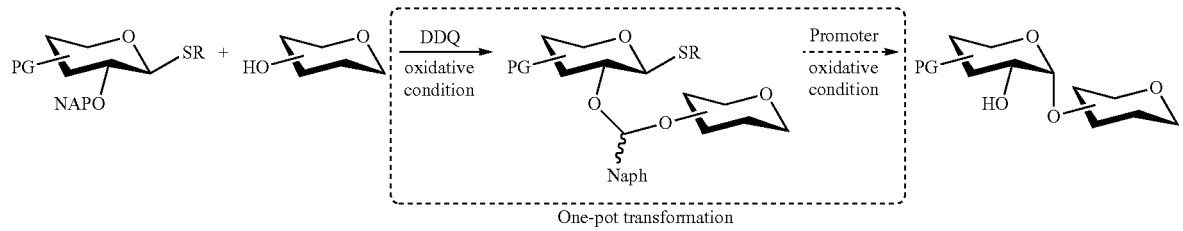

Sinay and Pinto reported the activation of thioglycosides using a stoichiometric amount of salt tris-(4-bromophenyl) ammoniumyl hexachloroantimonate (BAHA) 6-26 with excellent yield.[29] The amine radical cation involved in single electron transfer (SET) oxidation process to generate sulfur radical cation, which is cleaved to give oxocarbenium ion and eventually undergoes glycosylation (FIG. 5).

Interestingly, BAHA operates under a radical mechanism and hence the reaction is very fast at room temperature. DDQ in addition to BAHA provides an excellent opportunity for one-pot IAD glycosylation according to the present disclosure.

1.3.2 Development of One-Pot Rapid IAD

The fundamental concept of one-pot IAD relies on the compatibility of BAHA under DDQ reaction condition is that first DDQ will oxidize C-2 NAP to form a mixed acetal, which will be successively activated and gives the final 1,2-cis glycosylation product. According to the present disclosure, addition of base ($K_2CO_3$) is important to carry on the BAHA operated thioglycoside activation. (FIG. 6).

In the presence of 4 Å molecular sieves (MS), the donor thioglycoside and acceptor formed mixed acetal under DDQ conditions with acetonitrile (MeCN) as the solvent of choice. After 3-4 h, 0.4 eq of $K_2CO_3$ was introduced followed by BAHA. The reaction mixture was finally washed with ascorbic acid buffer which afforded the desired 1,2-cis disaccharide without NAP in good yield.

A series of glycosylations were performed according to the present disclosure involving various monosaccharides and linkers. The challenging linkages of β-mannose (for ex. 6-39) and β-rhamnose (for ex. 6-32) were synthesized very conveniently (FIG. 7). The method was proved to be robust and gentle enough to be compatible with a variety of sugar backbone protecting groups.

With the reliable 1,2-cis glycosylation methodology in hand according to the present disclosure, next to be addressed were the challenges associated with the synthesis of LARGE-glycans, which contains a Xyl-α-(1→3)-GlcA linkage.

2.0 Synthesis of a Series of Large Glycans 2.1 Retrosynthesis of LARGE-Glycans

The chemical structure of LARGE-glycan is shown above in Formula (a). The linear oligosaccharide contains a repeating Xyl-α-(1→3)-GlcA disaccharide unit. The GlcA unit is p-linked at its reducing end with the Xyl in β-(1→3) fashion (Formula 2.1.1).

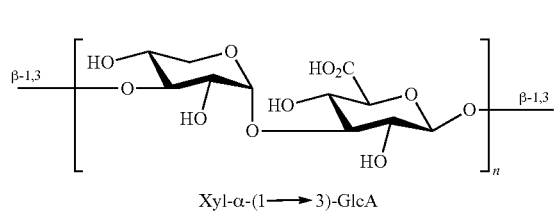

Xyl-α-(1→3)-GlcA

Formula 2.1.1 Repeating Disaccharide Unit in LARGE-Glycan

The presence of GlcA in the final oligosaccharide calls for two parallel retrosynthetic approaches—i) post-glycosylation oxidation, where C-6 hydroxyls of uronic acid precursors are oxidized at late stage and ii) pre-glycosylation oxidation, where the carboxylic acid in uronic acid building block is protected as an ester and then undergoes glycosylation (FIG. 8).

Preferably, the post-glycosylation oxidation approach of the present disclosure uses glucose (Glc) as GlcA precursor. GlcA unit will be obtained from glucose precursor by late stage selective oxidation at C-6 position. The repeating unit now consists of a Xyl-α-(1→3)-Glc unit. To synthesize the oligomeric chain, the disaccharide units can be joined in selective Glc-β-(1→3)-Xyl fashion by taking advantage of C-2 neighboring group participation (NGP) by benzoate ester protecting group. The glycosylation will be achieved by a complimentary trichloroacetimidate glycosylation method. The repeating Xyl-α-(1→3)-Glc unit is preferably synthesized according to the present disclosure employing a C-2 NAP-assisted α-selective one-pot glycosylation method on C-2 NAP protected Xyl and C-3 hydroxyl glucose building blocks (FIG. 9(a)).

On the other hand, the pre-glycosylation oxidation strategy of the present disclosure preferably involves a TCA-mediated β-selective glycosylation of Xyl-α-(1→3)-GlcA unit to form the oligosaccharide. The repeating Xyl-α-(1→3)-GlcA unit is preferably synthesized according to the present disclosure employing a one-pot 1,2-cis glycosylation method on C-2-NAP protected Xyl and C-3 hydroxyl GlcA building block. A differentially protected Glc monosaccharide will be transformed to GlcA acceptor for this purpose (FIG. 9(b)).

2.2 Forward Synthesis of LARGE Oligosaccharide

The disconnection of the important disaccharide repeating unit and the one-pot 1,2-cis glycosylation methodology of the present disclosure provides leverage to explore the total synthesis of a series of LARGE glycans. To address the mysteries associated with the functions of glycosyl modification in α-dystroglycan, a series of glycans that contain well-defined numbers of Xyl-α-(1→3)-GlcA disaccharide motifs is useful. The synthesized compounds facilitate the studies of their functions in CMDs.

2.2.1 Postglycosylation Oxidation Strategy: Generation I

First, the forward synthesis sequence was preferably approached using a post-glycosylation oxidation strategy (FIG. 9(a)). In the postglycosylation-oxidation strategy the oligosaccharide chain is assembled using non-oxidized glycosyl building blocks, after which the carboxylate groups are introduced at the oligomer level. There are a few advantages in choosing Glc as a GlcA precursor. GlcA is comparatively less reactive than Glc under standard glycosylation conditions. There are chances of side reactions, like β-elimination and fragmentation involving the carboxylic acid group on GlcA. The repeating disaccharide unit was first synthesized to test the robustness of the preferred one-pot 1,2-cis-glycosylation process and the feasibility of late state oxidation. Preferably, a C-3 hydroxyl Glc would do the job. The C-2 position of Glc must be protected with an ester to facilitate NGP-assisted β-selective glycosylation and a preferred choice of protection is with benzoyl group (OBz). Uniform protecting groups would help to accomplish a single final deprotection process and hence 1,2,4,6-tetra-O-benzoyl glucopyranoside 7-11 was preferably chosen as the acceptor in 1,2-cis glycosylation. The Xyl donor monosaccharide requires a functional C-2 napthylmethyl group to mediate 1,2-cis glycosylation. Xyl C-3 and C-4 positions were protected with benzyl group (OBn) to make the donor 'armed' (7-10), which would help in efficient and quick glycosylation (FIG. 10).

Thioglycoside donor 7-10 was synthesized in eight linear sequences (Scheme 2.2.1.1). Commercially available D-xylose was per-acetylated with acetic anhydride and pyridine condition followed by anomeric bromination with 33% HBr-Acetic acid gave per-OAc-Xyl bromide in 86% yield. Treatment of 7-14 with EtSH in presence of base 2,6-lutidine gave the thio-orthoester. Subsequent deprotection of acetyl groups and protection with a benzyl group afforded 3,4-di-O-benzyl protected Xyl thio-orthoester in 63% overall yield. Opening of orthoester was accomplished in the presence of Lewis acid TMSOTf and the C-2 acetyl group was removed with a treatment of sodium methoxide in methanol to obtain 7-19. NAP was installed at C-2 Xyl to afford donor 7-10 in 75% yield over 2 steps.

Scheme 2.2.1.1 Synthesis of C-2-NAP Xyl donor 7-10

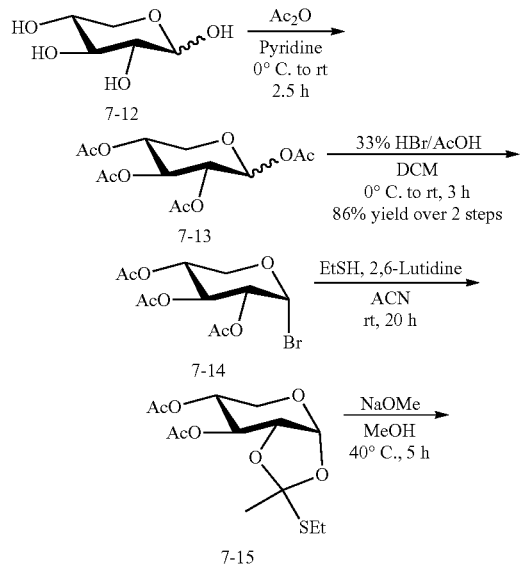

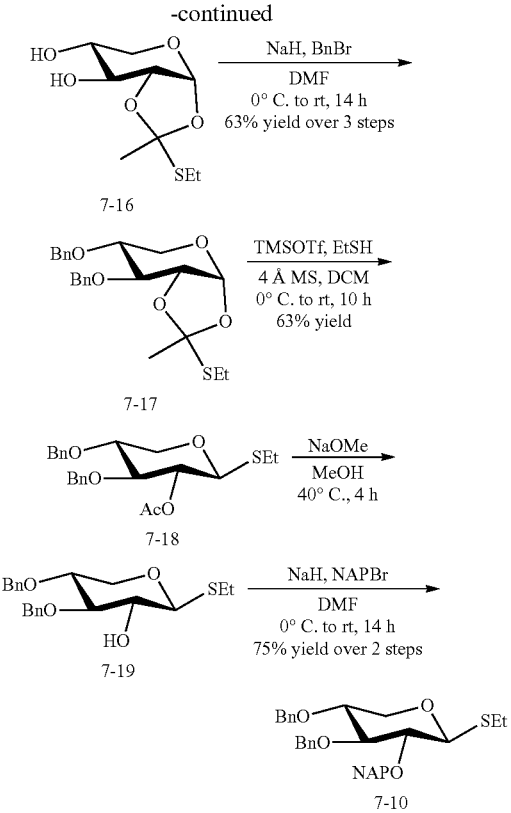

Glc acceptor 7-11 was prepared from commercially available D-glucose diacetonide 7-20 as a starting material. Protection of C-3 hydroxyl with a benzyl group and subsequent removal of acetonides helped to rearrange the ring structure from furanose to pyranose to afford 3-O-Bn D-glucopyranoside 7-22. All the hydroxyl groups were then protected with —OBz with an overall yield of 60%. Hydrogenolysis with catalytic Pd(OH)$_2$/C and under hydrogen balloon gave the desired C-3-hydroxy glucose acceptor 7-11 in 91% yield (Scheme 2.2.1.2).

Scheme 2.2.1.2 Synthesis of C-3-OH glucose acceptor

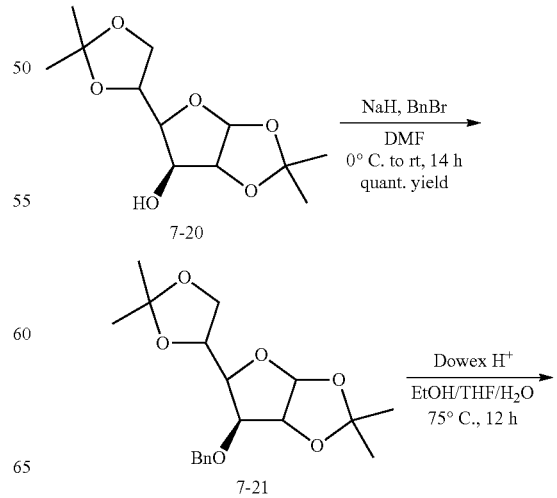

-continued

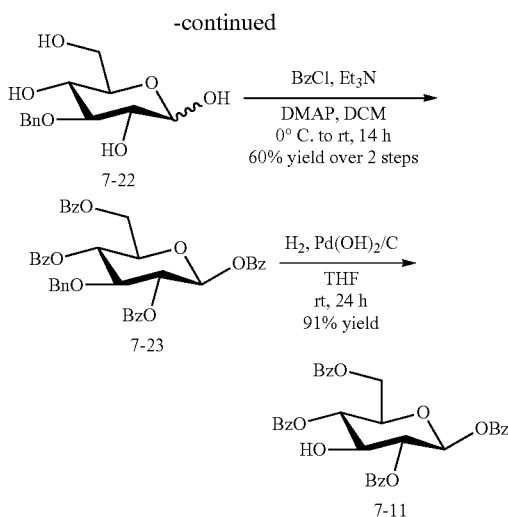

With both the donor 7-10 and acceptor 7-11 in hand, one-pot redox 1,2-cis glycosylation was employed according to the present disclosure. 7-10 and 7-11 were coevaporated with toluene twice and kept under high vacuum for 1 h to let them dry. The mixture was treated with DDQ in presence of DCM and 4 Å MS. Once the mixed acetal 7-24 was formed, oven-dried K₂CO₃ and BAHA were added sequentially. Final work-up with ascorbic acid buffer yielded the desired α-disaccharide 7-25 in 61% yield (Scheme 2.2.1.3).

Scheme 2.2.1.3 Synthesis of disaccharide 7-25 via one-pot redox IAD

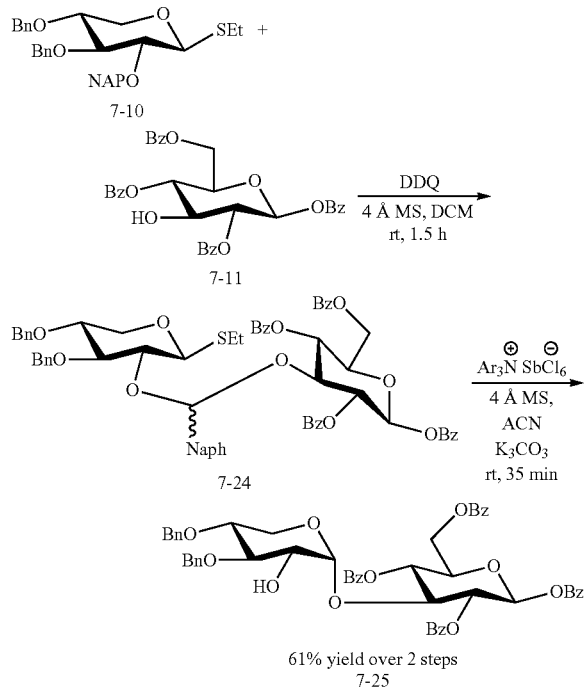

Preferably, the 2-azidoethanol 7-31 linker may be installed on the disaccharide 7-25 to give a handle for further functionality studies. The azide linker was known to be stable in various sugar backbone manipulation processes and can act as an anchor to conjugate with a polymer, modified glass-surface, nano-particles, and biomolecules. Before the glycosylation with the linker, the Xyl-C-2 position of disaccharide 7-25 was attempted to protect with a —OBz group (Scheme 2.2.1.4). Surprisingly, the seemingly routine benzoylation of 7-25 was found to be very slow (only 60% conversion in 3 days at elevated temperature) to give product 7-26. The disaccharide thus obtained was then converted to glycosyl donor 7-27 and glycosylated with 1-octanol. Interestingly, the deprotection of multiple —OBz under NaOMe condition, followed by silyl protection at C-6 position of Glc, and acetylation yielded a disaccharide 7-28 that contained a single residual —OBz group, presumably at Xyl-C-2 position (in bold letter) (Scheme 2.2.1.4). From these two facts, it can be inferred that the Xyl C-2 position of the disaccharide 7-25 is comparatively inaccessible.

Scheme 2.2.1.4 Inaccessibility of Xyl C-2 position on disaccharide 7-25

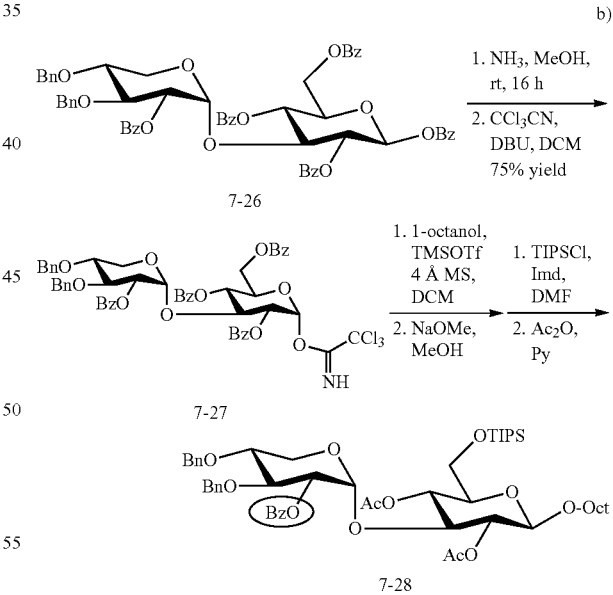

According to the present disclosure, the next preferred step was to move forward with the disaccharide 7-25 leaving the Xyl C-2 position unprotected. Removal of anomeric —OBz group at the reducing end of 7-25 with NH₃-gas and successive treatment with trichloroacetonitrile and DBU gave disaccharide-TCA donor 7-30 in overall 75% yield. The glycosylation with linker 7-31 was performed with catalytic TMSOTf to afford 7-32 in 83% yield (Scheme 2.215), Scheme 2.2.1.5 Synthesis of disaccharide donor 7-32 and glysolyation with linker

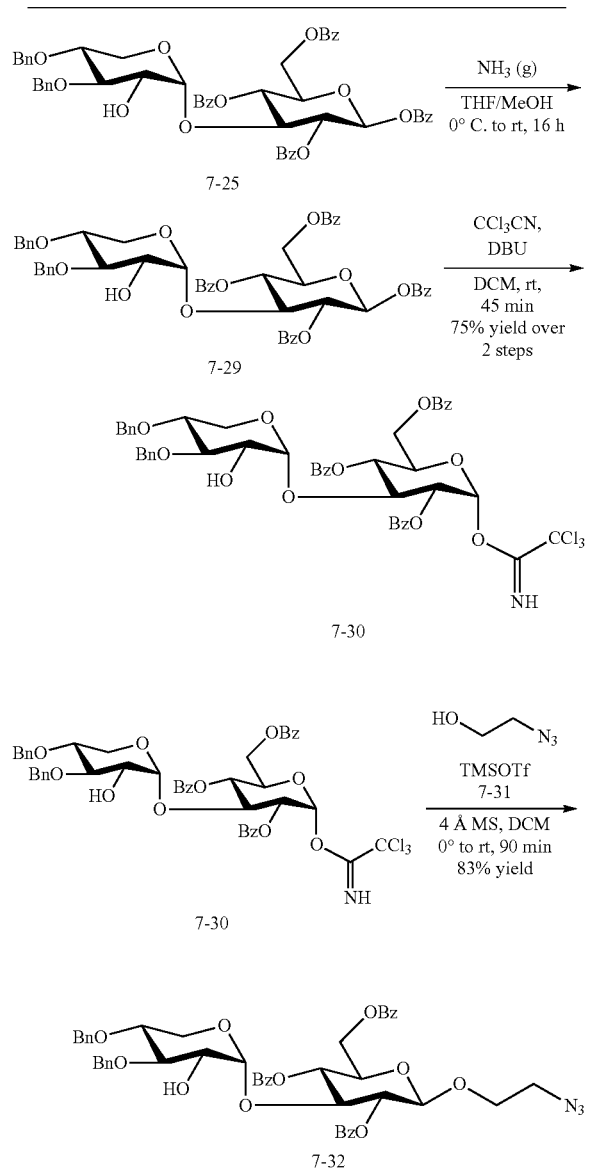

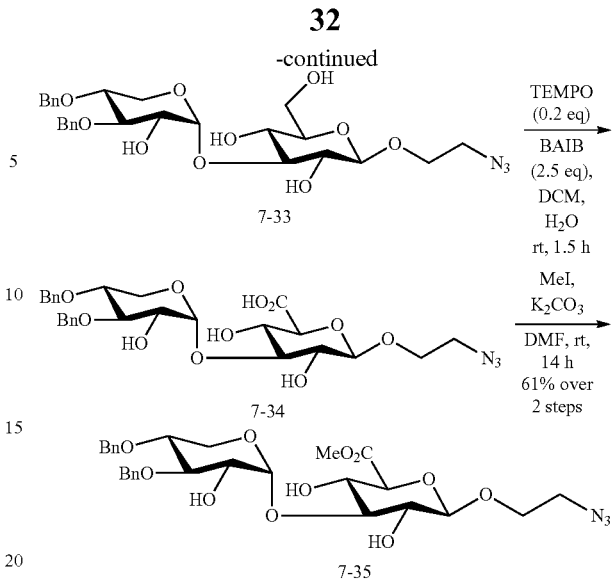

The linker-disaccharide 7-32 was then de-benzoylated in high yield and selective C-6 oxidation of Glc was carried out following the reported method with TEMPO and BAIB.[30] Immediate protection of carboxylic acid with methyl ester gave Xyl-GlcA disaccharide 7-35 in 61% yield (Scheme 2.2.1.6).

Scheme 2.2.1.6 Late stage C-6 oxidation of semi-protected disaccharide 7-33

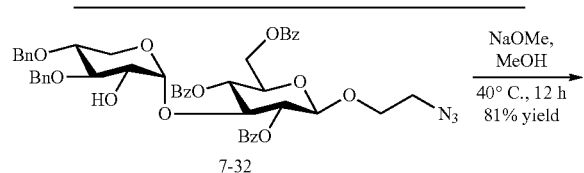

The deprotection of the benzyl group in 7-35 went smoothly under hydrogenolysis conditions to give disaccharide 7-36 with amine linker, Unfortunately, the next ester hydrolysis step was not successful. Even with the change in the order of the deprotection sequence the target final disaccharide 7-37 was not obtained (Scheme 2.2.1.7).

Scheme 2.2.1.7 Failed deprotection sequence to obtain disaccharide

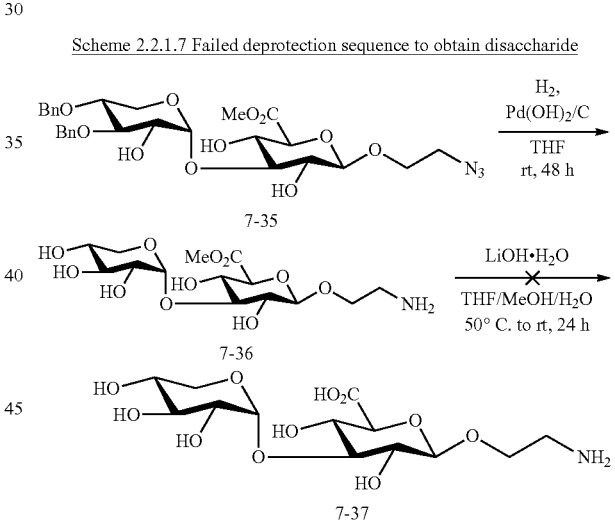

It was rationalized according to the present disclosure that the presence of free amine in the linker made the handling of the disaccharide problematic. Moreover, for successful oligomerization of the repeating unit a C-3 unprotected Xyl in the non-reducing end is essential and that calls for a differentially protected Xyl unit in the disaccharide motif as well.

2.2.2 Post-Glycosylation Oxidation Strategy: Generation II

The difficulty in obtaining the desired final disaccharide in Gen I method ensued from the hydrogenolytic reduction of azide and hence it was preferable according to the present disclosure to modify the disaccharide motif 7-25 accordingly. The Glc unit didn't need further modification. Also preferably, the Xyl C-4 is protected with —OBz group to maintain the uniformity of protecting groups to facilitate a one-step global deprotection. The desired disaccharide acceptor 7-39 must have Xyl C-3 position unprotected for glycosylation. On the other hand, the modified disaccharide donor 7-38 must possess a temporary protecting group on C-3 Xyl that can be removed easily after successive glycosylation to quickly obtain higher-order (tetra) glycosyl acceptor. Previous experiments showed that C-2 Xyl is hard to access and glycosylation can be performed leaving that position protecting group free. As a corollary, it is expected that a disaccharide acceptor 7-39 with a 2,3-hydroxyl Xyl ($R_1$=H) motif should undergo glycosylation in a regioselective manner with preferential C-3 position. Aforementioned criteria for designing the substrates opened a new possibility of a singular multitasking disaccharide building block that can quickly be converted into disaccharide donor and acceptor. According to the present disclosure, it is preferable to protect both C-2 and C-3 Xyl with isopropylidene group that can be easily removed in mild acidic condition and get exposed for subsequent glycosylation. Compound 7-40 has been designed to minimize the effort required to synthesize the disaccharide donor and possibly eliminate one deprotection step. (FIG. 11).

The synthesis of 7-46 was described in Scheme 2.2.2.1. The disaccharide was first modified by removing benzyl groups by a hydrogenolysis process. An isopropylidene group was successfully installed on C-2 and C-3 Xyl in 61% yield over 2 steps. The reason for the moderate yield can be explained by restricted access to the C-2 position. Also, isopropylidene group is less bulky compared to benzoyl moiety and hence worked better in protecting Xyl C-2 position. Compound 7-43 was then benzoylated and anomeric hydrolysis was performed with $NH_3$-gas. Installation of TCA gave modified disaccharide donor 7-46 in 60% yield (Scheme 2.2.2.1).

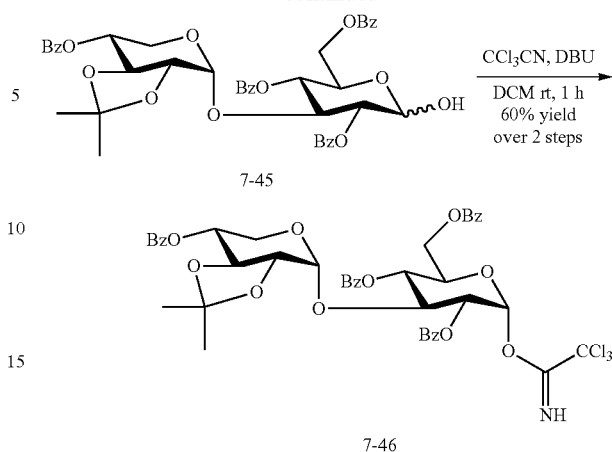

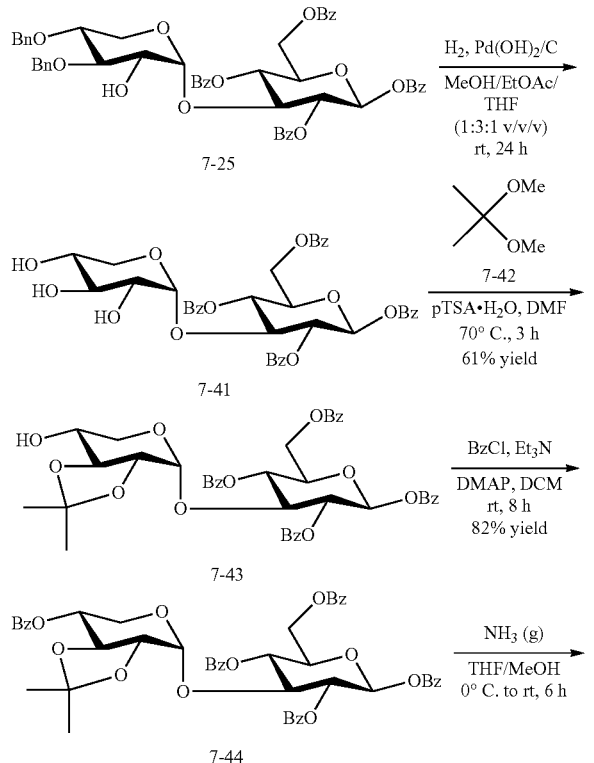

Glycosyl donor 7-46 was then tested for glycosylation with azido-linker 7-31 under TMSOTf activation. Somewhat unexpectedly, it was found that under Lewis acid TMSOTf the glycosylation was accomplished and the isopropylidene group fell off in situ to give disaccharide 7-47 with C-2,3-di-OH Xyl, which is ready to be used as a glycosyl acceptor for oligomerization. Thus, in one step a glycosylation and a deprotection process (Scheme 2.2.2.2) was accomplished to afford the disaccharide in 80% yield.

Scheme 2.2.2.2 One-step glycosylation and deprotection process

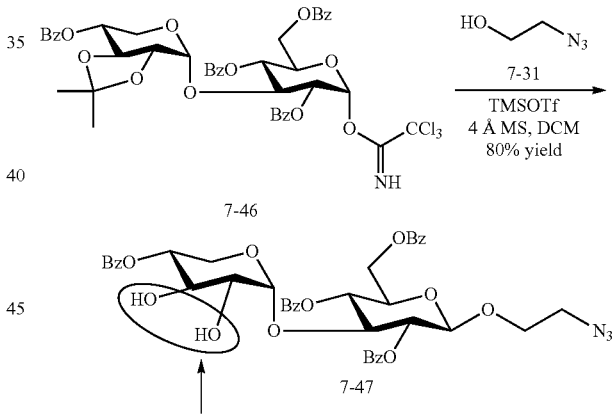

Due to the acidity of the medium, Isopropylidene protecting group fell off after glycosylation and the product is ready to be used as acceptor for further glycosylation.

To achieve the target disaccharide, compound 7-47 was globally de-benzoylated in presence of NaOH in MeOH/THF/$H_2O$ mixture. The per-hydroxyl disaccharide 7-48 was subjected to TEMPO-BAIB mediated selective C-6 oxidation and failed to produce the desired disaccharide. A careful observation of the reaction mixture helped to identify the problem in solubility of the final product in DCM/$H_2O$ mixture. An alternative oxidation strategy employing catalytic TEMPO and NaOCl in water was adopted.[31] The pH of the reaction mixture was carefully monitored under 10 by dropwise addition of 0.5 N NaOH solution and the final disaccharide 7-49 was obtained after purification by P-2 gel filtration (Scheme 2.2.2.3).

Scheme 2.2.2.3 Late stage C-6 oxidation of disaccharide and addressing the solubility issue

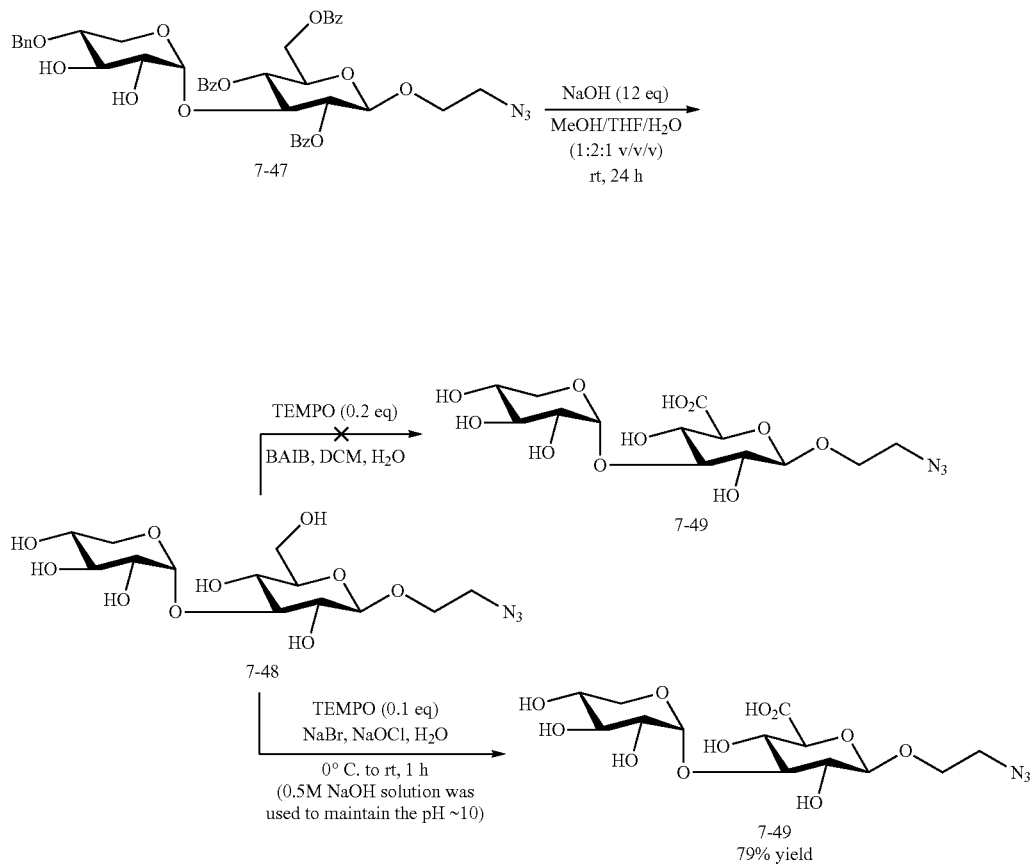

Under the present disclosure, a convenient disaccharide motif 7-44 has been established which can quickly be converted to donor and acceptor. The glycosylation of disaccharide donor 7-46 with azido-linker gave the product 7-47, which is well poised to be tested for C-3 regioselective glycosylation. The glycosylation involving 7-46 and 7-47 was performed with catalytic TMSOTf in DCM. The glycosylation was operated in exclusive regioselective manner. In most occasion the isopropylidene group fell off from product tetrasaccharide and if not a treatment with Dowex H+ resin in MeOH would help to obtain tetrasaccharide 7-50 with repeating Xyl-α-(1→3)-Glc unit (Scheme 2.2.2.4) in 54% (79% brsm) yield.

Scheme 2.2.2.4 Synthesis of protected tetrasaccharide

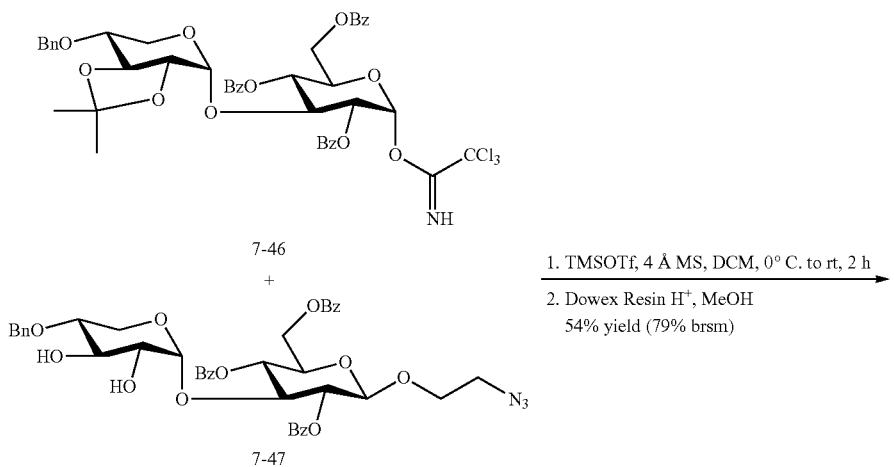

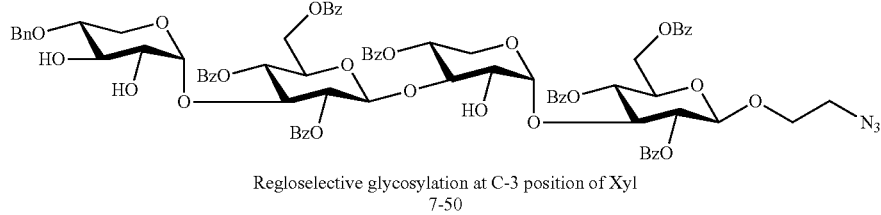
Regioselective glycosylation at C-3 position of Xyl
7-50
The protected tetrasaccharide was globally de-benzoylated using 20 eq. of NaOH to obtain per-hydroxy tetrasaccharide 7-51. The attempts for simultaneous oxidation at two Glc C-6 positions under TEMPO-NaOCl conditions failed (Scheme 2.2.2.5).
Scheme 2.2.2.5 Global deprotection and failed late-stage oxidation of tetrasaccharide
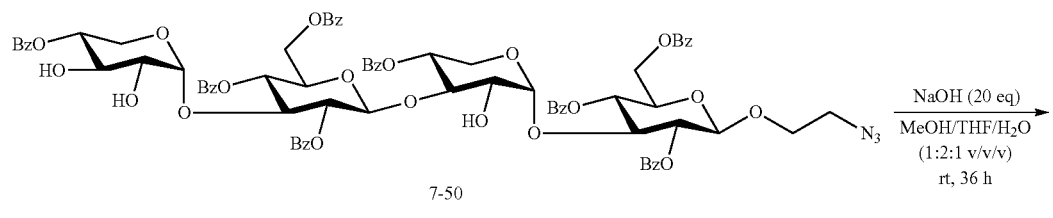
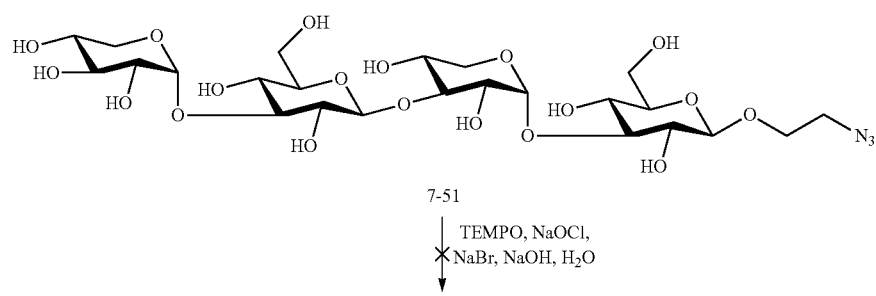
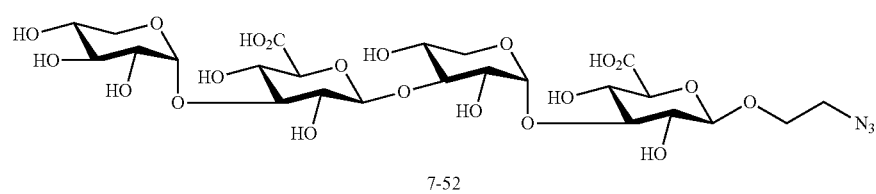

A few alternative TEMPO-mediated methods for selective oxidation were tried and none of them produced the desired tetrasaccharide (Table 2.2.2.1).

TABLE 2.2.2.1

Attempts for late stage oxidation on tetrasaccharide

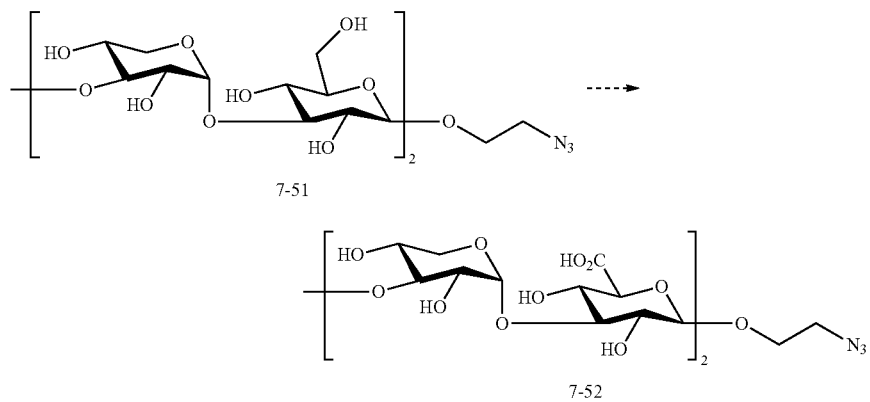

7-51

7-52

| Entry | Reagents | Condition |
|---|---|---|
| 1 | 0.3 eq TEMPO, 1.2 eq NaBr, 5 eq NaOCl, water, few drops of NaOH soln. | Addition of NaOCl @ 0° C., 90 min @ same temp. Stirred at rt for 18 h. |
| 2 | 3 eq TEMPO, 2 eq NaBr, 4 eq NaOCl, water, 1 mL 5% $NaHCO_3$ soln. | Addition of NaOCl @ 0° C. and then stirred for 15 min. |
| 3 | 0.1 eq TEMPO, 0.7 eq NaBr, 13% w/v NaOCl (adjusted to pH 10 by 4M HCl), water, 1M NaOH soln. | Reaction was performed at room temperature and pH of the mixture was strictlly maintained ~10. |

Interestingly, most of the literature reported[32] to use the similar oxidation strategy for higher-order oligosaccharides have either completely or partially protected the sugar backbone leaving primary hydroxyl unprotected for oxidation. Attempts have been made for selective oxidation of multiple primary hydroxyl groups in completely unprotected oligosaccharides and was not very promising.[33] Natural polysaccharides can be selectively oxidized in the presence of TEMPO at pH>10 with serious consequences like cleavage of glycosyl linkages, β-elimination, and depolymerization.[34] According to the present disclosure, the TEMPO oxidation procedure was tested on a partially protected tetrasaccharide 7-53. The reaction afforded a tetrasaccharide 7-54 with one primary hydroxyl group oxidized, presumably the one (in bold letter) on the Glc that is α-linked with 3,4-di-O-Bn Xyl. Prolonged reaction time didn't yield any di-carboxylated product. An unhindered, stable nitroxyl radical 9-azabicyclo[3.3.1]nonane N-oxyl (ABNO), which is reported[35] to be highly active in nature compared with TEMPO in the catalytic oxidation, was used on substrate 7-53 and similar mono-carboxylated tetrasaccharide 7-54 was obtained (Scheme 2.2.2.6).

Scheme 2.2.2.6 Trial oxidation of partially protected tetrasaccharide

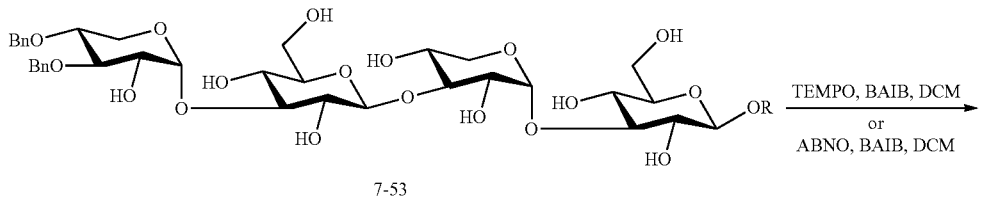

7-53

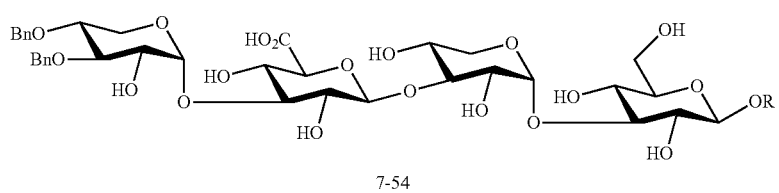

7-54

The failed oxidation strategy made it evident that the late stage manipulation of oligosaccharides is in general very critical. Moreover, the scarcity of advance intermediate oligosaccharide in large quantity for optimization of reaction conditions poses another hurdle on post-glycosylation oxidation strategy. That being stated, it is preferable according to the present disclosure to pursue the pre-glycosylation oxidation strategy to synthesize LARGE-glycan.

2.2.3 Preglycosylation-Oxidation Strategy: Generation III

In a preglycosylationoxidation approach (FIG. 8), the oligosaccharide is prepared using uronic acid building blocks. The uronic acid building blocks are synthesized from the monosaccharide glycosyl precursors. Very often the uronic acids are considered to be unreactive glycosyl donors compared to their reduced form.[36] The presence of the electron-withdrawing C-5 carboxylic acid moiety is responsible for this 'disarm' effect. D-Glucuronic acid is a prime constituent of many biologically relevant oligosaccharides.[37] Glycosaminoglycans (GAGs) contains D-glucuronic acid, which gives the biologically active polysaccharide an anionic character. Despite their reduced reactivity, an appropriately activated glucuronosyl donor undergoes efficient glycosylation. No significant loss in reactivity of GlcA was observed when introduced as a glucuronosyl acceptor. Less critical backbone manipulations at advanced stages and lack of complex late stage oxidation made the preglycosylation-oxidation a robust strategy for synthesis of GlcA containing oligosaccharides.[38]

For the preglycosylation-oxidation strategy, the unique disaccharide 7-44 needed to be modified with glucuronic acid in place of glucose. It is preferable under the present disclosure to keep the protecting groups on C-2 and C-3 the same as before (Formula 2.2.3.1). The modified Xyl-GlcA disaccharide 7-55 can be synthesized using the GlcA 7-56 building block.

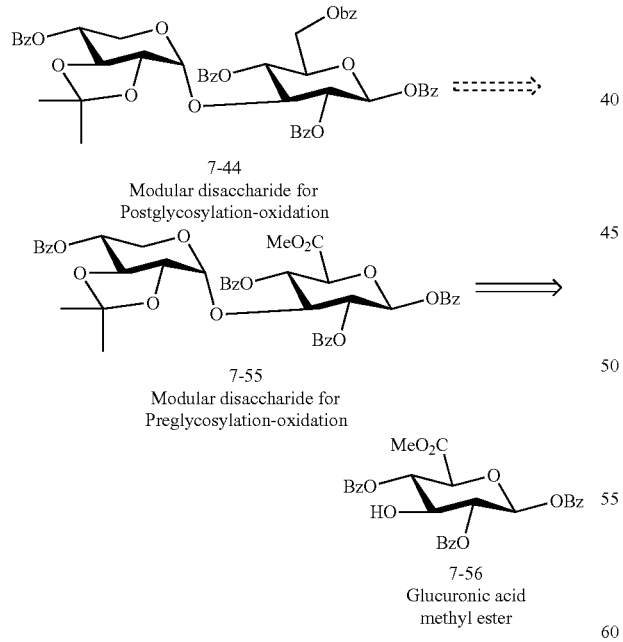

Formula 2.2.3.1 Design for Modular Disaccharide in Preglycosylation Oxidation

The primary hydroxyl group of 3-O-Bn glucopyranoside 7-22 was selectively protected by TIPSCl in presence of imidazole and solvent DMF. Consecutive benzoylation using benzoyl chloride and catalytic DMAP gave compound 7-58 which was treated with a solution of hydrogen chloride at low temperature to afford 7-59 in overall 82% yield. The primary OH was then subjected to Jones oxidation followed by methyl ester formation to give GlcA ester 7-61 in 52% yield over 2 steps. 3-O-Benzyl protecting group was removed under $H_2$-balloon with $Pd(OH)_2/C$ catalyst in THF to achieve GlcA building block 7-56 in 94% yield (Scheme 2.2.3.1).

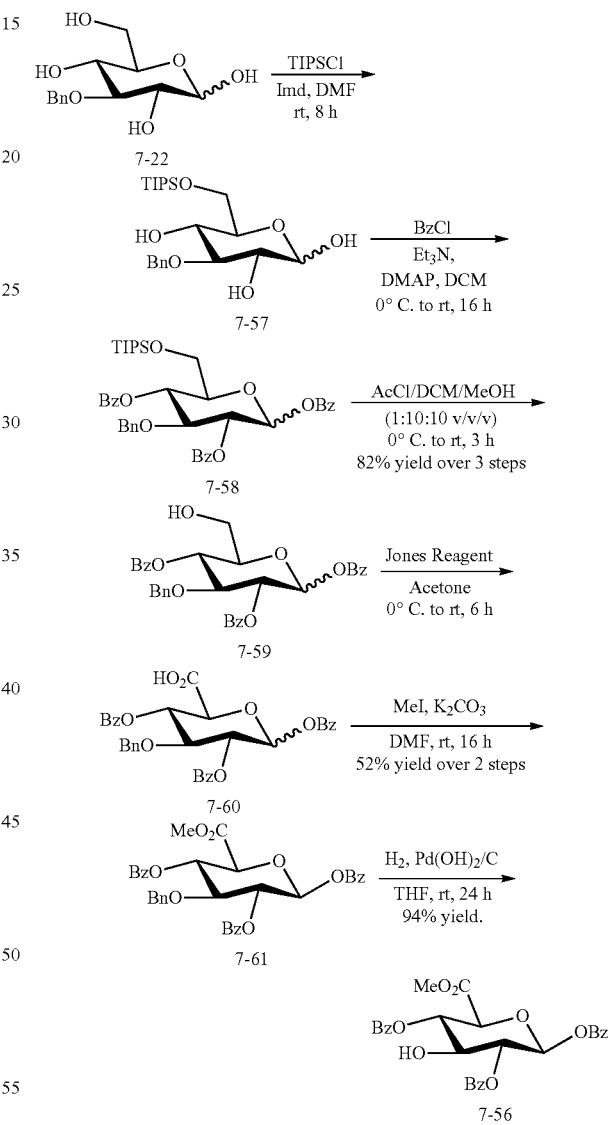

With the GlcA building block in hand, the modular disaccharide 7-55 was synthesized. Xyl donor 7-10 and the GlcA 7-56 were introduced into the newly developed IAD method of the present disclosure to obtain the 1,2-cis-disaccharide 7-63. The product disaccharide 7-63 and the acceptor 7-56 had very similar $R_f$ values and hence were very hard to separate in column chromatography, especially in large scale. Under the present disclosure, the mixed acetal (7-62, 81% yield) was isolated and then treated it with BAHA in acetonitrile to obtain the disaccharide 7-63 which was then immediately debenzylated via hydrogenolysis. After column chromatography disaccharide 7-64 was obtained in overall 48% yield. Xyl C-2 and C-3 were protected with isopropylidene and C-4 position was capped with benzoyl chloride (7-55, 68% yield). Anomeric hydrolysis with $NH_3$-gas and installation of TCA group gave Xyl-α-(1→3)-GlcA disaccharide donor 7-67 in 58% yield (Scheme 2.2.3.2).

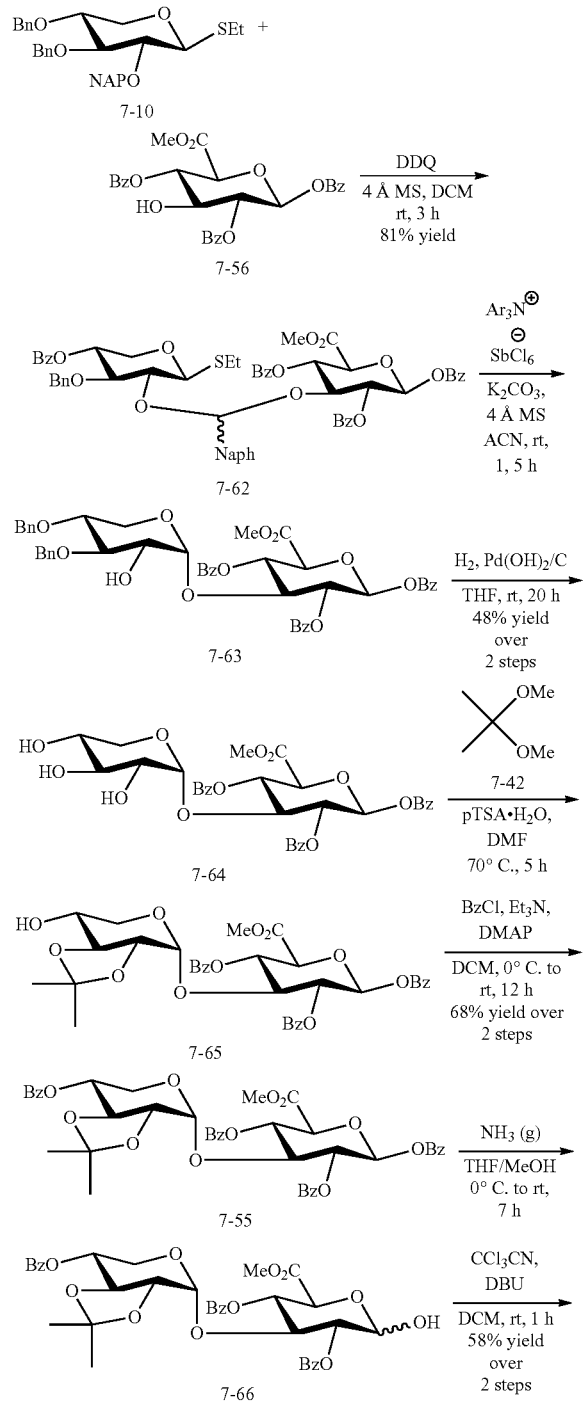

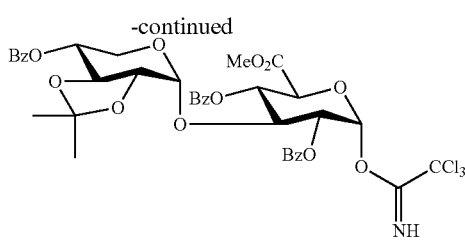

The donor 7-67 was activated with catalytic amounts of TMSOTf and reacted with the 2-azidoethanol linker 7-31. The yield for this reaction was not as high as the similar reduced disaccharide 7-46, yet the 63% yield was acceptable considering the one-step glycosylation and isopropylidene removal process. The final global deprotection of the benzoate ester protecting group and hydrolysis of methyl ester was carried out in aqueous methanolic solvent with more than 10 eq. of 4 N NaOH solution. The reaction was continued for 24 h and then quenched with 1 N HCl solution. Purification by Biogel P-2 filtration and successive lyophilization gave final disaccharide 7-49 in 77% yield (Scheme 2.2.3.3).

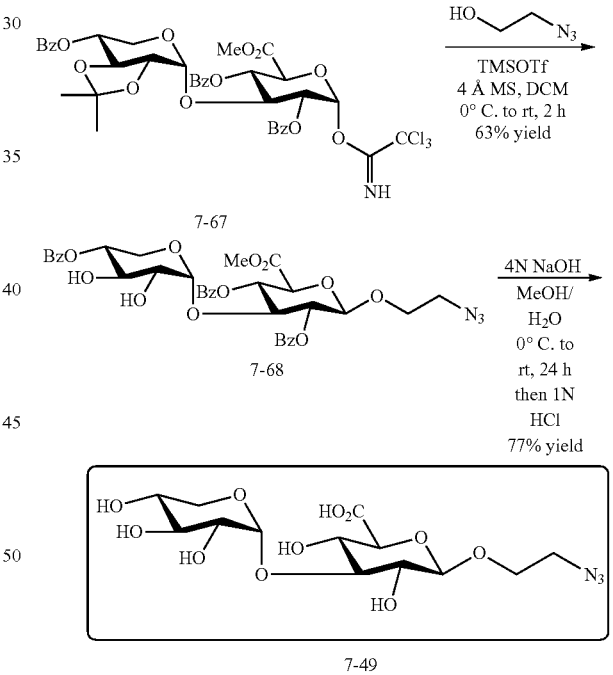

The disaccharide intermediate 7-68 from Scheme 7.2.3.3 was preferably utilized as a glycosyl acceptor in tetrasaccharide synthesis. Considering the previous results, it was expected, under the present disclosure, to achieve regioselective C-3 glycosylation albeit in presence of an unprotected C-2 hydroxyl group. Disaccharide donor 7-67 and acceptor 7-68 were mixed together and coevaporated with toluene twice. The use of molecular sieves proved to be dampening the rate of glycosylation and significant formation of orthoester byproduct was observed. The mixture was treated with with catalytic amounts of TMSOTf in anhydrous DCM and after 2 h the crude mixture was treated with Dowex H⁺ resin for 8 h to obtain tetrasaccharide 7-69 in 48% yield. The acceptor was not fully consumed during the reaction time and can be recovered. The yield was calculated to be 79% based on recovered starting material. Global deprotection was performed with 4 N NaOH to achieve the final tetrasaccharide 7-52 after purification of crude residue by P-2 gel filtration (61% yield) (Scheme 2.2.3.4).

Scheme 2.2.3.4 Synthesis of final tetrasaccharide

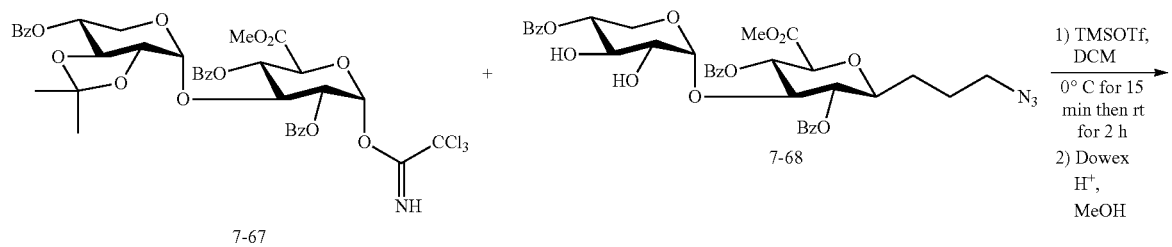

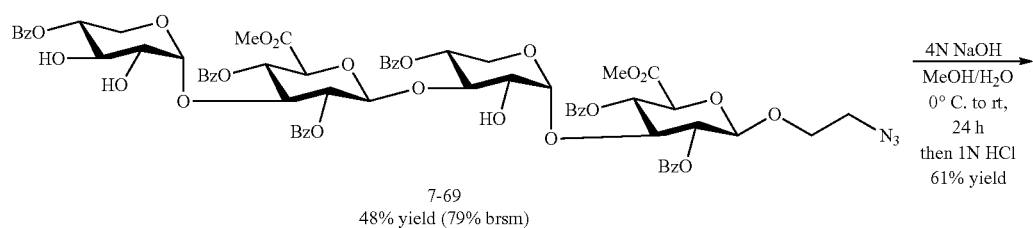

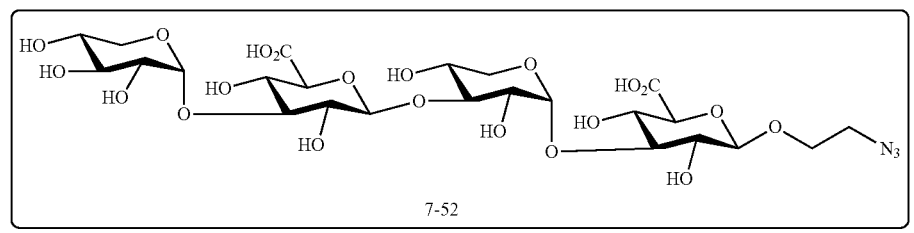

In a similar manner, the hexasaccharide was preferably synthesized by glycosylating disaccharide donor 7-67 and tetrasaccharide acceptor 7-69 under TMSOTf condition. The C-3 selective glycosylation proceeded smoothly and after 2 hour at room temperature a mixture of two products 7-70 and 7-71 were obtained. With the higher-order oligosaccharide, the 0.2 eq. of TMSOTf failed to remove the isopropylidene group after accomplishing the glycosylation. The crude mixture was then treated with Dowex H⁺ resin to completely remove the isopropylidene group and protected hexasaccharide 7-71 was obtained in 32% overall yield (71% brsm). The remaining protecting groups were successfully removed by 4 N NaOH solution to afford the final hexasaccharide 7-72 in 58% yield (Scheme 2.2.3.5).

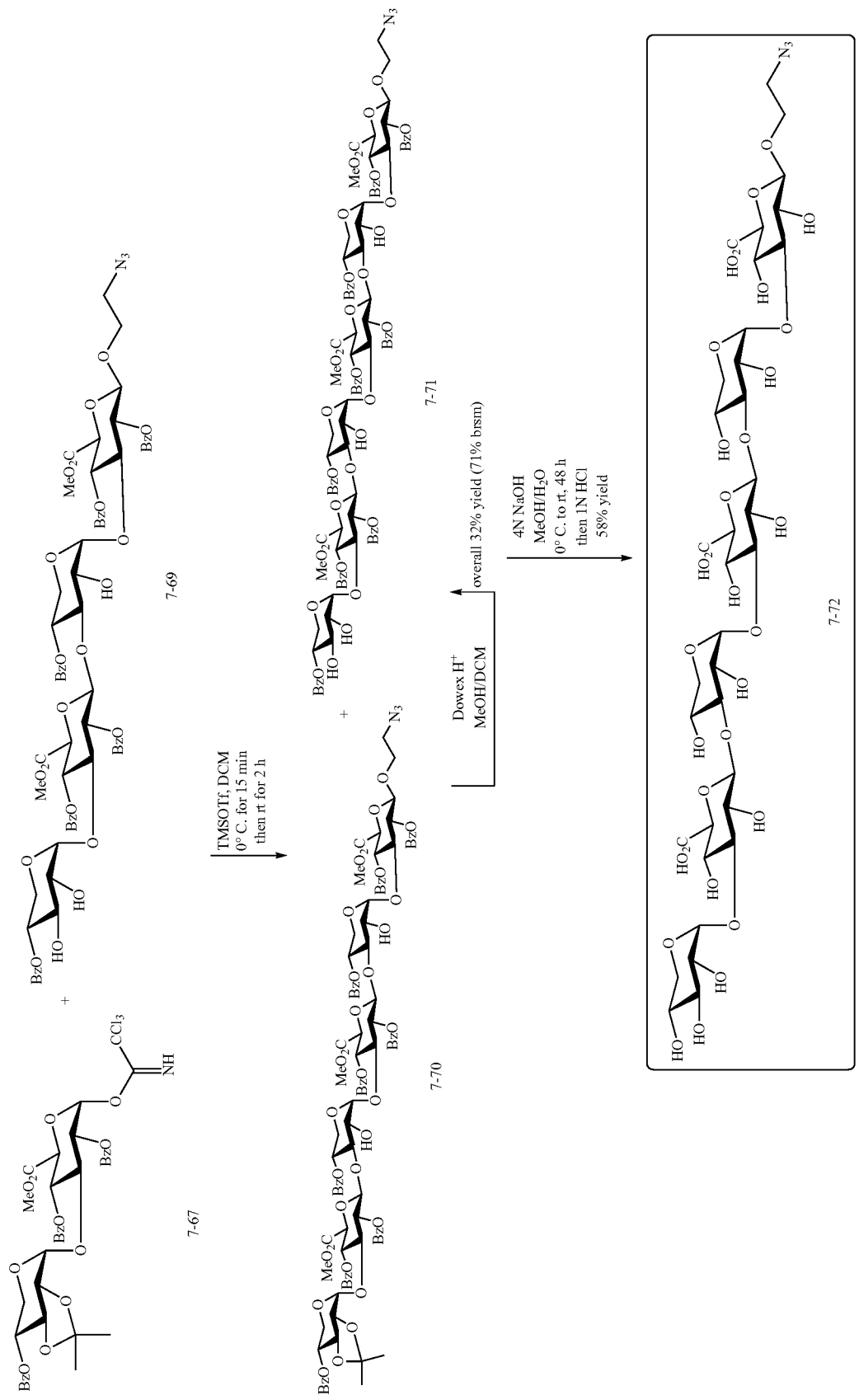

Successfully synthesized according to the present disclosure were a series of di-, tetra-, and hexa-saccharide LARGE glycans employing a preferred C-2 NAP mediated one-pot redox 1,2-cis glycosylation method. An advanced modular disaccharide Xyl-α-(1→3)-GlcA building block was designed and synthesized which can quickly be modified to glycosyl donor and acceptor for oligosaccharide synthesis. This design saved many steps of protection-deprotection sequences for the Xyl moiety. The isopropylidene protecting group proved to be suitable for the one-step protection deprotection sequence. Interestingly, the deprotection sequence occurred in situ after the glycosylation was completed not before the glycosylation. Our successful total synthesis of LARGE glycans gave each of the oligosaccharides in 10 mg scale. The repeating α- and β-connectivity in oligosaccharides were confirmed by 2-D NMR analysis. The $^{1}$H-$^{13}$C coupling constant obtained from proton coupled-HSQC NMR confirmed the connectivity of monosaccharides in the synthesized oligosaccharides. Access to different LARGE-glycan will help the detail study of CMDs by assessing the size, exact binding site and formation pathway of specific glycan. The present disclosure is expected to serve as the basis for finding novel medical solutions to neurological diseases that commonly causes cardiac muscle dystrophies and brain diseases.

3.0 Synthesis of B4GAT1-Glycan Trisaccharide

α-dystroglycan is the only well-established O-mannoslyated mammalian protein, which is the central component of the dystrophin-glycoprotein complex (DGC).[1b, 6a] In 2012, Campbell et. al, discovered the LARGE enzyme for postphosphorosyl modification of mannose on α-DG. The other contributing glycans in the linker between Man-O-phosphate and LARGE glycans and the associated enzymes are not completely known. In 2014, Cambell and Wells separately reported the GlcA as the acceptor sugar for LARGE polymer initiation and the priming enzyme B4GAT1, a glucuronyltransferase that contributes to production of the post-phosphoryl glycan linker by transferring a GlcA residue onto a β-Xyl acceptor.[10b, 39] The enzyme B4GAT1, which was wrongly described[40] as B3GNT1 belongs to a Carbohydrate-Active Enzymes database (CaZY) family; interestingly one shared with LARGE and LARGE2 (FIG. 12).

3.1 Structure and Retrosynthesis of Trisaccharide

The bi-functional LARGE enzyme harbors a xylopyranoside β-1,3 glucuronyltransferase B3GAT in its domain whereas the enzyme B4GAT1 transfers GlcA on Xyl in a β-1,4 fashion. The glycan linker, containing phospho-ribitol and a Xyl moiety (transferred by TMEM5 enzyme) is primed for B4GAT1 and LARGE dependent glycosylation (FIG. 12).[41] The essential GlcA-β-(1→4)-Xyl connectivity transferred by B4GAT1 is significantly different from the GlcA-β-(1→3)-Xyl connectivity transferred by the B3GAT domain in LARGE. From a synthetic perspective, it is crucial to address the structure of the trisaccharide motif, which demonstrates the donor and acceptor capability of GlcA (FIG. 13).

Under the present disclosure, a disconnection of trisaccharide motif 8-1 is preferred starting with the cleavage of important GlcA-β-(1→4)-Xyl bond. A C-4 hydroxyl Xyl building block 8-2 was identified as a glycosyl acceptor along with the disaccharide donor 8-3. Preferably, the disaccharide donor 7-67 is used that was previously synthesized via newly developed one-pot IAD of the present disclosure in our effort to obtain LARGE-glycans (FIG. 14), Given the success in preglycosylation-oxidation strategy of the present disclosure, it was preferable to synthesize the target trisaccharide sequence 8-1.

3.2 Forward Synthesis:

The forward synthesis of (x) required a 4-OH Xyl building block to be used as an acceptor. A list of 4-OH-Xyl can be quickly synthesized from intermediates prepared before. The Xyl building blocks would be then tested for glycosylation with disaccharide donor 7-67 to obtain the desired trisaccharide. 2-azidoethanol 7-31 was preferably used as the linker at the reducing end of the trisaccharide to keep the B4GAT1 glycan consistent with previously synthesized LARGE glycans.

3.2.1 C-2,3-Di-OBz Xylose Acceptor

First, 2,3-di-OBz Xyl was preferably considered attached with an azido-linker as the glycosyl acceptor. To obtain the building block the previously synthesized Xyl intermediate 7-19 was preferably used and protected C-2 position with —OBz group. The 3,4-di-OBn groups were removed under hydrogenolytic condition to obtained 8-5 in 88% yield. The C-4 position of Xyl was then selectively silylated with bulky TBSCl at 10° C. to give the monosilylated product 8-6 in 67% yield. C-3 was then protected with —OBz group and then the thioglycoside was activated under NIS/TMSOTf condition to attach linker 7-31 in 89% yield. The silylgroup was removed with in situ generated hydrogen chloride to afford 2,3-di-OBz xylopyranoside 8-9 in 95% yield (Scheme 3.2.1.1).

Scheme 3.2.1.1 Synthesis of C-2,3-di-OBz Xylose acceptor

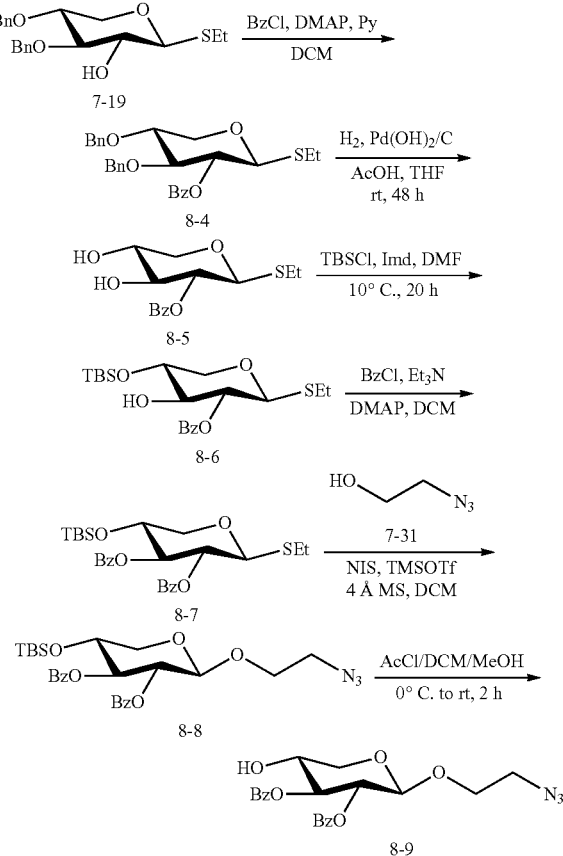

The acceptor 8-9 was then taken for glycosylation with disaccharide donor 7-67. The donor was activated with TMSOTf in DCM with 4 Å molecular sieves. After 2 h, most of the donor was consumed but there was no sign of consumption of the acceptor at all. The acceptor was recovered completely and the donor was found to be hydrolyzed. The presence of electron withdrawing —OBz groups on 8-9 made it less reactive. The donor-acceptor reactivity mismatch played a crucial role in this unsuccessful attempt (Scheme 3.2.1.2).

Scheme 3.2.1.2 Failed attempted glycosylation with acceptor 8-9

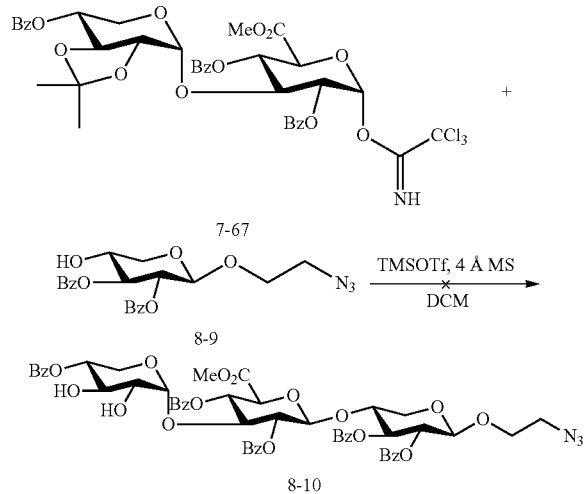

3.2.2 C-2,3-Isopropylidene Xylose Acceptor

Isopropylidene group is less electron withdrawing compared to —OBz groups. Under the present disclosure the excellent maneuver with isopropylidene group in a Lewis acid mediated glycosylation was previously demonstrated where the protecting group was spontaneously removed. Applying the same concept, it was preferable to synthesize 2,3-O-isopropylidene Xyl acceptor 8-15 for glycosylation. Per-acetyl D-xylose 7-13 was activated in presence of BF$_3$·Et$_2$O and reacted with azido-linker 7-31 to afford compound 8-11. Subsequent deacetylation gave 8-12 in 78% yield. The protection of C-2 and C-3 with isopropylidene in presence of 2-methoxypropene and TFA in DMF gave target product 8-15 mixed with Xyl having additional degree of acetal protection on the C-4 position 8-14. Treatment of 8-14 with trace amount of p.TSA·H$_2$O in MeOH at 0° C. for 15 min selectively deprotected the C-4 acetal leaving 2,3-acetonide protection unharmed. The overall yield for 8-15 was 82% (Scheme 3.2.2.1).

Scheme 3.2.2.1 Synthesis of 2,3-O-isopropylidene Xylose acceptor

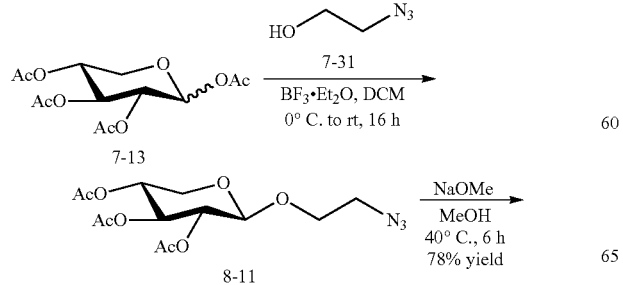

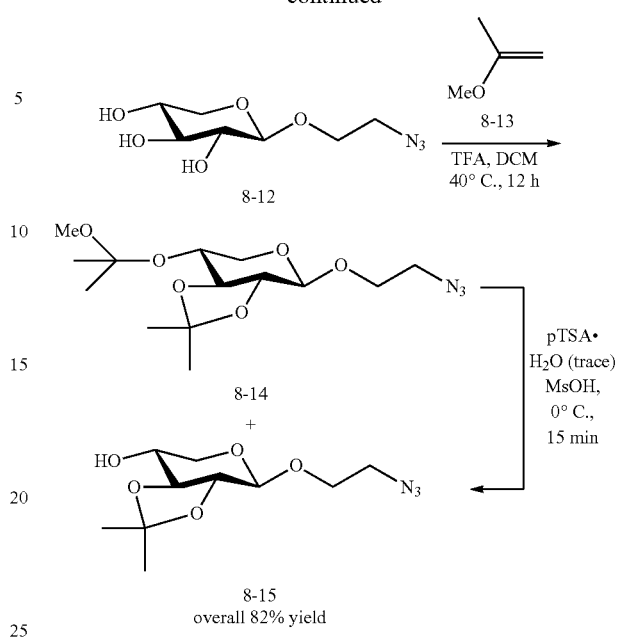

The acetonide protected acceptor 8-15 was subjected to glycosylation with donor 7-67 in presence of TMSOTf. The reaction yielded the desired trisaccharide 8-16 in very low yield (~10%). Most of the donor (54%) was hydrolyzed and acetonide from both donor and acceptor fell off during the reaction (Scheme 3.2.2.2a). Among multiple spots on TLC, the deprotected acceptor was also identified. The observations suggested that controlling the reactivity of isopropylidene groups both on the donor and acceptor simultaneously were troublesome.

Scheme 3.2.2.2 Failed glycosylation with 2,3-O-isopropylidene Xyl acceptor 8-15 a)

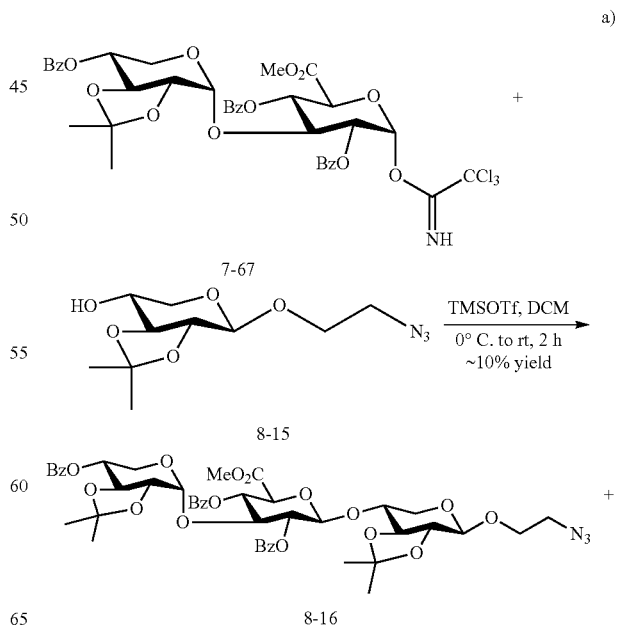

53

-continued

Acetonide deprotected trisaccharide (mixed regioisomer)

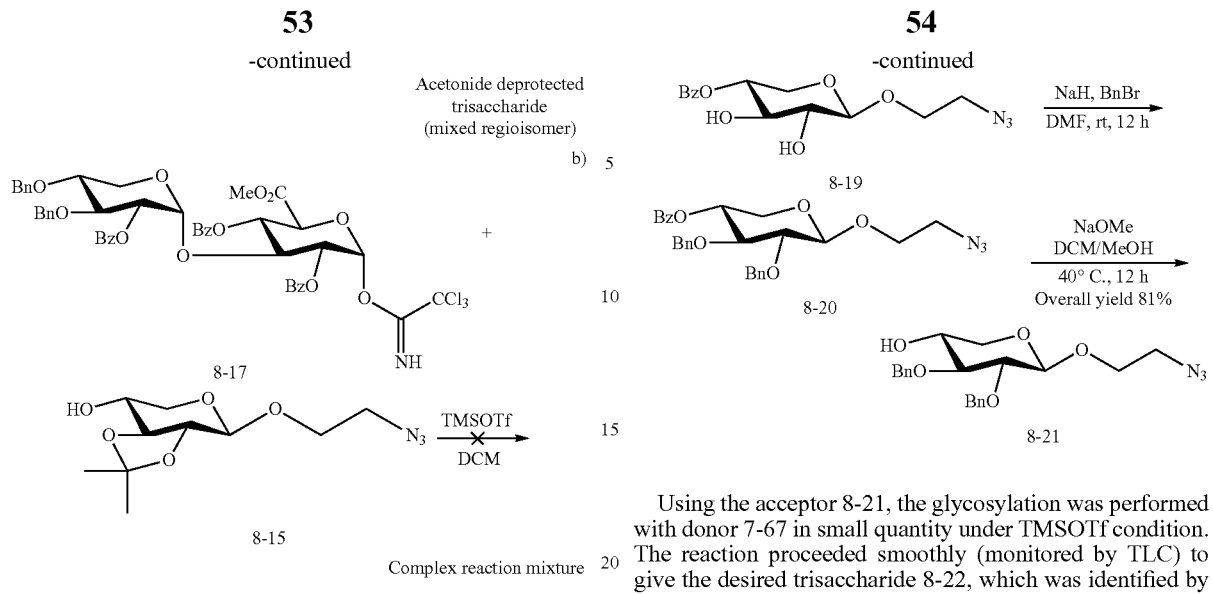

To reduce the chances of removal of isopropylidene from donor 7-67 a modified disaccharide donor 8-17 was used. 8-17 can be readily prepared following Scheme 8.2.3.3. It is important to mention that the —OBz protection at C-2 Xyl position of donor 8-17 was very sluggish. The disaccharide donor 8-17 was then employed for glycosylation with acceptor 8-15, Reaction under TMSOTf condition showed multiple spots on TLC (Scheme 8.2.2.2b), It is postulated that the donor-acceptor reactivity mismatch and incompetence of isopropylidene protected Xyl acceptor in TMSOTf condition made the reaction mixture complex.

3.2.3 Successful Synthesis with 2,3-Di-OBn Xylose Acceptor

Under the present disclosure, the reactivity matching of the donor and acceptor is important in successful glycosylation. Preferably, electron donating protecting groups are introduced on the Xyl acceptor to increase the nucleophilicity of the secondary hydroxyl group, 2,3-di-OBn Xyl acceptor 8-21 is preferred here under the present disclosure. To get a quick access to acceptor 8-21, previously synthesized compound 8-15 was benzoylated at C-4 position to obtain 8-18, Next, the isopropylidene group was removed by treating it with 0.5 eq. of pTSA·H$_2$O in MeOH/DCM mixture to afford 8-19 in 92% overall yield. Subsequent dibenzylation of 8-19 followed by removal of —OBz by catalytic amount of NaOMe in MeOH afforded Xyl acceptor 8-21 in overall 81% yield (Scheme 3.2.3.1).

Scheme 3.2.3.1 Synthesis of C-2, 3-di-OBn Xylose acceptor

54

-continued

Using the acceptor 8-21, the glycosylation was performed with donor 7-67 in small quantity under TMSOTf condition. The reaction proceeded smoothly (monitored by TLC) to give the desired trisaccharide 8-22, which was identified by LCMS (Scheme 3.2.3.2), Scheme 3.2.3.2 Synthesis of trisaccharide with donor 7-67

Identified by LCMS
8-22

On planning to scale up the glycosylation (Scheme 3.2.3.2), the structures of the donor and acceptor became conspicuous. Because of the presence of —OBn protecting groups on acceptor 8-21, there was flexibility to replace the donor 7-67 which contained —OBn protecting group on Xyl moiety. In either case, it was required to debenzylate the trisaccharide to obtain final trisaccharide 8-27. The biggest advantage of adopting the donor 8-17 is that it can be synthesized from a common precursor of donor 7-67. The method would save at least 4 steps of protection-deprotection sequences. Precursor 7-63 was subjected to DMAP catalyzed benzoylation using BzCl in DCM. From previous experience under the present disclosure, it was learned that C-2 protection of Xyl moiety of analogous building block 7-25 was very sluggish. Under DMAP and Et$_3$N condition 7-63 gave 8-23 in 51% yield after 48 h. The starting material 7-63 was recovered and subjected to another round of benzoylation to obtain 87% combined yield. Compound was then treated with NH$_3$ gas and subsequent TCA installation gave the donor 8-17 in 64% overall yield (Scheme 3.2.3.3).

Scheme 3.2.3.3 Synthesis of disaccharide donor 8-17 from precursor 7-63

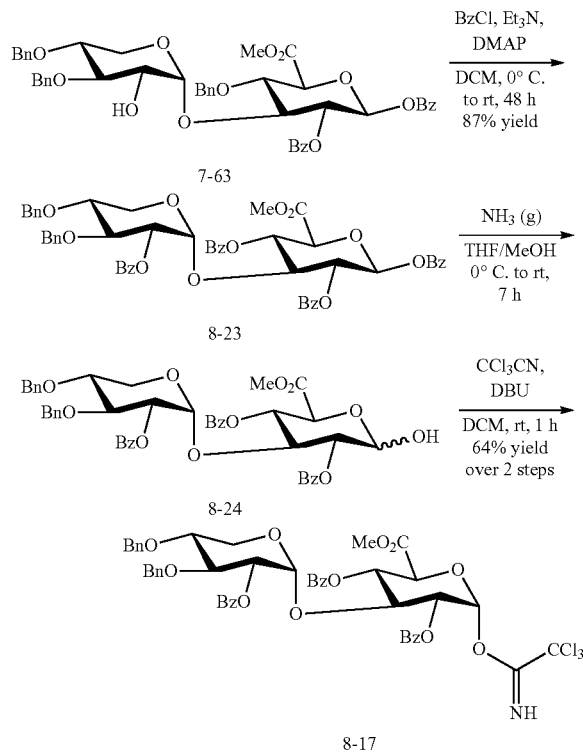

The donor 8-17 and the acceptor 8-21 was then combined and coevaporated with toluene and dissolved in anhydrous DCM, and was added 4 Å molecular sieves. The catalyst TMSOTf (0.15 eq) was added at 0° C. and further stirred at rt for 1 h 15 min to obtain trisaccharide 8-25 in 63% yield (Scheme 3.2.3.4).

Scheme 3.2.3.4 Synthesis of trisaccharide 8-25

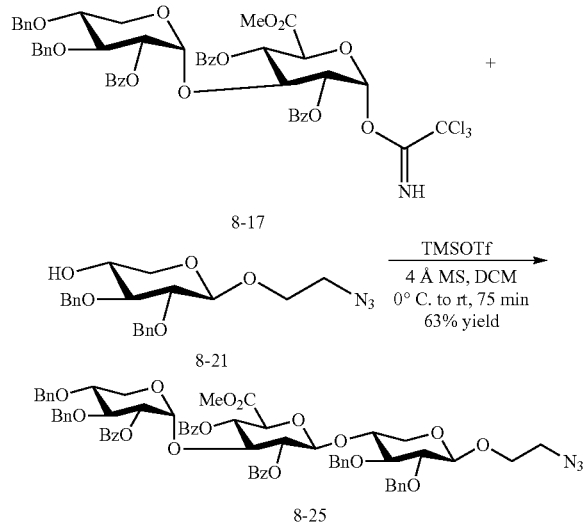

To obtain the final trisaccharide, the removal of protecting groups is the only step left. Earlier problems occurred involving final deprotection under the hydrogenolytic debenzylation process because of the simultaneous reduction of azide to amine (Scheme 7.2.1.7). A selective debenzylation process under oxidative condition was preferably used in the presence of an azide.[42] Trisaccharide 8-25 was treated with $NaBrO_3$ and $Na_2S_2O_4$ in biphasic EtOAc/water solvent. Debenzylation was accomplished in 93% yield and the azide on the linker remained unharmed. Finally, the trisaccharide 8-26 was subjected to 4 N NaOH in aqueous methanolic solution and after biogel P-2 purification to obtain B4GAT1 trisaccharide motif 8-27 in 71% yield (Scheme 3.2.3.5).

Scheme 3.2.3.5 Final game for B4GAT1 trisaccharide motif 8-27

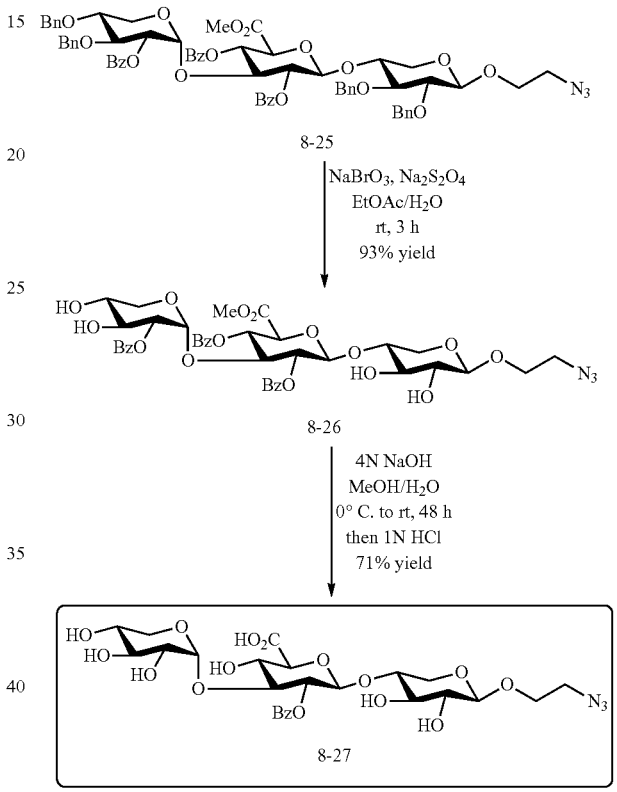

The synthesis of Xyl-α-(1→3)-GlcA-β-(1→4)-Xyl trisaccharide 8-27 was accomplished under the present disclosure including the characteristic B4GAT1glycan connection i.e GlcA-β-(1→4)-Xyl. The attached linker contained a functional azide group which can be used as a handle for conjugation to study the biological aspects of this glycan. Thus, under the present disclosure, the newly developed one-pot IAD was successfully applied to achieve Xyl-α-(1→3)-GlcA connectivity in the synthesis of trisaccharide 8-27 via preglycosylation-oxidation strategy. The failed glycosylation attempt showed the importance of acceptor reactivity in glycosylation which is often ignored by the carbohydrate community. The overall yield for trisaccharide was satisfactory and the final product was obtained in 15 mg scale. During the completion of the total synthesis of trisaccharide 8-27, phospho-ribitol, under the present disclosure, the actual linker between Xyl and Core M3 Man was discovered by collaborative work of Wells and Campbell.[41] From a synthetic perspective, it may be preferable to incorporate ribitol linker at the reducing end of Xyl in trisaccharide 8-27. The present disclosure preferably may be used in the study of the binding behavior, size dependency, and other biological aspects of synthetic α-DG associated glycans. The development will potentially lead to the understanding of the basis of various dystroglycanopathies and therefore will help to develop novel therapeutics for congenital muscular dystrophies (CMDs).

EXPERIMENTAL SECTION AND
SUPPLEMENTARY INFORMATION

General Information. All chemicals used were regent grade and used as supplied except where noted. All reactions were performed in oven-dried glassware under an inert atmosphere (nitrogen) unless noted otherwise. Reagent grade dichloromethane ($CH_2Cl_2$), diethyl ether ($Et_2O$), dimethylformamide (DMF) and toluene (PhMe) were passed through activated neutral alumina column prior to use. Pyridine, triethylamine and acetonitrile were distilled over $CaH_2$ prior to use. Analytical thin layer chromatography (TLC) was performed on Merck silica gel 60 $F_{254}$ plates (0.25 mm). Compounds were visualized by UV irradiation or dipping the plate in a cerium sulfate-ammonium molybdate solution. Flash column chromatography (FC) was carried out using Biotage Isolera One Flash Purification System over Silicycle P60 (230-400 mesh) silica gel. $^1H$ and $^{13}C$ NMR spectra were recorded on a Bruker DRX400 (400 MHz), Bruker DRX500 (500 MHz), or a Bruker AV600 (600 MHz) spectrometer in $CDCl_3$ with chemical shifts referenced to $CDCl_3$ (7.26 ppm for $^1H$ NMR and 77.02 ppm for $^{13}C$ NMR). Splitting patterns are indicated as s, singlet; d, doublet; t, triplet; q, quartet; bs, broad singlet for $^1H$ NMR data. High-resolution mass spectral (FIRMS) analyses were performed by the MS-service at the Department of Chemistry at University of Pittsburgh. HRMS-ESI were run on a Water® Q-TOF instrument. Optical rotations were measured using a Perkin-Elmer 241 polarimeter.

Example 1: Synthesis of α-Dystroglycan Associated Oligosaccharides

General Procedure E-a:

Single step β-mannosylation and β-rhamnosylation enabled by a sequential redox process: To a solution of 2-O-naphthylmethyl thioglycoside (0.12 mmol), a glycosyl acceptor (0.1 mmol) and 4 Å molecular sieves (200 mg) in anhydrous $CH_3CN$ (2 mL) was added DDQ (0.12 mmol) at room temperature. The mixture was stirred for 4-5 h for the complete formation of mixed acetal before adding anhydrous $K_2CO_3$ (0.4 mmol) and tris(4-bromophenyl)ammoniumyl hexachloroantimonate (($BrC_6H_4)_3NSbCl_6$) (0.35 mmol) in a sequential order. The reaction's color upon the addition of ($BrC_6H_4)_3NSbCl_6$ rapidly changed from deep blue to dark gray within 20-30 min, indicating the completion of the reaction. The mixture was filtered through a pad of Celite and the solvent was gently evaporated using a rotary evaporator (water bath temperature <30° C.). The residue was further taken up by $CH_2Cl_2$ and washed successively with sodium ascorbate solution (pH=7), saturated aqueous $NaHCO_3$ solution, water and brine, before dried with $Na_2SO_4$. Evaporation of the solvent in vacuo gave the crude residue which was further purified by a flash column chromatography to afford the target compound.

Example 2

(4,6-O-Cyclohexanylidene-3-O-triisopropylsilyl-β-D-mannopyranosyl)-(1→6)-1,2,3,4-di-O-isoprpopylidene-α-D-galactopyranoside (6-38)

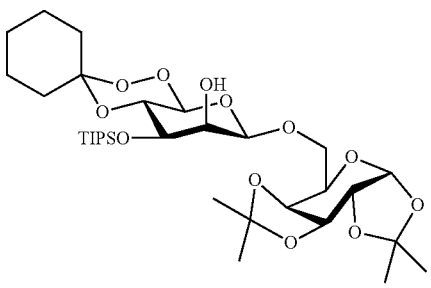

(4,6-O-Cyclohexanylidene-3-O-triisopropylsilyl-β-D-mannopyranosyl)-(1→6)-1,2,3,4-di-O-isoprpopylidene-α-D-galactopyranoside (6-38): General procedure E-a using ethylthio 4,6-O-cyclohexanylidene-2-O-napthylmethyl-3-O-triisopropylsilyl-α-D-mannopyranoside (77 mg, 0.128 mmol), 1,2,3,4-di-O-isoprpopylidene-α-D-galactopyranoside (28 mg, 0.107 mmol), 4 Å MS (200 mg), DDQ (29 mg, 0,128 mmol), $K_2CO_3$ (60 mg, 0.428 mmol) and ($BrC_6H_4)_3NSbCl_6$ (305 mg, 0.374 mmol) to give the target compound 6-38 (52 mg, 74% yield) as a syrup, $[α]_D^{21}$=−60 (c=0.3, $CHCl_3$), $^1H$ NMR (600 MHz, $CDCl_3$) δ 5.55 (d, 1H, J=4.8 Hz), 4.66 (s, 1H), 4.60 (dd, 1H, J=7.8 Hz, 2.4 Hz), 4.31 (dd, 1H, J=4.8 Hz, 1.8 Hz), 4.24 (dd, 1H, J=7.8 Hz, 1.2 Hz), 4.10 (dd, 1H, J=11.4 Hz, 3.0 Hz), 4.07-4.05 (m, 2H), 3.98 (dd, 1H, J=9.0 Hz, 9.0 Hz), 3.90 (dd, 1H, J=10.8 Hz, 6 Hz), 3.86 (d, 1H, 10.2 Hz), 3.83 (dd, 1H, J=8.4 Hz, 3.0 Hz), 3.77 (dd, 1H, J=11.4 Hz, 7.2 Hz), 3.17 (ddd, 1H, J=9.6 Hz, 9.6 Hz, 5.4 Hz), 1.63-1.36 (m, 10H), 1.51 (s, 3H), 1.46 (s, 3H), 1.33 (s, 6H), 1.17-1.01 (m, 21H). $^{13}C$ NMR (150 MHz, $CDCl_3$): δ 109.3, 108.6, 100.8, 99.8, 96.2, 72.7, 71.9, 71.4, 70.7, 70.3, 70.1, 69.3, 68.1, 68.0, 61.3, 38.0, 27.7, 26.0, 25.9, 25.6, 24.9, 24.3, 22.5, 22.3, 18.0, 18.0, 12.3. HRMS-ESI: m/z $C_{33}H_{58}O_{11}Si$ $[M+Na]^+$ calcd 681.3646, found 681.3640.

Example 3

(3,4,6-Tri-O-benzyl-β-D-mannopyranosyl)-(1→6)-1,2,3,4-di-O-isoprpopylidene-α-D-galactopyranoside (6-34)

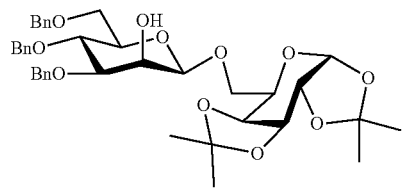

(3,4,6-Tri-O-benzyl-β-D-mannopyranosyl)-(1→6)-1,2,3,4-di-O-isoprpopylidene-α-D-galactopyranoside (6-34): General procedure E-a using ethylthio 3,4,6-tri-O-benzyl-2-O-napthylmethyl-α-D-mannopyranoside (81 mg, 0.128 mmol), 1,2,3,4-di-O-isoprpopylidene-α-D-galactopyranoside (28 mg, 0.107 mmol), 4 Å MS (200 mg), DDQ (29 mg, 0.128 mmol), K$_2$CO$_3$ (60 mg, 0.428 mmol) and (BrC$_6$H$_4$)$_3$NSbCl$_6$ (305 mg, 0.374 mmol) to give the target compound 6-34 (41 mg, 55% yield) as a syrup. [α]$_D^{21}$=−38.0 (c=1.2, CHCl$_3$). $^1$H NMR (500 MHz, CDCl$_3$) δ 7.40-7.20 (m, 15H), 5.57 (d, 1H, J=5 Hz), 4.92 (d, 1H, J=11 Hz), 4.79 (d, 1H, J=12 Hz), 4.67 (d, 1H, J=9.5 Hz), 4.65 (d, 1H, J=10 Hz), 4.61 (dd, 1H, J=8 Hz, 2.5 Hz), 4.56 (d, 1H, J=12.5 Hz), 4.53 (d, 1H, J=11.0 Hz), 4.53 (d, 1H, J=0.5 Hz), 4.33 (dd, 1H, 5 Hz, 2.5 Hz), 4.24-4.22 (m, 2H), 4.15 (dd, 1H, J=11 Hz, 2.5 Hz), 4.05 (ddd, 1H, J=7 Hz, 2 Hz, 2 Hz), 3.93 (dd, 1H, J=8.5 Hz, 8.5 Hz), 3.79-3.72 (m, 3H), 3.57 (dd, 1H, J=9.5 Hz, 3.5 Hz), 3.43 (ddd, 1H, J=8.5 Hz, 4.5 Hz, 2.5 Hz), 1.55 (s, 3H), 1.45 (s, 3H), 1.35 (s, 6H), 1.33 (s, 3H). $^{13}$C NMR (125 MHz, CDCl$_3$): δ 138.3, 138.2, 137.8, 128.4, 128.3, 128.0, 127.9, 127.8, 127.7, 127.5, 109.4, 108.7, 100.2, 96.3, 81.2, 75.2, 75.1, 74.1, 73.5, 71.4, 71.1, 70.7, 70.3, 69.1, 69.0, 68.0, 67.8, 26.1, 25.9, 24.9, 24.3. HRMS-ESI: m/z C$_{39}$H$_{48}$O$_{11}$ [M+Na]+ calcd 715.3094, found 715.3076.

Example 4

2-Azidoethyl 4,6-O-cyclohexanylidene-3-O-triisopropylsilyl-β-D-mannopyranoside (6-27)

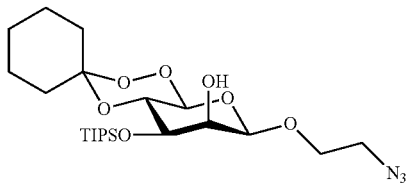

2-Azidoethyl 4,6-O-cyclohexanylidene-3-O-triisopropylsilyl-β-D-mannopyranoside (6-27): General procedure E-a using ethylthio 4,6-O-cyclohexanylidene-2-0-napthylmethyl-α-D-mannopyranoside (206 mg, 0.344 mmol), 2-azidoethanol (25 mg, 0.287 mmol), 4 Å MS (200 mg), DDQ (78 mg, 0.344 mmol), K$_2$CO$_3$ (190 mg, 1,148 mmol) and (BrC$_6$H$_4$)$_3$NSbCl$_6$ (820 mg, 1.004 mmol) to give the target compound 6-27 (115 mg, 68% yield) as a syrup. [α]$_D^{21}$=−30.3 (c=1.8, CHCl$_3$). $^1$H NMR (400 MHz, CDCl$_3$) δ 4.60 (s, 1H), 4.11 (ddd, 1H, J=10 Hz, 4.8 Hz, 4.8 Hz), 4.06 (d, 1H, J=3.2 Hz), 3.97 (dd, 1H, J=9.6 Hz, 9.6 Hz), 3.89 (dd, 1H, J=8 Hz, 4.8 Hz), 3.87-3.84 (m, 2H), 3.75 (ddd, 1H, J=10.8 Hz, 8.0 Hz, 4 Hz), 3.59 (ddd, 1H, J=13.2 Hz, 8 Hz, 4 Hz), 3.42 (ddd, 1H, J=13.2 Hz, 4.4 Hz, 4.4 Hz), 3.19 (ddd, 1H, J=10 Hz, 9.6 Hz, 6 Hz), 2.70 (s, 1H), 1.65-1.33 (m, 10H), 1.18-1.00 (m, 21H). $^{13}$C NMR (100 MHz, CDCl$_3$): δ 100.8, 100.0, 72.6, 71.8, 70.0, 68.5, 68.1, 61.2, 50.6, 37.9, 27.7, 25.6, 22.5, 22.3, 18.0, 17.9, 12.3. HRMS-ESI: m/z C$_{23}$H$_{43}$N$_3$O$_6$Si [M+Na]$^+$ calcd 508.2819, found 508.2830.

Example 5

2-Azidoethyl 3,4,6-tri-O-benzyl-β-D-mannopyranoside (6-28)

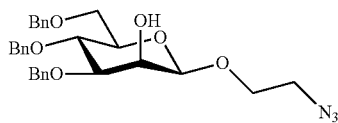

2-Azidoethyl 3,4,6-tri-O-benzyl-β-D-mannopyranoside (6-28): General procedure E-a using ethylthio 3,4,6-tri-O-benzyl-2-O-napthylmethyl-α-D-mannopyranoside (109 mg, 0.172 mmol), 2-azidoethanol (13 mg, 0.143 mmol), 4 Å MS (150 mg), DDQ (39 mg, 0.172 mmol), K$_2$CO$_3$ (79 mg, 0.572 mmol) and (BrC$_6$H$_4$)$_3$NSbCl$_6$ (408 mg, 0.5 mmol) to give the target compound 6-28 (45 mg, 63% yield) as a syrup. [α]$_D^{21}$=−15.4 (c=2.2, CHCl$_3$). $^1$H NMR (500 MHz, CDCl$_3$) δ 7.41-7.21 (m, 15H), 4.91 (d, 1H, J=10.5), 4.80 (d, 1H, J=12 Hz), 4.69 (d, 1H, J=10.5 Hz), 4.64 (d, 1H, J=12 Hz), 4.57 (d, 1H, J=10 Hz), 4.55 (d, 1-1, J=9.5 Hz), 4.51 (d, 1H, J=1.0 Hz), 4.18 (bs, 1H), 4.13 (ddd, 1H, J=11 Hz, 4.5 Hz, 3.5 Hz), 3.89 (dd, 1H, J=9.5 Hz, 9.5 Hz), 3.77 (dd, 1H, J=10.5 Hz, 10.5 Hz, 2 Hz), 3.76-3.71 (m, 2H), 3.60 (dd, 1H, J=9.0 Hz, 3.5 Hz), 3.56 (ddd, 1H, J=8.5 Hz, 8.5 Hz, 5 Hz), 3.47 (ddd, 1H, J=4 Hz, 4 Hz, 2 Hz), 3.40 (ddd, 1H, J=10.5 Hz, 5 Hz, 5 Hz), 2.43 (d, 1H, J=2 Hz). $^{13}$C NMR (125 MHz, CDCl$_3$): δ 138.1, 138.1, 137.7, 128.5, 128.4, 128.3, 128.1, 127.9, 127.8, 127.8, 127.6, 99.9, 81.3, 75.3, 75.2, 74.1, 73.5, 71.4, 69.1, 68.3, 68.0, 50.6. HRMS-ESI: m/z C$_{29}$H$_{33}$N$_3$O$_6$ [M+Na]$^+$ calcd 542.2267, found 542.2268.

Example 6

(3-O-Benzyl-4,6-di-O-benzoyl-β-D-mannopyranosyl)-(1→6)-1,2,3,4-di-O-isoprpopylidene-α-0-galactopyranoside (6-33)

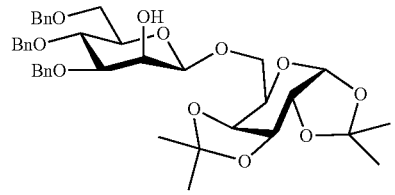

(3-O-Benzyl-4,6-di-O-benzoyl-β-D-mannopyranosyl)-(1→6)-1,2,3,4-di-O-isoprpopylidene-α-D-galactopyranoside (6-33): General procedure E-a using ethylthio 3-O-benzyl-4,6-di-O-benzoyl-2-O-napthylmethyl-α-D-mannopyranoside (84 mg, 0.128 mmol), 1,2,3,4-di-O-isoprpopylidene-α-D-galactopyranoside (28 mg, 0.107 mmol), 4 Å MS (100 mg), DDQ (29 mg, 0.128 mmol), K$_2$CO$_3$ (60 mg, 0,428 mmol) and (BrC$_6$H$_4$)$_3$NSbCl$_6$ (305 mg, 0.374 mmol) to give the target compound 6-33 (50 mg, 65% yield) as a syrup. [α]$_D^{21}$=−41.0 (c=1.7, CHCl$_3$). $^1$H NMR (600 MHz, CDCl$_3$) δ 8.01-7.98 (m, 4H), 7.60-7.57 (m, 1H), 7.53-7.50 (m, 1H), 7.45-7.42 (m, 2H), 7.37-7.34 (m, 2H), 7.24-7.18 (m, 5H), 5.72 (dd, 1H, J=8.4 Hz, 8.4 Hz), 5.56 (d, 1-1, J=4.8 Hz), 4.73 (d, 1H, J=12 Hz), 4.72 (d, 1H, J=1.2 Hz), 4.60 (dd, 1H, J=12 Hz, 3.6 Hz), 4.59 (d, 1H, J=10.2 Hz), 4.58 (d, 1H, J=10.2 Hz), 4.46 (dd, 1H, J=12 Hz, 5.4 Hz), 4.33 (dd, 1H, J=4.8 Hz, 2.4 Hz), 4.32 (dd, 1H, J=3.6 Hz, 1.2 Hz), 4.18 (dd, 1H, J=7.8 Hz, 1.8 Hz), 4.12 (dd, 1H, J=11.4 Hz, 3 Hz), 4.06 (ddd, 1H, J=7.8 Hz, 2.4 Hz, 2.4 Hz), 3.87 (ddd, 1H, J=9 Hz, 6 Hz, 3.6 Hz), 3.79 (dd, 1H, J=11.4 Hz, 7.8 Hz), 3.71 (dd, 1H, J=9.0 Hz, 3.6 Hz), 1.55 (s, 3H), 1.42 (s, 3H), 1.35 (s, 3H), 1.31 (s, 3 11). $^{13}$C NMR (150 MHz, CDCl$_3$): δ 166.2, 165.3, 137.2, 133.2, 132.9, 129.8, 129.8, 129.7, 129.6, 128.4, 128.3, 128.2, 127.9, 127.8, 109.4, 108.7, 100.4, 96.2, 77.5, 72.1, 71.3, 71.0, 70.6, 70.3, 69.4, 68.6, 68.1, 67.5, 63.8, 26.1, 25.9, 24.9, 24.3. HRMS-ESI: m/z C$_{39}$H$_{44}$O$_{13}$ [M+Na]$^+$ calcd 743.2680, found 743.2709.

Example 7

(3,4-Di-O-benzyl-β-L-rhamnopyranosyl)-(1→6)-1,2,3,4-di-O-isoprpopylidene-α-D-galactopyranoside (6-31)

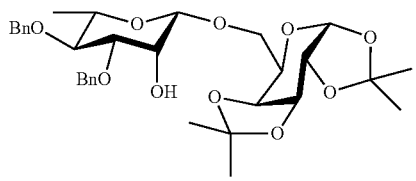

(3,4-Di-O-benzyl-β-L-rhamnopyranosyl)-(1→6)-1,2,3,4-di-O-isoprpopylidene-α-D-galactopyranoside (6-31): General procedure E-a using ethylthio 3,4-di-O-benzyl-2-O-napthylmethyl-α-L-rhamnopyranoside (68 mg, 0.128 mmol), 1,2,3,4-di-O-isoprpopylidene-α-D-galactopyranoside (28 mg, 0.107 mmol), 4 Å MS (75 mg), DDQ (29 mg, 0.128 mmol), $K_2CO_3$ (30 mg, 0.214 mmol) and $(BrC_6H_4)_3NSbCl_6$ (305 mg, 0.374 mmol) to give the target compound 6-31 (42 mg, 67% yield) as a syrup. $[\alpha]_D^{21}=-19.8$ (c=2.6, $CHCl_3$). $^1H$ NMR (500 MHz, $CDCl_3$) δ 7.41-7.28 (m, 10H), 5.52 (d, 1H, J=5 Hz), 4.96 (d, 1H, J=11 Hz), 4.79 (d, 1H, J=12 Hz), 4.70 (d, 1H, J=11.5 Hz), 4.66 (d, 1H, J=11 Hz), 4.63 (dd, 1H, J=8 Hz, 2.5 Hz), 4.46 (s, 1H), 4.36 (dd, 1H, J=8 Hz, 2 Hz), 4.33 (dd, 1H, J=5 Hz, 2 Hz), 4.17 (d, 1H, J=2 Hz), 4.08 (ddd, 1H, J=7 Hz, 7 Hz, 2 Hz), 3.93 (dd, 1H, J=10 Hz, 7.2 Hz), 3.79 (dd, 1H, J=9 Hz, 9 Hz), 3.58-3.49 (m, 1H), 3.37-3.32 (m, 1H), 1.53 (s, 3H), 1.47 (s, 3H), 1.37 (s, 3H), 1.35 (d, 3H, J=6 Hz) 1.34 (s, 3H). $^{13}C$ NMR (125 MHz, $CDCl_3$): δ 138.3, 137.9, 128.4, 128.4, 128.1, 127.9, 127.8, 127.7, 109.2, 108.6, 100.0, 96.2, 81.2, 79.5, 75.5, 71.6, 71.4, 70.6, 70.6, 70.5, 68.0, 67.2, 65.5, 26.1, 25.9, 24.9, 24.5, 17.8. HRMS-ESI: m/z $C_{32}H_{42}O_{10}$ [M+K]$^+$ calcd 625.2415, found 625.2413.

Example 8

2-Azidoethyl 3,4-di-O-benzyl-β-L-rhamnopyranoside (6-29)

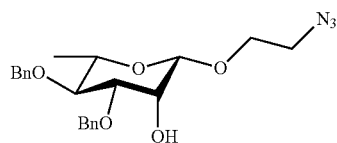

2-Azidoethyl 3,4-di-O-benzyl-β-L-rhamnopyranoside (6-29): General procedure E-a using ethylthio 3,4-di-O-benzyl-2-O-napthylmethyl-α-L-rhamnopyranoside (91 mg, 0.172 mmol), 2-azidoethanol (13 mg, 0.143 mmol), 4 Å MS (75 mg), DDQ (40 mg, 0.172 mmol), $K_2CO_3$ (40 mg, 0.287 mmol) and $(BrC_6H_4)_3NSbCl_6$ (410 mg, 0.502 mmol) to give the target compound 6-29 (41 mg, 69% yield) as a syrup. $[\alpha]_D^{21}=+37.1$ (c=1.6, $CHCl_3$). $^1H$ NMR (600 MHz, $CDCl_3$) δ 7.41-7.28 (m, 10H), 4.96 (d, 1H, J=10.8 Hz), 4.79 (d, 1H, J=11.4 Hz), 4.70 (d, 1H, J=12 Hz), 4.67 (d, 1H, J=10.8 Hz), 4.47 (s, 1H), 4.17 (bs, 1H), 4.10 (ddd, 1H, J=9 Hz, 4.8 Hz, 4.8 Hz), 3.72 (ddd, 1H, J=9.6 Hz, 9.6 Hz, 3.6 Hz), 3.62-3.54 (m, 3H), 3.41-3.35 (m, 2H), 2.40 (s, 1H), 1.37 (d, 3H, J=6 Hz). $^{13}C$ NMR (150 MHz, $CDCl_3$): δ 138.1, 137.7, 128.5, 128.4, 128.4, 128.3, 128.3, 128.3, 128.1, 128.0, 128.0, 127.9, 127.9, 127.8, 127.7, 127.5, 99.7, 81.2, 79.7, 79.4, 75.5, 72.2, 71.9, 71.6, 71.4, 68.2, 68.2, 50.6, 17.8. HRMS-ESI: m/z $C_{22}H_{27}N_3O_5$ [M+Na]$^+$ calcd 436.1848, found 436.1829.

Example 9

Butyl-(4,6-O-cyclohexanylidene-3-O-triisopropylsilyl-β-D-mannopyranosyl)-(1→4)-3,6-di-O-benzyl-2-deoxy-2-N-phthalimido-β-D-glucopyranoside (6-36)

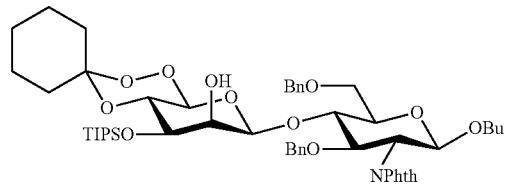

Butyl-(4,6-O-cyclohexanylidene-3-O-triisopropylsilyl-β-D-mannopyranosyl)-(1→4)-3,6-di-O-benzyl-2-deoxy-2-N-phthalimido-β-D-glucopyranoside (6-36): General procedure E-a using ethylthio 4,6-O-cyclohexanylidene-2-napthylmethyl-3-O-triisopropylsilyl-α-D-mannopyranoside (61 mg, 0.1 mmol), butyl 3,6-di-O-benzyl-2-deoxy-2-N-phthalimido-β-D-glucopyranoside (50 mg, 0.091 mmol), 4 Å MS (75 mg), DDQ (25 mg, 0.1 mmol), $K_2CO_3$ (50 mg, 0.364 mmol) and $(BrC_6H_4)_3NSbCl_6$ (260 mg, 0.318 mmol) to give the target compound 6-36 (41 mg, 63% yield) as a syrup. $[\alpha]_D$+23.5 (c=3.2, $CHCl_3$), $^1H$ NMR (600 MHz, $CDCl_3$) δ 7.75-7.67 (m, 4H), 7.38-7.31 (m, 5H), 7.04 (d, 2H, J=7.2 Hz), 6.90-6.85 (m, 3H), 5.11 (d, 1H, J=9.0 Hz), 4.87 (d, 1H, J=12 Hz), 4.76 (d, 1H, J=12 Hz), 4.69 (s, 1H), 4.55 (d, 1H, J=12 Hz), 4.51 (d, 1H, J=12 Hz), 4.39 (dd, 1H, J=10.8 Hz, 9 Hz), 4.17 (dd, 1H, J=10.8 Hz, 8.4 Hz), 4.12 (dd, 1H, J=9 Hz, 9 Hz), 3.94 (app d, 1H, J=3 Hz), 3.85-3.76 (m, 5H), 3.70 (dd, 1H, J=9 Hz, 3.6 Hz), 3.68-3.66 (m, 1H), 3.54 (dd, 1H, J=10.8 Hz, 10.8 Hz), 3.39 (ddd, 1H, J=10.2 Hz, 6.6 Hz, 6.6 Hz), 2.98 (ddd, 1H, J=9.6 Hz, 9.6 Hz, 4.8 Hz), 2.85 (bs, 1H), 2.00-1.48 (m, 10H), 1.41-1.33 (m, 6H), 1.13-1.05 (m, 21H), 0.65 (t, 3H, J=7.2 Hz). $^{13}C$ NMR (150 MHz, $CDCl_3$): δ 168.1, 167.6, 138.7, 138.0, 133.6, 128.4, 127.8, 127.7, 127.6, 127.6, 126.9, 123.0, 100.7, 99.7, 98.4, 79.0, 76.8, 74.6, 74.5, 73.5, 72.7, 72.0, 70.1, 69.2, 68.5, 67.7, 61.2, 55.8, 37.9, 36.6, 31.2, 27.7, 25.6, 24.6, 22.5, 22.2, 18.8, 18.0, 17.9, 13.4, 12.3. HRMS-BSI: m/z $C_{53}H_{73}NO_{12}Si$ [M+Na]$^+$ calcd 966.4800, found 966.4780.

Example 10

Butyl-(3,4,6-tri-O-benzyl-β-D-mannopyranosyl)-(1→4)-3,6-di-O-benzyl-2-deoxy-2-N-phthalimido-β-D-glucopyranoside (6-35)

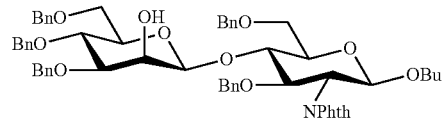

Butyl-(3,4,6-tri-O-benzyl-β-D-mannopyranosyl)-(1→4)-3,6-di-O-benzyl-2-deoxy-2-N-phthalimido-β-D-glucopyranoside (6-35): General procedure E-a using ethylthio 3,4,6-tri-O-benzyl-2-napthylmethyl-α-D-mannopyranoside (50 mg, 0.078 mmol), butyl 3,6-di-O-benzyl-2-deoxy-2-N-phthalimido-β-D-glucopyranoside (36 mg, 0.065 mmol), 4 Å MS (50 mg), DDQ (18 mg, 0.078 mmol), K$_2$CO$_3$ (36 mg, 0.26 mmol) and (BrC$_6$H$_4$)$_3$NSbCl$_6$ (185 mg, 0.23 mmol) to give the target compound 6-35 (33 mg, 67% yield) as a syrup. $[\alpha]_D^{21}$=+36.6 (c=1.7, CHCl$_3$). $^1$H NMR (600 MHz, CDCl$_3$) δ 7.75-7.67 (m, 4H), 7.35-7.21 (m, 20H), 7.01 (d, 2H, J=7.2 Hz), 6.83-6.80 (m, 3H), 5.12 (d, 1H, J=8.4 Hz), 4.91 (d, 1H, J=12.6 Hz), 4.86 (d, 1H, J=10.8 Hz), 4.77 (d, 1H, J=12 Hz), 4.74 (s, 1H), 4.69 (d, 1H, J=9.6 Hz), 4.55-4.53 (m, 2H), 4.53 (dd, 1H, J=6.6 Hz, 6.6 Hz), 4.48 (d, 1H, J=12 Hz), 4.46 (d, 1H, J=12.6 Hz), 4.40 (dd, 1H, J=10.8 Hz, 9 Hz), 4.19 (dd, 1H, J=10.8 Hz, 9 Hz), 4.09 (dd, 1H, J=9 Hz, 9 Hz), 4.04 (bs, 1H), 3.87 (dd, 1H, J=9.6 Hz, 9.6 Hz), 3.85 (dd, 1H, J=12 Hz, 3.6 Hz), 3.80-3.77 (m, 2H), 3.71 (app d, 1H, J=9.6 Hz), 3.66 (ddd, 1H, J=9.6 Hz, 2.4 Hz, 2.4 Hz), 3.63 (dd, 1H, J=10.8 Hz, 4.2 Hz), 3.41 (dd, 1H, J=9 Hz, 3 Hz), 3.39 (ddd, 1H, J=9.6 Hz, 6.6 Hz, 6.6 Hz), 2.51 (bs, 1H), 1.44-1.05 (m, 6H), 0.66 (t, 3H, J=7.2 Hz). $^{13}$C NMR (150 MHz, CDCl$_3$): δ 168.2, 167.6, 138.5, 138.3, 138.2, 137.9, 137.9, 128.4, 128.3, 128.2, 128.0, 127.9, 127.8, 127.8, 127.7, 127.6, 127.4, 126.9, 100.4, 98.4, 81.6, 78.4, 78.1, 75.4, 75.1, 74.7, 74.5, 73.9, 73.5, 73.3, 71.3, 69.2, 68.9, 68.7, 68.68.0, 55.8, 31.2, 18.8, 13.4. HRMS-ESI: m/z C$_{59}$H$_{63}$NO$_{12}$ [M+Na]$^+$ calcd 1000.4248, found 1000.4244.

Example 11

Methyl-(3,4-di-O-benzyl-β-L-rhamnopyranosyl)-(1→4)-2,3-O-isoprpopylidene-α-L-rhamnopyranoside (6-32)

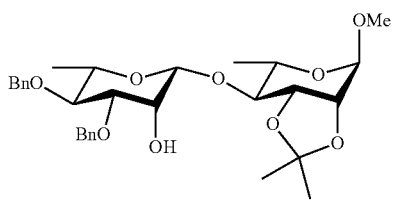

Methyl-(3,4-di-O-benzyl-β-L-rhamnopyranosyl)-(1→4)-2,3-O-isoprpopylidene-α-L-rhamnopyranoside (6-32): General procedure E-a using ethylthio 3,4-di-O-benzyl-2-napthylmethyl-α-L-$_{rhamnopyranoside}$ (67 mg, 0.128 mmol), methyl 2,3-O-isoprpopylidene-α-L-rhamnopyranoside (24 mg, 0.107 mmol), 4 Å MS (100 mg), DDQ (29 mg, 0.128 mmol), K$_2$CO$_3$ (30 mg, 0.217 mmol) and (BrC$_6$H$_4$)$_3$NSbCl$_6$ (305 mg, 0.38 mmol) to give the target compound 6-32 (41 mg, 68% yield) as a syrup. $[\alpha]_D^{21}$=−1.7 (c=2.2, CHCl$_3$). $^1$H NMR (700 MHz, CDCl$_3$) δ 7.42-7.28 (m, 10H), 4.97 (d, 1H, J=10.5 Hz), 4.86 (s, 1H), 4.81 (d, 1H, J=11.9 Hz), 4.71 (d, 1H, J=11.9 Hz), 4.68 (d, 1H, J=10.5 Hz), 4.60 (s, 1H), 4.36-4.28 (m, 1H), 4.18-4.12 (m, 1H), 4.15 (s, 1H), 3.73 (ddd, 11-1, J=9.1 Hz, 6.3 Hz, 6.3 Hz), 3.59-3.55 (m, 2H), 3.51 (dd, 1H, J=9.1 Hz), 3.38 (s, 3H), 1.54 (s, 3H), 1.37 (d, 3H, J=6.3 Hz), 1.36 (s, 3H), 1.31 (d, 3H, J=5.6 Hz). $^{13}$C NMR (175 MHz, CDCl$_3$): δ 138.4, 137.9, 128.4, 128.4, 128.1, 127.9, 127.8, 127.7, 109.0, 99.6, 98.2, 81.7, 81.3, 79.5, 76.6, 76.0, 75.4, 71.8, 71.4, 68.3, 64.4, 54.8, 28.0, 26.2, 17.8, 17.7. HRMS-ESI: m/z C$_{30}$H$_{40}$O$_9$ [M+Na]$^+$ calcd 567.2570, found 567.2565.

Example 12

Methyl-(4,6-O-cyclohexanylidene-3-triisopropyl-β-D-mannopyranosyl)-(1→4)-2,3-O-isoprpopylidene-α-L-rhamnopyranoside (6-37)

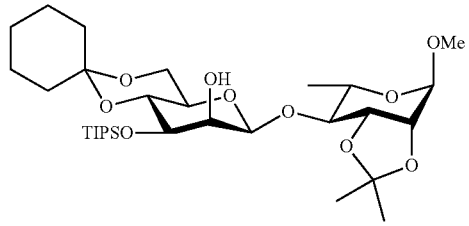

Methyl-(4,6-O-cyclohexanylidene-3-triisopropyl-β-D-mannopyranosyl)-(1→4)-2,3-O-isoprpopylidene-α-L-rhamnopyranoside (6-37): General procedure using ethylthio 4,6-O-cyclohexanylidene-2-napthylmethyl-3-O-triisopropylsilyl-α-D-mannopyranoside (77 mg, 0.128 mmol), methyl 2,3-O-isoprpopylidene-α-L-rhamnopyranoside (24 mg, 0.107 mmol), 4 Å MS (100 mg), DDQ (29 mg, 0.128 mmol), K$_2$CO$_3$ (30 mg, 0.217 mmol) and (BrC$_6$H$_4$)$_3$NSbCl$_6$ (305 mg, 0.38 mmol) to give the target compound 6-37 (40 mg, 66% yield) as a syrup. $[\alpha]_D^{21}$=−37.1 (c=2.8, CHCl$_3$). $^1$H NMR (600 MHz, CDCl$_3$) δ 5.04 (d, 1H, J=0.6 Hz), 4.88 (s, 1H), 4.24 (dd, 1H, J=7.2 Hz, 1.2 Hz), 4.11 (d, 1H, J=9 Hz), 4.01 (dd, 1H, J=3.6 Hz, 0.6 Hz), 3.95 (dd, 1H, J=9 Hz, 9 Hz), 3.90-3.85 (m, 3H), 3.74-3.69 (m, 2H), 3.37 (m, 1H), 3.37 (s, 3H), 3.15 (ddd, 1H, J=12 Hz, 7.8 Hz, 7.2 Hz), 2.70 (bs, 1H), 1.63-1.37 (m, 10H), 1.53 (s, 3H), 1.37 (s, 3H), 1.31 (d, 3H, J=6 Hz), 1.18-1.09 (m, 21H). $^{13}$C NMR (150 MHz, CDCl$_3$): δ 109.3, 100.0, 98.6, 97.7, 78.3, 77.6, 76.1, 72.7, 72.0, 70.6, 68.0, 64.0, 61.3, 54.7, 38.0, 27.8, 26.4, 25.6, 22.5, 22.2, 18.0, 17.9, 17.5, 12.3. HRMS-ESI: m/z C$_{31}$H$_{56}$O$_{10}$Si [M+Na]$^+$ calcd 639.3540, found 639.3561.

Example 13

6-N-Phthalimidohexanyl 3,4,6-tri-O-benzyl-β-D-mannopyranoside (6-30)

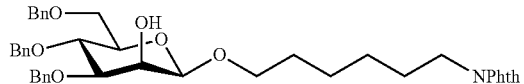

6-N-Phthalimidohexanyl 3,4,6-tri-O-benzyl-β-D-mannopyranoside (6-30): General procedure E-a using ethylthio 3,4,6-tri-O-benzyl-2-O-napthylmethyl-α-D-mannopyranoside (50 mg, 0.078 mmol), 6-N-phthalimidohexanol (16 mg, 0.065 mmol), 4 Å MS (50 mg), DDQ (18 mg, 0.078 mmol), K$_2$CO$_3$ (43 mg, 0.312 mmol) and (BrC$_6$H$_4$)$_3$NSbCl$_6$ (222 mg, 0.273 mmol) to give the target compound 6-30 (31 mg, 72% yield) as a syrup. $[\alpha]_D^{21}$=+3.1 (c=1.2, CHCl$_3$). $^1$H NMR (600 MHz, CDCl$_3$) δ 7.85 (dd, 2H, J=5.4 Hz, 3 Hz), 7.71 (dd, 1H, J=5.4 Hz, 3 Hz), 4.91 (d, 11-1, J=11.4 Hz), 4.80 (d, 1H, J=12 Hz), 4.69 (d, 1H, J=12 Hz), 4.63 (d, 1H, J=12 Hz), 4.578 (d, 1H, J=12 Hz), 4.573 (d, 1H, J=10.8 Hz), 4.24 (s, 1H), 4.12 (dd, 1H, J=2.4 Hz, 2.4 Hz), 3.93 (ddd, 1H, J=9.6 Hz, 6 Hz, 6 Hz), 3.88 (dd, 1H, J=9 Hz, 9 Hz), 3.79 (dd, 1H, J=10.8 Hz, 1.8 Hz), 3.72 (dd, 1H, J=11.4 Hz, 6 Hz), 3.70 (d, 1H, J=7.2 Hz), 3.69 (d, 1H, J=7.2 Hz), 3.58 (dd, 1H, J=9.6 Hz, 3 Hz), 3.52 (ddd, 1H, J=9.6 Hz, 7.2 Hz, 7.2 Hz), 3.44 (ddd, 1H, J=9 Hz, 5.4 Hz, 2.4 Hz), 2.45 (d, 1H, J=1.8 Hz), 1.75-1.61 (m, 4H), 1.46-1.33 (m, 4H). $^{13}$C NMR (150 MHz, CDCl$_3$) δ 168.3, 138.4, 138.3, 137.9, 133.8, 132.2, 128.4, 128.3, 128.2, 128.2, 128.1, 128.0, 127.9, 127.8, 127.8, 127.7, 127.7, 127.6, 127.6, 127.4, 123.1, 123.1, 99.7, 81.7, 75.4, 75.1, 74.4, 73.5, 73.4, 71.3, 69.5, 69.4, 68.3, 62.7, 37.8, 29.3, 28.4, 26.5, 25.5. HRMS-ESI: m/z C$_{41}$H$_{45}$NO$_8$ [M+Na]$^+$ calcd 702.3043, found 702.3027.

Example 14

6-N-Phthalimidohexanyl-(3,4,6-tri-O-benzyl-β-D-mannopyranosyl)-(1→2)-3,4,6-tri-O-benzyl-β-D-mannopyranoside (6-39)

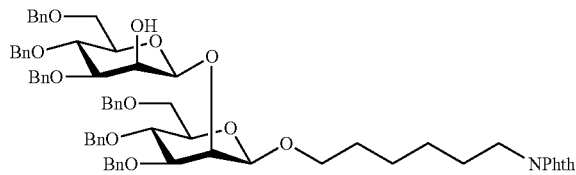

6-N-Phthalimidohexanyl-(3,4,6-tri-O-benzyl-β-D-mannopyranosyl)-(1→2)-3,4,6-tri-O-benzyl-β-D-mannopyranoside (6-39): General procedure E-a using ethylthio 3,4,6-tri-O-benzyl-2-O-napthylmethyl-α-D-mannopyranoside (88 mg, 0.139 mmol), 6-N-Phthalimidohexanyl 3,4,6-tri-O-benzyl-β-D-mannopyranoside 6-30 (79 mg, 0.116 mmol), 4 Å MS (170 mg), DDQ (32 mg, 0.139 mmol), K$_2$CO$_3$ (64 mg, 0.462 mmol) and (BrC$_6$H$_4$)$_3$NSbCl$_6$ (330 mg, 0.405 mmol) to give the target compound 6-39 (68 mg, 53% yield) as a syrup. $^1$H NMR (700 MHz, CDCl$_3$) δ 7.79 (dd, 2H, J=4.9 Hz, 2.8 Hz), 7.65 (dd, 2H, J=4.9 Hz, 2.8 Hz), 7.37-7.14 (m, 30H), 4.946 (s, 1H), 4.940 (d, 1H, J=11.2 Hz), 4.92 (d, 1H, J=11.2 Hz), 4.86 (d, 1H, J=10.5 Hz), 4.82 (d, 1H, J=11.9 Hz), 4.62 (d, 1H, J=11.9 Hz), 4.60 (d, 1H, J=11.9 Hz), 4.54 (d, 2H, J=11.9 Hz), 4.49 (d, 1H, J=2.8 Hz), 4.46 (d, 1H, J=11.9 Hz), 4.45 (d, 2H, J=11.2 Hz), 4.42 (d, 1H, J=11.9 Hz), 4.36 (s, 1H), 4.33 (d, 1H, J=2.8 Hz), 3.91 (dd, 1H, J=9.8 Hz, 9.8 Hz), 3.89 (m, 1H,), 3.77-3.74 (m, 3H), 3.69 (dd, 1H, J=11.2 Hz, 5.6 Hz), 3.67 (dd, 1H, J=11.2 Hz, 5.6 Hz), 3.64 (t, 3H), 3.58 (dd, 1H, J=9.1 Hz, 2.8 Hz), 3.56 (dd, 1H, J=10.8 Hz, 3.5 Hz), 3.51 (ddd, 1H, J=9.4 Hz, 7.0 Hz, 7.0 Hz), 3.42-3.37 (m, 2H), 1.71-1.53 (m, 4H), 1.38-1.30 (m, 4H), $^{13}$C NMR (175 MHz, CDCl$_3$) δ 168.4, 138.4, 138.3, 138.2, 138.1, 138.0, 133.8, 132.0, 128.3(2), 128.2, 128.2, 128.1(2), 127.9(2), 127.8, 127.7, 127.6, 127.5, 123.1, 101.0, 99.2, 81.3, 80.3, 75.4, 75.1, 75.0, 74.0, 73.4, 73.3, 70.6, 70.5, 69.9, 69.8, 69.4, 67.6, 37.7, 29.4, 28.4, 26.4, 25.4. HRMS-ESI: m/z C$_{41}$H$_{45}$NO$_8$ [M+H]$^+$ calcd 1112.51547, found 1112.51582.

Synthesis of a Series of Large Glycans

Example 15

Ethyl 2-O-acetyl-3,4-di-O-benzyl-β-D-thioxylopyranoside (7-18)

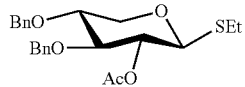

Ethyl 2-O-acetyl-3,4-di-O-benzyl-β-D-thioxylopyranoside (7-18): Compound 7-17 was synthesized from D-xylose following the literature προχεδυρε (J. Org. Chem., 2008, 73, 157-161) in 35 g scale (overall 41% yield). To a solution of 7-17 (16 g, 38.4 mmol) in dry DCM (120 mL) were added 4 Å molecular sieves (7 g) and mercaptoethanol (1.2 g, 19.2 mmol). The mixture was stirred for 1 h at room temperature before cooling down at 0° C. in an ice-bath. TMSOTf (0.7 mL, 3.84 mmol) was added dropwise and then the mixture was slowly warmed at room temperature and further stirred for 10 h. The reaction mixture was then cooled in ice-bath and quenched with slow addition of triethylamine. After filtering through Celite®, the solvent was evaporated under reduced pressure and the crude was purified by flash chromatography to afford 7-18 (10.1 g, 24.1 mmol) in 63% yield. $^1$H NMR (400 MHz, CDCl$_3$): δ 7.34-7.24 (m, 10H), 4.95 (dd, 1H, J=8.8 Hz, 8.8 Hz), 4.83 (d, 1H, 0.1=11.6 Hz), 4.69 (d, 1H, J=11.6 Hz), 4.68 (d, 1H, J=11.6 Hz), 4.60 (d, 1H, J=11.6 Hz), 4.38 (d, 1H, J=9.2 Hz), 4.07 (dd, 1H, J=12.0 Hz, 5.2 Hz), 3.67-3.64 (m, 1H), 3.61 (dd, 1H, J=8.4 Hz, 8.4 Hz), 3.27 (dd, 1H, J=11.6 Hz, 9.6 Hz), 2.70-2.60 (m, 2H), 1.98 (s, 3H), 1.23 (t, 3H, J=7.6 Hz).

Example 16

Ethyl 2-O-napthylmethyl-3,4-di-O-benzyl-β-D-thioxylopyranoside (7-10)

Ethyl 2-O-napthylmethyl-3,4-di-O-benzyl-β-D-thioxylopyranoside (7-10)

Under N$_2$ atmosphere, to a solution of 7-18 (10 g, 24 mmol) in MeOH (80 mL) was added sodium methoxide (0.26 g, 4.8 mmol) portionwise at ambient temperature. The mixture was stirred at 40° C. for 4 hours, Upon completion, the reaction mixture was concentrated and crude residue was purified by flash chromatography to obtain 7-19 as a syrup. The compound without further purification was dissolved in dry DMF (60 mL) and cooled in an ice-bath. Then 60 wt % sodium hydride (1.92 g, 48 mmol) was added portion-wise followed by the stirring of the mixture at 0° C. for 30 min. NAPBr (8 g, 36 mmol) was added and the mixture was slowly warmed up at room temperature and the stirring was continued for 12 h. The reaction mixture was then quenched with crushed ice and diluted with water. Aqueous layer was extracted with ether (3×70 mL) and combined organic layer was washed with water, brine, and then dried over anhydrous $Na_2SO_4$. After filtration, the solvent was evaporated and residue was purified by flash chromatography to obtain 7-10 in 75% yield. $^1$H NMR (400 MHz, $CDCl_3$): δ 7.81-7.76 (m, 4H), 7.52-7.43 (m, 3H), 7.31-7.21 (m, 10H) 5.03 (d, 1H, J=11.2 Hz), 4.92 (d, 1H, J=12 Hz), 4.91 (d, 1H, J=12 Hz), 4.86 (d, 1H, J=11.6 Hz), 4.71 (d, 1H, J=11.6 Hz), 4.62 (d, 1H, J=11.6 Hz), 4.46 (d, 1H, J=9.2 Hz), 4.02 (dd, 1H, J=11.2 Hz, 4 Hz), 3.64-3.63 (m, 2H), 3.43-3.39 (m, 1H), 3.23-3.20 (m, 1H), 2.76-2.70 (m, 2H), 1.29 (t, 3H, J=7.6 Hz).

Example 17

1,2,4,6-tetra-O-benzoyl-3-O-benzyl-β-D-glucopyranoside (7-23)

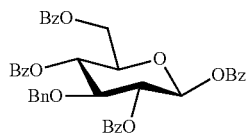

1,2,4,6-tetra-O-benzoyl-3-O-benzyl-β-D-glucopyranoside (7-23)

The synthesis was accomplished with the modified procedure followed in Carbohydr. Res, 1998, 305, 293-303. To an ice-cooled solution of 1,2;5,6-di-O-isopropylidene-α-D-glucofuranose (7-20) (30.0 g, 115.3 mmol) in dry DMF (100 mL) was added 60 wt % NaH (9.2 g, 230.6 mmol) and stirred at 0° C. for 30 min. Then benzyl bromide (29.5 g, 173 mmol) was added dropwise and the solution was warmed at room temperature. After stirring for 14 h, crushed ice was added and the mixture was diluted with water, extracted with ether and washed with water and brine successively. The solution was dried over $Na_2SO_4$, filtered, concentrated to obtain 7-21, The crude was taken for next step without further purification. A solution of 7-21 in a mixture of EtOH:THF:H2O (2:2:5/v, 130 mL) was stirred with Dowex 50 resin (H$^+$ form, 25 g) for 12 h at 75° C. Then, the resin was filtered off and the filtrate was quenched with trimethylamine. The solvent was evaporated and further coevaporated twice with toluene to obtain 7-22 as a white solid. The solid was then dissolved in DCM (150 mL) and were added trimethylamine (83 g, 821.6 mmol), DMAP (6.25 g, 51.3 mmol) and then cooled at 0° C. Benzoyl chloride (60 mL, 616.2 mmol) was added slowly and stirred for additional 14 h at room temperature. The mixture was diluted with DCM, washed with 2 M HCl, saturated $NaHCO_3$ solution and brine, and dried over $Na_2SO_4$. Evaporation of the solvent and dissolution of the residue in MeOH resulted in crystallized product 7-23 (47.5 g, 60% over 2 steps). $^1$H NMR (400 MHz, $CDCl_3$): δ 8.02-7.97 (m, 8H), 7.60-7.49 (m, 4H), 7.45-7.35 (m, 8H), 7.07-7.00 (m, 5H), 6.17 (d, 1H, J=7.6 Hz), 5.73 (dd, 1H, J=7.6 Hz, 7.6 Hz), 5.71 (dd, 1H, J=8.8 Hz, 8.8 Hz), 4.67 (d, 1H, J=11.6 Hz), 4.64 (dd, 1H, J=11.6 Hz), 4.61 (dd, 1H, J=12 Hz, 3.2 Hz), 4.43 (dd, 1H, J=12 Hz, 4.8 Hz), 4.25 (ddd, 1H, J=12 Hz, 4.8 Hz, 3.2 Hz), 4.19 (dd, 1H, J=8.4 Hz, 8.4 Hz).

Example 18

1,2,4,6-tetra-O-benzoyl-β-D-glucopyranoside (7-11)

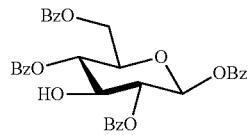

1,2,4,6-tetra-O-benzoyl-β-D-glucopyranoside (7-11)

Compound was reported in *J. Carbohydr. Res.* 1970, 15, 263-270; *Can. J Chem.* 1964, 42, 2560-256.

Compound 7-23 (20 g, 29.1 mmol) was dissolved in 250 mL of THF and the flask was kept under vacuum and then purged with nitrogen. After repeating the process for three times, Pd(OH)$_2$/C (3 g) was added and then flushed with H$_2$-gas (balloon). The mixture was stirred at room temperature for 24 h and then filtered through a bed of Celite. The solvent was evaporated and the syrupy residue was recrystallized from hot MeOH to obtain 7-11 as a white solid (15.9 g, 91% yield). $^1$H NMR (400 MHz, $CDCl_3$): δ 8.04-7.99 (m, 8H), 7.57-7.49 (m, 4H), 7.44-7.34 (m, 8H), 7.07-7.00 (m, 5H), 6.20 (d, 1H, J=8 Hz), 5.60 (dd, 1H, J=8.8 Hz, 8.8 Hz), 5.53 (dd, 1H, J=8.8 Hz, 8.8 Hz), 4.64 (dd, 1H, J=12 Hz, 2.4 Hz), 4.46 (dd, 1H, J=12 Hz, 4.8 Hz), 4.31-4.25 (m, 2H), 3.12 (d, 1H, J=6 Hz).

Example 19

Procedure A: General Procedure for Template Directed 1,2-Cis Redox Glycosylation:

A solution of C-2 NAP thioglycoside donor (1.2 eq) and acceptor (1.0 eq) in dry DCM (0.1 M) was charged with 4 Å molecular sieves (total mass eq.) and stirred at room temperature for 40 min. Then DDQ (1.2 eq) was added and the brown mixture was further stirred for 2 h. [In some occasion, the reaction mixture was then filtered through Celite and quenched with ascorbic acid buffer (pH=7.2). The aqueous layer was extracted with DCM (3 times) and the combined organic layer was washed with saturated $NaHCO_3$ solution, brine, then dried over $Na_2SO_4$, filtered, and concentrated. The crude was directly used for next step]. To the reaction mixture was added $K_2CO_3$ (3 eq.) and the mixture was stirred for 15 min before adding a solution of Ar$_3$N$^+$ SbCl$_6^-$ (BAHA) (1.5 eq) in acetonitrile. The mixture was stirred for another 35 min and the color changed from dark blue to brown to muddy. Mixture was quenched with excess trimethylamine, filtered thru Celite, and evaporated. Flash chromatographic purification afforded 1,2-cis glycosylated products.

Example 20

Trichloroacetimido 3,4-di-O-benzyl-α-D-xylopyranosyl-(1→3)-2,4,6-tri-O-benzoyl-α-D-glucopyranoside (7-30)

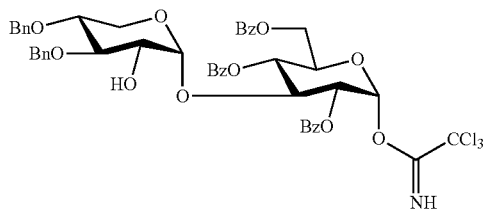

Trichloroacetimido 3,4-di-O-benzyl-α-D-xylopyranosyl-(1→3)-2,4,6-tri-O-benzoyl-α-D-glucopyranoside (7-30): Donor 7-10 and acceptor 7-11 was subjected to procedure A to obtain the disaccharide 7-25 in 61% yield over 2 steps. 7-25 (3.3 g, 3.27 mmol) was dissolved in a mixture of MeOH/THF (3:7/v, 60 mL) and then cooled in an ice-bath. NH$_3$-gas was bubbled into the mixture for 30 min and then the pale-yellow solution was left to stir for additional 16 h while attaining the room temperature. Air was bubbled to remove excess ammonia and solvent was removed under reduced pressure. The crude residue was then dissolved in dry DCM (40 mL) followed by addition of DBU (0.245 g, 1.62 mmol) and CCl$_3$CN (1.65 mL, 16.3 mmol), After stirring at room temperature for 45 min, the solvent was evaporated and crude was purified by flash chromatography to obtain 7-30 as a white foamy solid (2.58 g, 75% yield over 2 steps). $^1$H NMR: (400 MHz, CDCl$_3$) δ 8.59 (s, 1H), 8.07-8.00 (m, 7H), 7.57-7.55 (m, 4H), 7.44-7.40 (m, 7H), 7.30-7.20 (m, 5H), 7.05-7.03 (m, 2H), 6.72 (d, 1H, 3.6 Hz), 5.73 (dd, 1H, J=9.6 Hz, 9.6 Hz), 5.50 (dd, 1H, J=10 Hz, 4 Hz), 4.97 (d, 1H, J=3.6 Hz), 4.72 (d, 1H, J=11.6 Hz), 4.61 (d, 1H, J=11.6 Hz), 4.59 (d, 1H, 0.1=11.6 Hz), 4.55 (d, 1H, J=11.6 Hz), 4.49 (ddd, 1H, J=10.4 Hz, 4.8 Hz, 2 Hz), 4.41 (dd, 1H, J=7.2 Hz, 7.2 Hz), 4.40 (dd, 1H, J=11.6 Hz, 5.6 Hz), 4.28 (d, 1H, J=6.8 Hz), 3.48 (dd, 1H, 1=8.8 Hz, 8.8 Hz), 3.42 (dd, 1H, J=10 Hz, 10 Hz), 3.34-3.29 (m, 2H), 3.24 (ddd, 1H, J=10 Hz, 5.2 Hz, 5.2 Hz), 1.84 (d, 1H, 7.2 Hz).

Example 21

(2-azidoethyl) 3,4-di-O-benzyl-α-D-xylopyranosyl-(1→3)-2,4,6-tri-O-benzoyl-β-D-glucopyranoside (7-32)

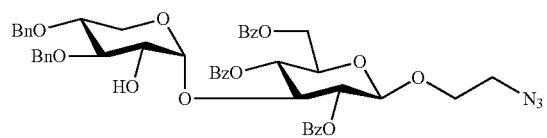

(2-azidoethyl) 3,4-di-O-benzyl-α-D-xylopyranosyl-(1→3)-2,4,6-tri-O-benzoyl-β-D-glucopyranoside (7-32): Trichloroacetimidate donor 7-30 (0.15 g, 0.158 mmol) and 2-azidoethanol (7-31) (0.024 g, 0.276 mmol) were dissolved together in dry DCM (5 mL) and 4 Å molecular sieves (0.15 g) was added. The mixture was stirred for 45 min before cooling down in an ice-bath. A solution of TMSOTf (6 μL, 0.021 mmol) in dry DCM (0.1 mL) was added dropwise and then the warmed at room temperature. After 90 min, the reaction was quenched with a few drops of triethylamine, diluted with DCM, and filtered through Celite. Upon evaporation of solvent and flash chromatographic purification target product (7-32) was obtained in 83% yield. $^1$H NMR (400 MHz, CDCl$_3$) δ 8.09-8.07 (m, 2H), 8.02-7.99 (m, 4H), 7.57-7.52 (m, 3H), 7.45-7.38 (m, 7H), 7.25-7.20 (m, 7H), 7.09-7.07 (m, 2H), 5.62 (dd, 1H, J=9.6 Hz, 9.6 Hz), 5.35 (dd, 1H, J=8 Hz, 8.4 Hz), 4.88 (d, 1H, J=4 Hz), 4.82 (d, 1H, J=8 Hz), 4.71 (d, 1H, 5=11.2 Hz), 4.63 (d, 1H, J=12 Hz), 4.62 (d, 1H, J=12 Hz), 4.43 (dd, 1H, J=11.4 Hz, 5.2 Hz), 4.41 (d, 1H, J=11.6 Hz), 4.30 (dd, 1H, J=11.2 Hz, 11.2 Hz), 4.29 (d, 1H, J=12 Hz), 4.04-3.99 (m, 2H), 3.69 (ddd, 1H, J=10 Hz, 5.6 Hz, 3.2 Hz), 3.50 (dd, 1H, J=9.2 Hz, 9.2 Hz), 3.43-3.37 (m, 2H), 3.31-3.25 (m, 3H), 3.17 (dd, 1H, J=10.4 Hz, 4.8 Hz), 1.88 (d, 1H, 7.2 Hz). $^{13}$C NMR: (125 MHz, CDCl$_3$) δ 166.1, 165.5, 165.1, 138.6, 138.1, 133.5, 133.1(2), 129.9, 129.8, 128.5, 128.4, 128.3, 128.2, 127.8, 127.5(2), 101.1, 100.8, 81.1, 80.0, 77.2, 77.1, 75.1, 72.7, 72.5, 72.1, 71.9 (2), 71.0, 68.0, 63.0, 61.0, 50.6.

Example 22

(2-azidoethyl) 3,4-di-O-benzyl-α-D-xylopyranosyl-(1→3)-β-D-glucopyranoside (7-33)

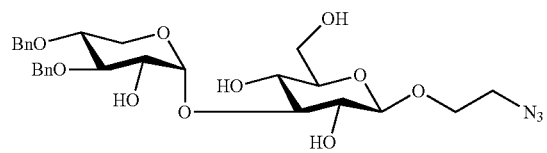

(2-azidoethyl) 3,4-di-O-benzyl-α-D-xylopyranosyl-(1→3)-β-D-glucopyranoside (7-33): Under N$_2$ atmosphere, to a solution of 7-32 (0.1 g, 0.102 mmol) in a mixture of dry MeOH/DCM (2:1/v, 3 mL) was added sodium methoxide (0.002 g, 0.037 mmol) at ambient temperature. The mixture was warmed at 40° C. and stirred for 12 hours. Thereupon, the reaction mixture was concentrated and crude residue was purified by flash chromatography to obtain 7-33 in 81% yield. $^1$H NMR: (400 MHz, MeOD) δ 7.41-7.27 (m, 10H), 5.21 (d, 1H, J=3.6 Hz), 4.85 (d, 1H, J=11.6 Hz), 4.68 (d, 1H, J=12 Hz), 4.65 (d, 1H, J=12 Hz), 4.36 (d, 1H, J=8 Hz), 4.04 (ddd, 1H, J=7.2 Hz, 5.2 Hz, 5.2 Hz), 3.97 (dd, 1H, J=11.4 Hz, 11.4 Hz), 3.89 (dd, 1H, J=12 Hz, 2 Hz), 3.78 (dd, 1H, J=7.2 Hz, 6.8 Hz), 3.75 (dd, 1H, J=5.6 Hz, 5.6 Hz), 3.73 (dd, 1H, J=6.8 Hz, 6.8 Hz), 3.71 (dd, 1H, J=7.2 Hz, 3.2 Hz), 3.69 (dd, 1H, J=6.4 Hz, 2.4 Hz), 3.61-3.52 (m, 3H), 3.53-3.49 (m, 2H), 3.48 (dd, 1H, J=5.2 Hz, 5.2 Hz), 3.36 (1H, overlapped with solvent). $^{13}$C NMR: (125 MHz, MeOD) δ 140.4, 139.8, 130.8, 129.3, 129.2(2), 129.1, 128.9, 128.8, 128.7, 128.5, 104.6, 101.6, 85.7, 82.9, 79.2, 77.6, 76.2, 74.1, 74.0, 73.6, 71.8, 71.0, 69.4, 62.5, 61.5, 52.0.

Example 23

(2-azidoethyl) 3,4-di-O-benzyl-α-D-xylopyranosyl-(1→3)-β-D-glucuronopyranoside methyl ester (7-35)

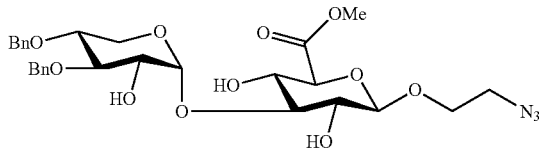

(2-azidoethyl) 3,4-di-O-benzyl-α-D-xylopyranosyl-(1→3)β-D-glucuronopyranoside methyl ester (7-35): To a vigorously stirred solution of 7-33 (0.06 g, 0.106 mmol) in a mixture of DCM/H$_2$O (2:1/v, 2.5 mL) were added TEMPO (4 mg, 0.022 mmol) and BAIB (0.086 g, 0.267 mmol). Stirring was continued for 1.5 h at room temperature and the reaction mixture was quenched with 3 mL of 10% Na$_2$S$_2$O$_3$ solution. Aqueous layer was extracted with EtOAc (20×3 mL) and combined organic layer was dried over MgSO$_4$, filtered, and concentrated under reduced pressure to obtain crude 7-34.

The crude acid was then dissolved in dry DMF (2.5 mL) followed by addition of K$_2$CO$_3$ (0.03 g, 0.212 mmol) and methyl iodide (0.06 g, 0.424 mmol). The mixture was stirred for 14 h and then diluted with water (10 mL), extracted with EtOAc (20×3 mL). Combined organic layer was dried over Na$_2$SO$_4$, filtered, and concentrated. After flash chromatography, pure 7-35 was obtained in 61% yield over 2 steps. $^1$H NMR: (400 MHz, CDCl$_3$) δ 7.35-7.29 (m, 10H), 5.01 (d, J=3.6 Hz), 4.92 (d, 1H, 3=11.2 Hz), 4.77 (d, 1H, 3=11.2 Hz), 4.69 (d, 1H, J=11.6 Hz), 4.61 (d, 1H, J=11.6 Hz), 4.40 (d, 1H, J=7.2 Hz), 4.08 (ddd, 1H, J=11.2 Hz, 5.6 Hz, 4 Hz), 3.98 (bs, 1H), 3.89-3.87 (m, 2H), 3.83 (s, 3H), 3.81-3.85 (m, 1H), 3.79-3.74 (m, 3H), 3.69-3.68 (m, 1H), 3.60-3.53 (m, 2H), 3.52-3.48 (m, 2H), 3.41 (ddd, 1H, J=10.4 Hz, 5.2 Hz, 3.6 Hz), 3.14 (bs, 1H), 2.94 (bs, 1H). $^{13}$C NMR: (125 MHz, CDCl$_3$) δ 169.2, 138.4, 137.8, 128.5, 127.9(2), 127.8(2), 103.2, 101.2, 86.7, 80.7, 77.2, 77.1, 75.0, 74.2, 73.1, 72.0, 70.9, 68.9, 61.5, 52.8, 50.6.

Example 24

4-O-benzoyl-2,3-O-isopropylidene-α-D-xylopyranosyl-(1→3)-1,2,4,6-tetra-O-benzoyl-β-D-glucopyranoside (7-44)

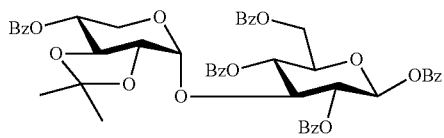

4-O-benzoyl-2,3-O-isopropylidene-α-D-xylopyranosyl-(1→3)-1,2,4,6-tetra-O-benzoyl-β-D-glucopyranoside (7-44): Compound 7-25 (0.75 g, 0.77 mmol) was dissolved in 30 mL of MeOH/EtOAc/THF (1:3:1/v) and the flask was kept under vacuum followed by purging with nitrogen. After repeating the process for three times, Pd(OH)$_2$/C (0.1 g) was added and then flushed with H$_2$-gas (balloon). The mixture was stirred at room temperature for 24 h and then filtered through a bed of Celite to obtain crude 7-41 as a white solid.

A solution of 7-41 was prepared in dry DMF (12 mL) and were added p-toluenesulfonic acid (9 mg, 0.038 mmol) and 2,2-dimethoxypropane (7-42) (0.78 g, 7.7 mmol). The mixture was heated at 70° C. and stirred for 3 h and then cooled down to room temperature, quenched with a few drops of trimethylamine. Solvent was evaporated under reduced pressure and purified by flash chromatography to afford 7-43 (0.36 g) in 61% overall yield.

To a solution of 7-43 (0.36 g, 0.47 mmol) in dry DCM (6 mL) were added trimethylamine (0.13 mL, 0.94 mmol) and DMAP (0.029 g, 0.23 mmol), The mixture was cooled in an ice-bath and benzoyl chloride (0.08 mL, 0.7 mmol) was added dropwise. The mixture was warmed at room temperature and stirred for additional 8 h. The solution was then diluted with DCM, poured into ice-water, extracted with DCM (10×3 mL). Combined organic layer was washed with brine, dried over Na$_2$SO$_4$, filtered, and evaporated. Flash chromatographic purification yielded 7-44 in 82% yield. $^1$H NMR: (400 MHz, CDCl$_3$) δ 8.02-7.95 (m, 12H), 7.58-7.31 (m, 13H), 6.14 (d, 114, J=8 Hz), 5.75 (dd, 1H, J=8.4 Hz, 8.4 Hz), 5.68 (dd, 1H, J=9.6 Hz, 9.6 Hz), 5.27 (d, 1H, J=2.8 Hz), 5.06 (ddd, 1H, J=12 Hz, 9.6 Hz, 4.8 Hz), 4.59 (dd, 1H, J=12 Hz, 3.2 Hz), 4.46 (dd, 1H, J=12 Hz, 5.2 Hz), 4.38 (dd, 1H, J=8.8 Hz, 8.8 Hz), 4.23 (ddd, 1H, J=10 Hz, 4.4 Hz, 4.4 Hz), 4.07 (dd, 1H, J=9.6 Hz, 9.6 Hz), 3.54 (dd, 1H, J=11.2 Hz, 5.6 Hz), 3.35 (d, 1H, J=10.4 Hz), 3.30 (dd, 1H, J=8.8 Hz, 2.8 Hz), 1.05 (s, 3H), 1.03 (s, 3H). $^{13}$C NMR: (125 MHz, CDCl$_3$) δ 166.1, 165.5, 165.3, 165.0, 164.6, 133.7, 133.4, 133.2(2), 133.0, 130.1, 130.0, 129.9, 129.8, 129.7, 129.6, 129.5, 129.3, 128.5, 128.4, 128.2, 128.0, 110.89, 99.6, 92.7, 82.2, 77.2, 75.5, 73.2, 73.1, 71.6, 71.3, 70.1, 63.0, 60.3, 26.4, 25.8.

Example 25

Trichloroacetimido 4-O-benzoyl-2,3-O-isopropylidene-α-D-xylopyranosyl-(1→3)-2,4,6-tri-O-benzoyl-α-D-glucopyranoside (7-46)

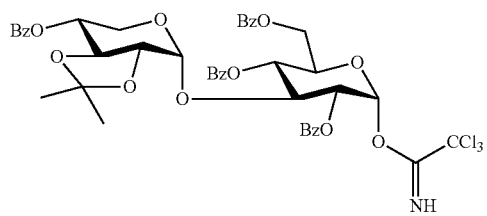

Trichloroacetimido 4-O-benzoyl-2,3-O-isopropylidene-α-D-xylopyranosyl-(1→3)-2,4,6-tri-O-benzoyl-α-D-glucopyranoside (7-46): Compound 7-44 (0.2 g, 0.23 mmol) was dissolved in a mixture of MeOH/THF (3:7/v, 6 mL) and then cooled in an ice-bath. NH$_3$-gas was bubbled into the mixture for 20 min and then the pale-yellow solution was left to stir for additional 6 h while attaining the room temperature. Air was bubbled to remove excess ammonia and solvent was removed under reduced pressure. The crude residue was then dissolved in dry DCM (4 mL) followed by addition of DBU (0.018 g, 0,106 mmol) and CCl₃CN (0.12 mL, 1.15 mmol). After stirring at room temperature for 1 h, the solvent was evaporated and crude was purified by flash chromatography to obtain 7-46 (0.126 g) in 60% yield over 2 steps. $^1$H NMR: (300 MHz, CDCl$_3$) δ 8.59 (s, 1H), 8.06-7.90 (m, 8H), 7.57-7.33 (m, 12H), 6.70 (d, 1H, J=3.9 Hz), 5.65 (dd, 1H, J=9.6 Hz, 9.6 Hz), 5.55 (dd, 1H, J=9.6 Hz, 3.9 Hz), 5.31 (d, 1H, J=3 Hz), 5.06 (ddd, 1H, J=10.2 Hz, 9.6 Hz, 5.1 Hz), 4.58 (dd, 1H, J=9.9 Hz, 9.9 Hz), 4.54-4.39 (m, 3H), 4.02 (dd, 1H, J=9.6 Hz, 9.6 Hz), 3.53 (dd, 1H, J=11.1 Hz, 5.4 Hz), 3.29 (dd, 1H, J=9.9 Hz, 2.7 Hz), 3.27 (d, 1H, J=11.1 Hz), 1.06 (s, 3H), 1.01 (s, 3H).

Example 26

(2-azidoethyl) 4-O-benzoyl-α-D-xylopyranosyl-(1→3)-2,4,6-tri-O-benzoyl-β-D-glucopyranoside (7-47)

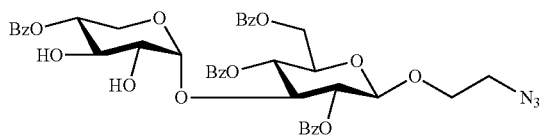

(2-azidoethyl) 4-O-benzoyl-α-D-xylopyranosyl-(1→3)-2,4,6-tri-O-benzoyl-β-D-glucopyranoside (7-47): Trichloroacetimidate donor 7-46 (0.1 g, 0.11 mmol) and 2-azidoethanol (7-31) (0.015 g, 0,165 mmol) were dissolved together in dry DCM (3 mL) and 4 Å molecular sieves (0.1 g) was added. The mixture was stirred for 45 min before cooling down in an ice-bath. A solution of TMSOTf (3 μL, 0.02 mmol) in dry DCM (0.05 mL) was added dropwise and then the warmed at room temperature. After 1 h, the reaction was quenched with a few drops of triethylamine, diluted with DCM, and filtered through Celite. Upon evaporation of solvent and flash chromatographic purification, target product 7-47 was obtained in 80% yield. $^1$H NMR: (400 MHz, CDCl$_3$) δ 8.03-7.99 (m, 6H), 7.86-7.84 (m, 2H), 7.57-7.53 (m, 3H), 7.46-7.38 (m, 7H), 7.32-7.25 (m, 2H), 5.65 (dd, 1H, J=9.6 Hz, 9.6 Hz), 5.40 (dd, 1H, J=8 Hz, 8 Hz), 4.97 (d, 1H, J=3.6 Hz), 4.81 (d, 1H, J=8 Hz), 4.78 (ddd, 1H, J=11.6 Hz, 10 Hz, 5.6 Hz), 4.62 (dd, 11-1, 0.1=12 Hz, 2.8 Hz), 4.44 (dd, 1H, J=12 Hz, 5.2 Hz), 4.33 (dd, 1H, J=8.8 Hz, 8.8 Hz), 4.12-4.02 (m, 1H), 3.99 (ddd, 1H, J=10.8 Hz, 4.8 Hz, 4.8 Hz), 3.86 (dd, 1H, J=9.2 Hz, 9.2 Hz), 3.69 (ddd, 1H, J=10.8 Hz, 8 Hz, 4 Hz), 3.46 (dd, 1H, J-=10.8 Hz, 10.8 Hz), 3.42-3.25 (m, 4H), 2.55 (d, 1H, J=2.4 Hz) (Xyl-C-3-OH), 2.03 (s, 1H) (Xyl-C-2-OH). $^{13}$C NMR: (125 MHz, CDCl$_3$) δ 166.1, 165.8, 165.2, 133.7, 133.3, 133.2, 133.1, 129.8, 129.7(2), 129.6, 129.5, 129.3, 128.9, 128.6, 128.3, 128.2, 101.1, 100.3, 79.9, 77.2, 72.5, 72.3, 72.0, 71.8, 71.3, 71.2, 68.1, 62.9, 59.4, 50.6.

Example 27

(2-azidoethyl) D-xylopyranosyl-α-(1→3)-β-D-glucopyranoside (7-49)

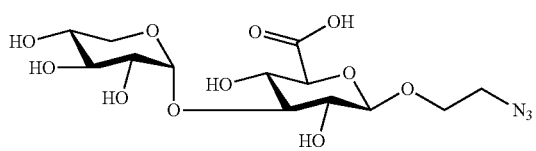

(2-azidoethyl) D-xylopyranosyl-α-(1→3)-β-D-glucopyranoside (7-49): To a solution of 7-47 (0.14 g, 0.176 mmol) in a mixture of MeOH/THF/H$_2$O (1:2:1/v, 8 mL) was added a solution of NaOH (0.1 g, 2.63 mmol) in water (1 mL). The mixture was stirred at room temperature for 24 h and then solvent was lyophilized. The crude residue 7-48 was directly without further purification.

Compound 7-48 was dissolved in water (1.8 mL) and were added TEMPO (2.6 mg, 0.016 mmol) and sodium bromide (0.012 g, 0.088 mmol). The mixture was cooled at 0° C. and a solution of NaOCl (0.6 mL, 5% w/v in water) was added followed by a drop of 0.5 M NaOH to maintain pH 10 (additional drops needed if pH dropped). The stirring was continued for 90 min and then the reaction mixture was quenched with MeOH. Crude was purified by P-2 biogel affinity column with water as eluent. $^1$H NMR: (600 MHz, D$_2$O) δ 5.33 (d, 1H, J=3.6 Hz), 4.52 (d, 1H, J=8.4 Hz), 4.06 (ddd, 1H, J=12 Hz, 4.8 Hz, 4.8 Hz), 3.89 (dd, 1H, J=10.8 Hz, 10.8 Hz), 3.84 (ddd, 1H, J=10.2 Hz, 4.2 Hz, 4.2 Hz), 3.77-3.71 (m, 3H), 3.68 (dd, 1H, J=9 Hz, 9 Hz), 3.65 (m, 2H), 3.60 (ddd, 1H, J=9 Hz, 4.2 Hz, 3.6 Hz), 3.56-3.53 (m, 2H), 3.52 (dd, 1H, J=10.2 Hz, 6 Hz), 3.43 (dd, 9 Hz, 7.8 Hz). $^{13}$C NMR: (150 MHz, D$_2$O) δ 181.5, 102.3, 98.8, 81.2, 76.0, 73.0, 72.4, 71.6, 71.5, 69.4, 69.1, 68.5, 61.4, 50.5, 50.2.

Example 28

(2-azidoethyl) 4-O-benzoyl-α-D-xylopyranosyl-(1→3)-2,4,6-tri-O-benzoyl-β-D-glucopyranosyl-(1→3)-4-O-benzoyl-α-D-xylopyranosyl-(1→3)-2,4,6-tri-O-benzoyl-β-D-glucopyranoside (7-50)

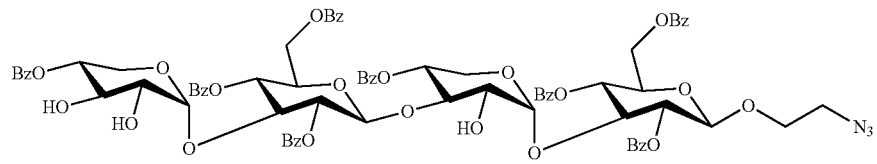

(2-azidoethyl) 4-O-benzoyl-α-D-xylopyranosyl-(1→3)-2,4,6-tri-O-benzoyl-β-D-glucopyranosyl-(1→3)-4-O-benzoyl-α-D-xylopyranosyl-(1→3)-2,4,6-tri-O-benzoyl-β-D-glucopyranoside (7-50): Trichloroacetimidate disaccharide donor 7-46 (0.085 g, 0.095 mmol) and disaccharide acceptor 7-47 (0.095 g, 0.120 mmol) were dissolved together in dry DCM (5 mL) and 4 Å molecular sieves (0.18 g) was added. The mixture was stirred for 45 min before cooling down in an ice-bath. A solution of TMSOTf (2.5 µL, 0.015 mmol) in dry DCM (0.05 mL) was added dropwise and then the warmed at room temperature. After 2 h, the reaction was quenched with a few drops of triethylamine, diluted with DCM, and filtered through Celite. To the filtrate was added 2 mL of MeOH and Dowex H+ resin (0.12 g), further stirred for 12 h at room temperature. Thereupon, the mixture was filtered and solvent was evaporated before purification by flash chromatography tetrasaccharide 7-50 was obtained in 54% yield (79% brsm) yield. $^1$H NMR: (600 MHz, CDCl$_3$) δ 8.03-7.93 (m, 8H), 7.86 (d, 2H, J=7.8 Hz), 7.83 (d, 2H, J=7.8 Hz), 7.77 (d, 2H, J=7.8 Hz), 7.62-7.29 (m, 20H), 7.24-7.21 (m, 4H), 7.06 (t, 2H, J=7.8 Hz), 5.55 (dd, 1H, J=9 Hz, 9 Hz), 5.47 (dd, 1H, J=9 Hz, 9 Hz), 5.37 (dd, 1H, J=9 Hz, 9 Hz), 5.21 (dd, 1H, J=9 Hz, 9 Hz), 4.93 (d, 1H, J=7.8 Hz), 4.90 (d, 1H, J=3.6 Hz), 4.81 (d, 1H, J=3.6 Hz), 4.79 (d, 1H, J=8 Hz), 4.78-4.72 (m, 2H), 4.57 (dd, 1H, J=11.4 Hz, 2.4 Hz), 4.43 (dd, 1H, J=12 Hz, 5.4 Hz), 4.34 (dd, 1H, J=12 Hz, 3 Hz), 4.28 (dd, 1H, J=12 Hz, 4.8 Hz), 4.22 (dd, 1H, J=9 Hz, 9 Hz), 4.17 (dd, 1H, J=9 Hz, 9 Hz), 4.03-3.99 (m, 3H), 3.93 (dd, 1H, J=9 Hz, 9 Hz), 3.75 (dd, 1H, J=9 Hz, 9 Hz), 3.71-3.66 (m, 1H), 3.45-3.41 (m, 2H), 3.38 (dd, 1H, J=11.4 Hz, 6.6 Hz), 3.31 (dd, 1H, J=12 Hz, 9 Hz), 3.30-3.26 (m, 3H), 3.18 (dd, 1H, J=9.6 Hz, 3.6 Hz), 2.42 (bs, 1H), 1.89 (d, 1H, J=2.4 Hz), 1.76 (d, 1H, J=3.6 Hz). $^{13}$C NMR: (150 MHz, CDCl$_3$) δ 166.1(2), 165.8, 165.6, 165.3, 165.2, 165.1, 133.7, 133.6, 133.2(2), 133.1, 133.0(2), 129.8(2), 129.7(2), 129.5(2), 129.4, 129.3(2), 128.9, 128.6, 128.4, 128.3(2), 128.2, 128.1, 101.6, 101.1, 100.5, 99.9, 80.0, 79.7, 79.0, 72.6, 72.4, 72.2, 72.0, 71.7, 71.2(2), 70.9, 68.8, 68.2, 63.1, 63.0, 59.6, 59.3, 50.6.

Example 29

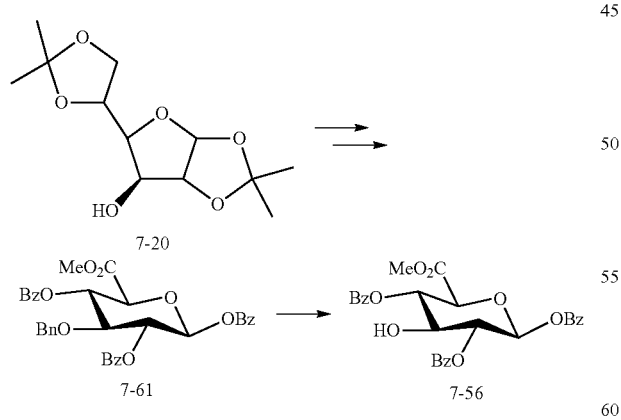

The synthesis of 7-56 was accomplished from commercially available 1,2;5,6-di-O-isopropylidene-α-D-glucofuranose (7-20) following the modified procedure described in *Tetrahedron* 2006, 62, 563-577. 1,2,4-tri-O-benzoyl-3-O-benzyl-β-D-glucuronopyranoside methyl ester (7-61): NMR: (400 MHz, CDCl$_3$) δ 8.03-7.94 (m, 6H), 7.62 (t, 1H, J=6.4 Hz), 7.54-7.33 (m, 8H), 7.15-7.12 (m, 5H), 6.25 (d, 1H, J=7.2 Hz), 5.81 (dd, 1H, J=7.2 Hz, 7.2 Hz), 5.65 (dd, 1H, J=6.8 Hz, 6.8 Hz), 4.77 (d, 1H, J=11.6 Hz), 4.70 (d, 1H, J=11.6 Hz), 4.52 (d, 1H, J=11.6 Hz), 4.25 (dd, 1H, J=7.2 Hz, 7.2 Hz), 3.50 (s, 3H). 1,2,4-tri-O-benzoyl-β-D-glucuronopyranoside methyl ester (7-56): NMR: (400 MHz, CDCl$_3$) δ 8.10-7.94 (m, 5H), 7.56-7.36 (m, 10H), 6.23 (d, 1H, J=8 Hz), 5.56 (dd, 1H, J=8.4 Hz, 8.4 Hz), 5.51 (dd, 1H, J=8 Hz, 8 Hz), 4.48 (d, 1H, J=9.8 Hz), 4.33 (ddd, 1H, J=8.4 Hz, 8.4 Hz, 2.4 Hz), 3.63 (s, 3H), 3.15 (d, 1H, J=2.4 Hz).

Example 30

4-O-benzoyl-2,3-O-isopropylidene-α-D-xylopyranosyl-(1→3)-1,2,4-tri-O-benzoyl-β-D-glucuronopyrano-side (7-55)

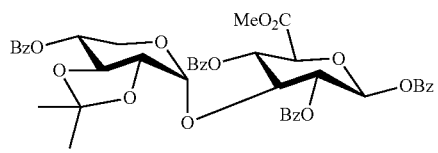

4-O-benzoyl-2,3-O-isopropylidene-α-D-xylopyranosyl-(1→3)-1,2,4-tri-O-benzoyl-β-D-glucuronopyrano-side (7-55): Donor 7-10 (3 g) and acceptor 7-56 (2.02 g) was subjected to procedure A to obtain disaccharide 7-63 (intermediate mixed acetal 7-62 was purified, 81% yield). Thereafter, the reaction sequence described to synthesize 7-44 was followed to obtain compound 7-55. Final product was purified by flash chromatography. $^1$H NMR: (500 MHz, CDCl$_3$) δ 8.07-7.94 (m, 7H), 7.59-7.29 (m, 13H), 6.14 (d, 1H, J=7.5 Hz), 5.68 (dd, 1H, J=9 Hz, 9 Hz), 5.62 (dd, 1H, 3=9 Hz, 5 Hz), 5.30 (d, 1H, J=3 Hz), 5.08 (ddd, 1H, J=10.5 Hz, 5.5 Hz, 4 Hz), 4.63 (dd, 1H, J=10 Hz, 4.5 Hz), 4.41 (d, 1H, J=9.5 Hz), 4.06 (dd, 1H, J=10 Hz, 10 Hz), 3.67 (s, 3H), 3.54 (dd, 1H, J=10 Hz, 5.5 Hz), 3.31 (dd, 1H, J=9.5 Hz, 3.5 Hz), 3.27 (dd, 1H, J=11 Hz, 11 Hz), 1.11 (s, 3H), 1.04 (s, 3H). $^{13}$C NMR: (125 MHz, CDCl$_3$) δ 167.0, 165.4, 165.2, 165.1, 164.6, 133.9, 133.5, 133.4, 133.2, 130.2, 129.9, 129.8, 129.7, 129.6(2), 129.5, 129.3, 128.7, 128.5, 128.4, 128.3, 128.2, 99.6, 92.3, 81.2, 78.5, 75.5, 73.3, 71.3, 71.0, 70.8, 70.1, 60.4, 53.0, 26.4, 25.9.

Example 31

Trichloroacetimido 4-O-benzoyl-2,3-O-isopropylidene-α-D-xylopyranosyl-(1→3)-2,4-di-O-benzoyl-α-D-glucuronopyranoside methyl ester (7-67)

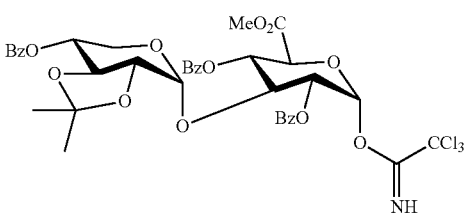

Trichloroacetimido 4-O-benzoyl-2,3-O-isopropylidene-α-D-xylopyranosyl-(1→3)-2,4-di-O-benzoyl-α-D-glucuronopyranoside methyl ester (7-67): Compound 7-55 (1.12 g, 1.4 mmol) was dissolved in a mixture of MeOH/THF (3:7/v, 40 mL) and then cooled in an ice-bath. NH$_3$-gas was bubbled into the mixture for 30 min and then the pale-yellow solution was left to stir for additional 7 h while attaining the room temperature. Air was bubbled to remove excess ammonia and solvent was removed under reduced pressure. The crude residue was then dissolved in dry DCM (40 mL) followed by addition of DBU (0.11 g, 0.7 mmol) and CCl$_3$CN (0.7 mL, 7 mmol). After stirring at room temperature for 1 h, the solvent was evaporated and crude was purified by flash chromatography to obtain 7-67 (0.68 g) in 58% yield over 2 steps. $^1$H NMR: (400 MHz, CDCl$_3$) δ 8.66 (s, 1H), 8.06-8.01 (m, 4H), 7.92-7.90 (m, 2H), 7.59-7.33 (m, 9H), 6.79 (d, 1H, J=3.6 Hz), 5.60 (dd, 1H, J=9.6 Hz, 9.6 Hz), 5.56 (dd, 1H, 0.1=9.6 Hz, 3.6 Hz), 5.34 (d, 1H, J=3.2 Hz), 5.06 (ddd, 1H, J=10 Hz, 10 Hz, 5.6 Hz), 4.60 (d, 1H, J=10.4 Hz), 4.59 (dd, 1H, J=9.6 Hz, 9.6 Hz), 4.01 (dd, 1H, J=9.6 Hz, 9.6 Hz), 3.67 (s, 3H), 3.55 (dd, 1H, J=11.2 Hz, 5.2 Hz), 3.29 (dd, 1H, J=9.6 Hz, 3.2 Hz), 3.23 (dd, 1H, J=10.4 Hz, 10.4 Hz), 1.10 (s, 3H), 1.01 (s, 3H). $^{13}$C NMR: (100 MHz, CDCl$_3$) δ 167.4, 165.4, 165.3, 165.2, 160.1, 133.6, 133.2, 130.1, 129.8, 129.7, 129.5, 129.2, 128.7, 128.4, 128.3, 1282, 110.9, 99.9, 93.1, 77.3, 75.4, 73.1, 71.1, 70.8, 70.7, 70.3, 60.3, 53.0, 26.3, 25.8.

Example 32

(2-azidoethyl) 4-O-benzoyl-α-D-xylopyranosyl-(1→3)-2,4-di-O-benzoyl-β-D-glucuronopyranoside methyl ester (7-68)

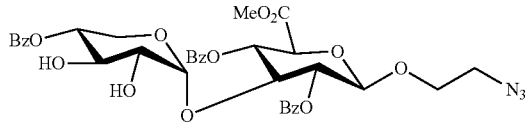

(2-azidoethyl) 4-O-benzoyl-α-D-xylopyranosyl-(1→3)-2,4-di-O-benzoyl-β-D-glucuronopyranoside methyl ester (7-68): Trichloroacetimidate donor 7-67 (0.25 g, 0.3 mmol) and 2-azidoethanol (7-31) (0.04 g, 0.45 mmol) were dissolved together in dry DCM (7 mL) and 4 Å molecular sieves (0.2 g) was added. The mixture was stirred for 45 min before cooling down in an ice-bath. A solution of TMSOTf (8 μL, 0.046 mmol) in dry DCM (0.05 mL) was added dropwise and then the warmed at room temperature. After 2 h, the reaction was quenched with a few drops of triethylamine, diluted with DCM, and filtered through Celite. Upon evaporation of solvent and flash chromatographic purification, target product 7-68 was obtained in 71% yield. $^1$H NMR: (500 MHz, CDCl$_3$) δ 8.03-8.00 (m, 4H), 7.88-7.86 (m, 2H), 7.60-7.29 (m, 9H), 5.70 (dd, 1H, J=9.5 Hz, 9.5 Hz), 5.39 (dd, 1H, J=8 Hz, 7 Hz), 5.04 (d, 1H, J=4 Hz), 4.87 (d, 1H, J=7 Hz), 4.82 (ddd, 1H, J=10 Hz, 10 Hz, 5.5 Hz), 4.35 (dd, 1H, J=8.5 Hz, 8.5 Hz), 4.30 (d, 1H, J=9 Hz), 4.08 (ddd, 1H, J=10 Hz, 3.5 Hz, 3.5 Hz), 185 (dd, 1H, J=9.5 Hz, 9.5 Hz), 3.73 (dd, 1H, J=9.5 Hz, 3.5 Hz), 3.69 (s, 3H), 3.50 (dd, 1H, J=10 Hz, 10 Hz), 3.48-3.40 (m, 2H), 3.39-3.31 (m, 2H), 2.61 (bs, 1H), 2.17 (d, 1H, J=2.5 Hz). $^{13}$C NMR: (125 MHz, CDCl$_3$) δ 167.6, 165.9, 165.8, 165.2, 133.7, 133.4, 133.2, 129.8 (2), 129.6, 129.3, 128.9, 128.6, 128.4, 128.3, 100.8, 100.1, 78.4, 72.7, 72.3, 72.2, 71.8, 71.3, 71.1, 68.4, 59.5, 52.9, 50.6.

Example 33

(2-azidoethyl) D-xylopyranosyl-α-(1→3)-β-D-glucopyranoside (7-49)

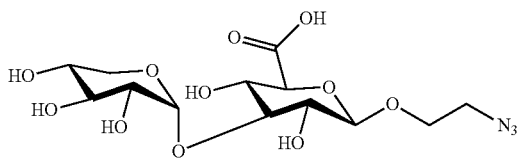

(2-azidoethyl) D-xylopyranosyl-α-(1→3)-β-D-glucopyranoside (7-49): To a solution of 7-68 (0.07 g, 0,088 mmol) in MeOH (10 mL) was added 4 N NaOH (0.33 mL) aqueous solution at 0° C. The mixture was stirred at room temperature for 24 h and then neutralized with 1 M HCl. The solvent was lyophilized and crude residue was purified by P-2 biogel affinity column with water as eluent. $^1$H NMR: (600 MHz, D$_2$O) δ 5.33 (d, 1H, J=3.6 Hz), 4.52 (d, 1H, J=8.4 Hz), 4.06 (ddd, 1H, J=12 Hz, 4.8 Hz, 4.8 Hz), 3.89 (dd, 1H, J=10.8 Hz, 10.8 Hz), 3.84 (ddd, 1H, J=10.2 Hz, 4.2 Hz, 4.2 Hz), 3.77-3.71 (m, 3H), 3.68 (dd, 1H, J=9 Hz, 9 Hz), 3.65 (m, 2H), 3.60 (ddd, 1H, J=9 Hz, 4.2 Hz, 3.6 Hz), 3.56-3.53 (m, 2H), 3.52 (dd, 1H, J=10.2 Hz, 6 Hz), 3.43 (dd, 9 Hz, 7.8 Hz). $^{13}$C NMR: (150 MHz, D$_2$O) δ 181.5, 102.3, 98.8, 81.2, 76.0, 73.0, 72.4, 71.6, 71.5, 69.4, 69.1, 68.5, 61.4, 50.5, 50.2.

Example 34

(2-azidoethyl) 4-O-benzoyl-α-D-xylopyranosyl-(1→3)-2,4-di-O-benzoyl-β-D-glucuronopyranosyl-(1→3)-4-O-benzoyl-α-D-xylopyranosyl-(1→3)-2,4-di-O-benzoyl-β-D-glucuronopyranoside methyl di-ester (7-69)

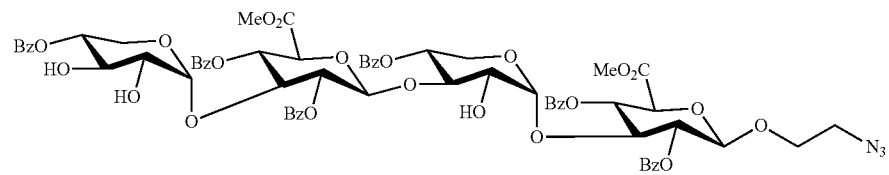

(2-azidoethyl) 4-O-benzoyl-α-D-xylopyranosyl-(1→3)-2,4-di-O-benzoyl-β-D-glucuronopyranosyl-(1→3)-4-O-benzoyl-α-D-xylopyranosyl-(1→3)-2,4-di-O-benzoyl-β-D-glucuronopyranoside methyl di-ester (7-69): Trichloroacetimidate disaccharide donor 7-67 (0.104 g, 0.125 mmol) and disaccharide acceptor 7-68 (0.06 g, 0.083 mmol) were were mixed together, coevaporated with toluene twice, and then dissolved together in dry DCM (3 mL). The mixture was cooled down in an ice-bath and a solution of TMSOTf (2 μL, 0.013 mmol) in dry DCM (0.1 mL) was added dropwise and then the solution was warmed at room temperature. After 2 h the TLC showed complete consumption of donor (acceptor wasn't fully consumed). The reaction mixture was diluted with MeOH (2 mL) and Dowex H$^+$ resin (0.1 g), further stirred for 8 h at room temperature. Thereupon, the mixture was filtered and solvent was evaporated before purification by flash chromatography to obtain tetrasaccharide 7-69 in 48% yield (79% brsm) yield. $^1$H NMR: (600 MHz, CDCl$_3$) δ 8.02-7.84 (m, 11H), 7.63-7.38 (m, 15H), 7.22 (t, 21-1, J=7.8 Hz), 7.12 (t, 2H, J=7.8 Hz), 5.66 (dd, 1H, J=8.4 Hz, 8.4 Hz), 5.54 (dd, 11-1, J=9 Hz, 9 Hz), 5.34 (dd, 1H, J=7.8 Hz, 7.8 Hz), 5.26 (dd, 1H, J=8.4 Hz, 8.4 Hz), 5.05 (d, 1H, J=7.8 Hz), 4.96 (d, 11-1, J=3.6 Hz), 4.87 (d, 1H, J=3.6 Hz), 4.84 (d, 1H, J=7.2 Hz), 4.76 (ddd, 1H, J=9.6 Hz, 9.6 Hz, 6 Hz), 4.69 (ddd, 1H, J=9.6 Hz, 9.6 Hz, 6 Hz), 4.27 (dd, 1H, J=9 Hz, 7.2 Hz), 4.24 (dd, 1H, J=9 Hz, 9 Hz), 4.17 (d, 1H, J=9.6 Hz), 4.08 (ddd, 1H, J=10.8 Hz, 6 Hz, 4.2 Hz), 3.94 (dd, 1H, J=9 Hz, 9 Hz), 3.76 (dd, 1H, J=9.6 Hz, 9.6 Hz), 3.71-3.69 (m, 1H), 3.68 (s, 3H), 3.52 (s, 3H), 3.48 (dd, 1H, J=10.8 Hz, 5.4 Hz), 3.43-3.39 (m, 2H), 3.37 (t, 2H, J=10.8 Hz), 3.35-3.28 (m, 3H), 3.25 (ddd, 1H, J=9 Hz, 9 Hz, 4.2 Hz), 2.42 (bs, 1H), 1.95 (d, 1H, J=7.8 Hz), 1.93 (bs, 1H). $^{13}$C NMR: (125 MHz, CDCl$_3$) δ 167.6, 166.0, 165.8, 165.7, 165.6, 165.5, 165.2(2), 133.7, 133.6, 133.4, 133.2, 133.1, 133.0, 130.0, 129.7, 129.5(2), 129.3, 129.2, 129.1, 128.9, 128.6(2), 128.3(2), 128.2, 101.4, 100.8, 100.0, 99.9, 79.1, 79.0, 78.0, 72.6, 72.3(2), 72.1, 71.9, 71.8, 71.1, 71.2, 71.0, 69.4, 68.5, 59.4, 59.3, 52.9, 52.6, 50.6.

Example 35

(2-azidoethyl) D-xylopyranosyl-α-(1→3)-β-D-glucuronopyranosyl-(1→3)-D-xylopyranosyl-α-(1→3)-β-D-glucuronopyranoside (7-52)

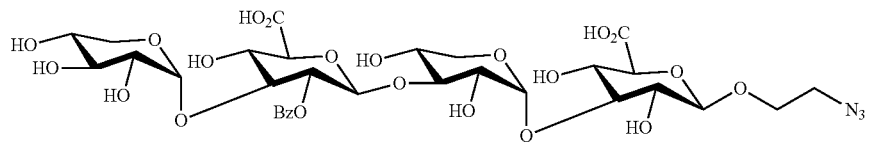

(2-azidoethyl) D-xylopyranosyl-α-(1→3)-β-D-glucuronopyranosyl-(1→3)-D-xylopyranosyl-α-(1→3)-β-D-glucuronopyranoside (7-52): To a solution of 7-69 (0.05 g, 0.036 mmol) in MeOH (15 mL) was added 4 N NaOH (0.36 mL) aqueous solution at 0° C. The mixture was stirred at room temperature for 24 h and then neutralized with 1 M HCl. The solvent was lyophilized and crude residue was purified by P-2 biogel affinity column with water as eluent to obtain 7-52 as a white foamy solid in 61% yield. $^1$H NMR: (600 MHz, D$_2$O) δ 5.30 (d, 1H, J=3.6 Hz), 5.27 (d, 1H, J=3.6 Hz), 4.80 (1H, overlapped with H$_2$O), 4.45 (d, 1H, J=7.8 Hz), 3.99 (ddd, 1H, J=11.4 Hz, 5.4 Hz, 5.4 Hz), 3.88-3.74 (m, 6H), 3.71-3.51 (m, 17H), 3.50-3.41 (m, 6H), 3.38 (dd, 1H, J=8.4 Hz, 8.4 Hz). $^{13}$C NMR: (125 MHz, D$_2$O) δ 175.6, 175.5, 102.5, 102.2, 98.8, 98.5, 82.1, 81.2, 80.9, 76.0, 75.5, 73.0, 72.4, 72.3, 72.2, 71.9, 71.6, 71.3, 71.1, 69.3, 68.5, 68.0, 61.4, 61.1, 50.5.

Example 36

(2-azidoethyl) 4-O-benzoyl-α-D-xylopyranosyl-(1→3)-2,4-di-O-benzoyl-β-D-glucuronopyranosyl-(1→3)-4-O-benzoyl-α-D-xylopyranosyl-(1→3)-2,4-di-O-benzoyl-β-D-glucuronopyranosyl-(1→3)-4-0-benzoyl-α-D-xylopyranosyl-(1→3)-2,4-di-O-benzoyl-β-D-glucuronopyranoside methyl tri-ester (7-71)

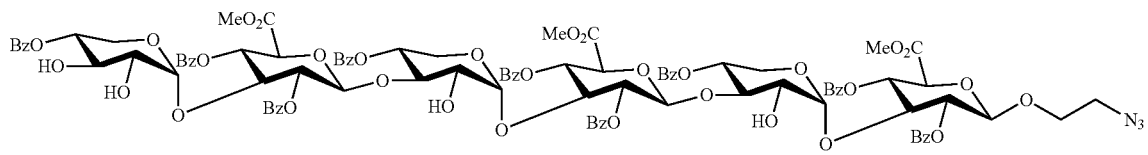

(2-azidoethyl) 4-O-benzoyl-α-D-xylopyranosyl-(1→3)-2,4-di-O-benzoyl-β-D-glucuronopyranosyl-(1→3)-4-O-benzoyl-α-D-xylopyranosyl-(1→3)-2,4-di-O-benzoyl-β-D-glucuronopyranosyl-(1→3)-4-O-benzoyl-α-D-xylopyranosyl-(1→3)-2,4-di-O-benzoyl-β-D-glucuronopyranoside methyl tri-ester (7-71): Trichloroacetimidate disaccharide donor 7-67 (0.11 g, 0.133 mmol) and tetrasaccharide acceptor 7-69 (0.12 g, 0.088 mmol) were mixed together, co-evaporated with toluene twice, and then dissolved in dry DCM (2.5 mL). The mixture was cooled in an ice-bath and a solution of TMSOTf (3 µL, 0.014 mmol) in dry DCM (0.1 mL) was added dropwise and then the mixture was warmed at room temperature. After 2 h the TLC showed complete consumption of donor (acceptor wasn't fully consumed). The reaction mixture was diluted with MeOH (2 mL) and Dowex H+ resin (0.1 g), further stirred for 8 h at room temperature. Thereupon, the mixture was filtered and solvent was evaporated before purification by flash chromatography to obtain tetrasaccharide 7-71 in 32% yield (71% brsm) yield. $^1$H NMR: (700 MHz, CDCl$_3$) δ 8.00-7.74 (m, 17H), 7.60-7.37 (m, 22H), 7.22 (t, 2H, J=7.7 Hz), 7.08 (t, 2H, J=7.7 Hz), 6.99 (t, 2H, J=7.7 Hz), 5.65 (dd, 1H, J=8.4 Hz, 8.4 Hz), 5.51 (dd, 1H, J=9.8 Hz, 9.8 Hz), 5.49 (dd, 1H, J=9.8 Hz, 9.8 Hz), 5.33 (dd, 1H, J=7.7 Hz, 7.7 Hz), 5.23 (dd, 1H, J=8.4 Hz, 8.4 Hz), 5.21 (dd, 1H, J=9.1 Hz, 9.1 Hz), 5.01 (d, 1H, J=8.4 Hz), 5.00 (d, 1H, J=8.4 Hz), 4.94 (d, 1H, J=4.2 Hz), 4.85 (d, 1H, J=4.2 Hz), 4.83 (d, 1H, J=7 Hz), 4.81 (d, 1H, J=3.5 Hz), 4.75 (ddd, 2H, J=9.8 Hz, 9.8 Hz, 5.6 Hz), 4.68 (ddd, 1H, J=9.8 Hz, 9.8 Hz, 5.6 Hz), 4.62 (ddd, 1H, J=9.8 Hz, 9.8 Hz, 5.6 Hz), 4.27 (d, 1H, J=9.1 Hz), 4.25 (dd, 1H, J=8.4 Hz, 8.4 Hz), 4.21 (dd, 1H, J=8.4 Hz, 8.4 Hz), 4.17 (dd, 1H, J=9.1 Hz, 9.1 Hz), 4.13 (d, 1H, J=9.8 Hz), 4.12 (dd, 1H, J=7 Hz, 7 Hz), 4.08 (ddd, 1H, J=11.2 Hz, 5.6 Hz, 5.6 Hz), 3.92 (dd, 1H, J=9.1 Hz, 9.1 Hz), 3.85 (dd, 1H, J=9.1 Hz, 9.1 Hz), 3.75 (dd, 1H, J=9.8 Hz, 9.8 Hz), 3.71-3.67 (m, 2H), 168 (s, 3H), 3.53 (s, 3H), 3.49 (s, 3H), 3.47 (dd, 2H, J=11.2 Hz, 5.6 Hz), 3.43-3.39 (m, 2H), 3.38-3.28 (m, 9H), 3.24 (dd, 1H, J=9.1 Hz, 4.9 Hz), 3.23-3.20 (m, 2H), 3.19 (dd, 1H, J=9.1 Hz, 4.2 Hz), 2.41 (bs, 1H), 1.92 (d, 1H, J=7.7 Hz), 1.90 (d, 1H, J=7.7 Hz), 1.83 (d, 1H, J=9.1 Hz). $^{13}$C NMR: (150 MHz, CDCl$_3$) δ 167.5, 167.2, 166.0, 165.6, 165.5, 165.4, 165.3, 165.2(2), 133.7, 133.6, 133.5, 133.4, 133.2, 133.0(2), 130.0, 129.8, 129.7, 129.5(2), 129.4, 129.3(2), 129.2, 129.1, 129.0, 128.9, 128.6(2), 128.3(2), 128.2(2), 101.4, 100.8, 100.0, 99.8, 99.7, 79.1, 79.0, 78.9, 78.4, 78.1, 72.6, 72.5, 72.3, 72.2, 72.1, 71.9, 71.8, 71.7, 71.1, 70.9, 69.4, 69.3, 68.5, 59.4, 59.2, 52.9, 52.6, 52.5, 50.6.

Example 37

(2-azidoethyl) D-xylopyranosyl-α-(1→3)-β-D-glucuronopyranosyl-(1→3)-D-xylopyranosyl-α-(1→3)-β-D-glucuronopyranosyl-(1→3)-D-xylopyranosyl-α-(1→3)-β-D-glucuronopyranoside (7-72)

(2-azidoethyl) D-xylopyranosyl-α-(1→3)-β-D-glucuronopyranosyl-(1→3)-D-xylopyranosyl-α-(1→3)-β-D-glucuronopyranosyl-(1→3)-D-xylopyranosyl-α-(1→3)-β-D-glucuronopyranoside (7-72): To a solution of 7-71 (0.03 g, 0.015 mmol) in MeOH (12 mL) was added 4 N NaOH (0.15 mL) aqueous solution at 0° C. The mixture was stirred at room temperature for 48 h and then neutralized with 1 M HCl. The solvent was lyophilized and crude residue was purified by P-2 biogel affinity column with water as eluent to obtain 7-72 as a white foamy solid in 58% yield, $^1$H NMR: (600 MHz, D$_2$O) δ 5.26 (d, 1H, J=3.6 Hz), 5.24 (d, 1H, J=4.2 Hz), 5.22 (d, 1H, J=3.0 Hz), 4.67 (2 β-H's, overlapped with H$_2$O), 4.42 (d, 1H, J=7.8 Hz), 4.00 (ddd, 2H, J=11.4 Hz, 5.4 Hz, 5.4 Hz), 3.88-3.71 (m, 8H), 3.69-3.50 (m, 24H), 3.49-3.34 (m, 7H), 3.33 (dd, 1H, J=9 Hz, 9 Hz). $^{13}$C NMR: (125 MHz, D$_2$O) δ 175.7, 175.6, 175.5, 102.6, 102.5, 102.2, 98.8, 98.6, 98.5, 82.1, 81.2, 81.0, 80.8, 75.5, 73.0, 72.3, 71.9, 71.8, 71.7, 71.6, 71.3, 71.0, 69.3, 68.5, 68.0, 61.4, 61.2, 50.5.

Synthesis of B4GAT1-Glycan Trisaccharide

Example 38

(2-azidoethyl) 2,3-isopropylidene-β-D-xylopyranoside (8-15)

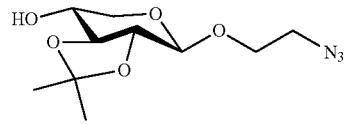

(2-azidoethyl) 2,3-isopropylidene-β-D-xylopyrattoside (8-15): Per-acetate xylose 7-13 (3.5 g, 10.99 mmol) and 2-azidoethanol (7-31) were dissolved together in dry DCM (20 mL) and the mixture was cooled in an ice-bath. BF$_3$·Et$_2$O (2.7 mL, 21.8 mmol) was added dropwise and the mixture was warmed at room temperature followed by stirring for 16 h. Thereupon, the mixture was diluted with DCM, quenched with trimethylamine, organic layer was washed with saturated NaHCO$_3$ solution, brine, and dried over Na$_2$SO$_4$. After filtering, the solvent was evaporated and crude 8-11 was directly taken in 20 mL of MeOH. NaOMe (0.2 g, 3.6 mmol) was added and the reaction was stirred for 6 h at 40° C. Solvent was evaporated and crude residue was purified by flash chromatography to obtain 8-12 in 78% yield. Compound 8-15 was synthesized from 8-12 by fol-

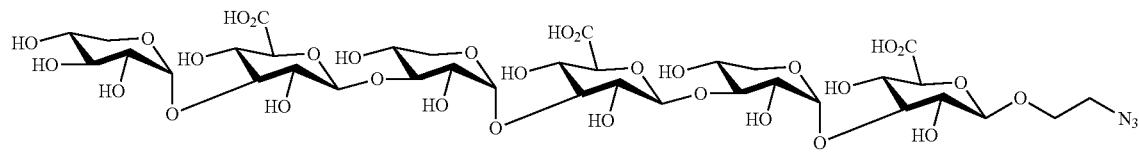

lowing methods described in *Eur. J. Med. Chem.* 2013, 64, 1-15. $^1$H NMR: (400 MHz, CDCl$_3$) δ 4.67 (d, 1H, J=7.6 Hz), 4.06-4.02 (m, 1H), 3.99 (ddd, 1H, J=8.4 Hz, 6 Hz, 4.4 Hz), 3.55 (dd, 1H, J=9.2 Hz, 9.2 Hz), 3.50-3.44 (m, 3H), 3.37 (dd, 1H, J=9.6 Hz, 7.6 Hz), 3.29 (dd, 1H, J=11.2 Hz, 3.6 Hz), 2.03 (d, 1H, J=8.4 Hz), 1.46 (s, 3H), 1.45 (s, 3H). $^{13}$C NMR: (100 MHz, CDCl$_3$) δ 111.6, 101.8, 80.8, 77.4, 76.4, 69.0, 67.6, 50.7, 26.8, 26.5.

Example 39

(2-azidoethyl) 2,3-di-O-benzyl-β-D-xylopyranoside (8-21)

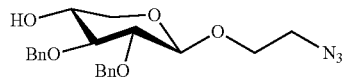

(2-azidoethyl) 2,3-di-O-benzyl-β-D-xylopyranoside (8-21): To a solution of 8-15 (1.96 g, 7.59 mmol) in dry DCM (20 mL) were added trimethylamine (2 mL, 15.18 mmol) and DMAP (0.47 g, 3.8 mmol). The mixture was cooled in an ice-bath and benzoyl chloride (1.3 mL, 11.39 mmol) was added dropwise. The mixture was warmed at room temperature and stirred for additional 6 h. The solution was then diluted with DCM, poured into ice-water, extracted with DCM (50×3 mL). Combined organic layer was washed with 1 M HCl, brine, dried over Na$_2$SO$_4$, filtered, and evaporated. The crude 8-18 was dissolved in 25 mL of DCM/MeOH (1:1 v/v) mixture and was treated with p-toluenesulfonic acid (0.72 g, 3.8 mmol) at room temperature for 2 h. Reaction mixture was quenched trimethylamine and solvent was evaporated. After flash chromatographic purification, 8-19 was obtained in 92% overall yield (2.25 g).

Compound 8-19 (1.4 g, 4.33 mmol) in dry DMF was treated with NaH (0.7 g, 17.32 mmol, 60 wt %) at 0° C. for 30 min. Then benzyl bromide (1.5 mL, 12.99 mmol) was added dropwise and the reaction mixture was warmed at room temperature followed by additional stirring for 12 h. The mixture was then quenched with crushed ice, diluted with water, and extracted with ether (50×3 mL), Combined organic layer was washed with water, brine, and dried over Na$_2$SO$_4$. After filtration, solvent was evaporated and crude was taken in dry MeOH (30 mL) and NaOMe (0.048 g, 0.866 mmol) was added to it. The reaction mixture was stirred for 12 h at 40° C. Solvent was evaporated and crude residue was purified by flash chromatography to obtain 8-21 in 81% yield. $^1$H NMR: (400 MHz, CDCl$_3$) δ 7.37-7.28 (m, 10H), 4.94 (d, 1H, J=11.2 Hz), 4.75 (d, 1H, J=12 Hz), 4.70 (d, 1H, J=11.2 Hz), 4.63 (d, 1H, J=11.6 Hz), 4.37 (d, 1H, J=7.6 Hz), 4.00 (ddd, 1H, J=10.4 Hz, 6 Hz, 4 Hz), 3.93 (dd, 1H, J=11.6 Hz, 5.2 Hz), 3.71-3.65 (m, 2H), 3.52 (ddd, 1H, 3=9.6 Hz, 9.6 Hz, 5.2 Hz), 3.45-3.41 (m, 2H), 3.26 (dd, 1H, J=9.2 Hz, 7.2 Hz), 3.22 (dd, 1H, J=9.6 Hz, 8.8 Hz). $^{13}$C NMR: (100 MHz, CDCl$_3$) δ 138.3, 138.1, 128.5(2), 128.0, 127.9, 127.8(2), 103.6, 81.0, 76.9, 75.5, 74.4, 73.1, 67.9, 63.8, 50.9.

Example 40

Trichloroacetimido 3,4-di-O-benzyl-2-O-benzoyl-α-D-xylopyranosyl-(1→3)-2,4-di-O-benzoyl-α-D-glucuronopyranoside methyl ester (8-17)

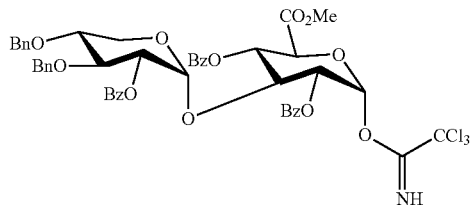

Trichloroacetimido 3,4-di-O-benzyl-2-O-benzoyl-α-D-xylopyranosyl-(1→3)-2,4-di-O-benzoyl-α-D-glucuronopyranoside methyl ester (8-17): To a solution of 7-63 (1.5 g, 1.77 mmol) in dry DCM (20 mL) were added trimethylamine (0.5 mL, 3.54 mmol) and DMAP (0.108 g, 0.89 mmol), The mixture was cooled in an ice-bath and benzoyl chloride (0.3 mL, 2.66 mmol) was added dropwise. The mixture was warmed at room temperature and stirred for additional 48 h. The solution was then diluted with DCM, poured into ice-water, extracted with DCM (50×3 mL). Combined organic layer was washed with 1 M HCl, brine, dried over Na$_2$SO$_4$, filtered, and evaporated. Crude residue was purified by flash chromatography to obtain 8-23. (Incomplete consumption of SM Recovered SM was subjected to another round of benzoylation and the product was combined to obtain 87% yield).

Compound 8-23 (1 g, 0.35 mmol) was dissolved in a mixture of MeOH/THF (3:7/v, 40 mL) and then cooled in an ice-bath. NH$_3$-gas was bubbled into the mixture for 30 min and then the pale-yellow solution was left to stir for additional 7 h while attaining the room temperature. Air was bubbled to remove excess ammonia and solvent was removed under reduced pressure. The crude residue was then dissolved in dry DCM (35 mL) followed by addition of DBU (0.078 g, 0.51 mmol) and CCl$_3$CN (0.51 mL, 5.13 mmol). After stirring at room temperature for 1 h, the solvent was evaporated and crude was purified by flash chromatography to obtain 8-17 in 64% yield over 2 steps. $^1$H NMR: (400 MHz, CDCl$_3$) δ 8.60 (s, 1H), 8.10-8.07 (m, 2H), 7.64-7.28 (m, 12H), 7.24-9.95 (m, 11H), 6.84 (d, 1H, J=4 Hz), 5.56 (dd, 1H, J=10 Hz, 9.6 Hz), 5.53 (dd, 1H, J=8.4 Hz, 4 Hz), 5.34 (d, 1H, J=3.6 Hz), 4.95 (dd, 1H, J=10.4 Hz, 4 Hz), 4.67 (dd, 1H, 3=9.6 Hz, 9.6 Hz), 4.66 (d, 1H, J=11.2 Hz), 4.53 (d, 1H, J-=11.6 Hz), 4.51 (d, 1H, J=10.4 Hz), 4.42 (d, 1H, J=11.6 Hz), 4.23 (d, 1H, J=11.6 Hz), 3.84 (dd, 1H, J=10 Hz, 8.8 Hz), 3.54 (dd, 1H, J=10.4 Hz, 6.8 Hz), 3.51 (s, 3H), 3.49-3.43 (m, 1H), 3.32 (dd, 1H, J=10 Hz, 4.8 Hz). $^{13}$C NMR: (100 MHz, CDCl$_3$) δ 167.3, 165.3, 165.2, 164.7, 160.1, 138.0, 137.9, 133.6, 133.3, 132.9, 130.0, 129.7, 129.5, 128.8(2), 128.4, 128.3, 128.2, 128.0, 127.8, 127.6, 127.5, 127.4, 98.2, 92.8, 90.5, 78.6, 77.7, 77.2, 75.3, 74.4, 72.8, 72.3, 71.6, 70.6, 70.5, 60.9, 52.8.

Example 41

(2-azidoethyl) 3,4-di-O-benzyl-2-O-benzoyl-α-D-xylopyranosyl-(1→3)-2,4-di-O-benzoyl-β-D-glucurono-pyranosyl-(1→4)-2,3-di-O-benzyl-β-D-xylopyranosyl methyl ester (8-25)

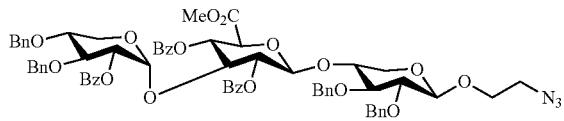

(2-azidoethyl) 3,4-di-O-benzyl-2-O-benzoyl-α-D-xylopyranosyl-(1→3)-2,4-di-O-benzoyl-β-D-glucurono-pyranosyl-(1→4)-2,3-di-O-benzyl-β-D-xylopyranosyl methyl ester (8-25): Trichloroacetimidate donor 8-17 (0.16 g, 0,164 mmol) and xylose acceptor 8-21 (0.085 g, 0.213 mmol) were dissolved together in dry DCM (5 mL) and 4 Å molecular sieves (0.23 g) was added. The mixture was stirred for 45 min before cooling down in an ice-bath. A solution of TMSOTf (5 μL, 0.025 mmol) in dry DCM (0.05 mL) was added dropwise and then the warmed at room temperature. After 2 h, the reaction was quenched with a few drops of triethylamine, diluted with DCM, and filtered through Celite. Upon evaporation of solvent and flash chromatographic purification, trisaccharide 8-25 was obtained as a white solid in 63% yield. $^1$H NMR: (700 MHz, CDCl$_3$) δ 8.05-8.03 (m, 2H), 7.67-7.66 (m, 2H), 7.56-7.55 (m, 2H), 7.49-7.21 (m, 22H), 7.05-6.97 (m, 7H), 5.50 (dd, 1H, J=9.1 Hz, 9.1 Hz), 5.29 (d, 1H, J=7.7 Hz), 5.27 (d, 1H, J=3.5 Hz), 5.01 (d, 1H, J=11.9 Hz), 4.88 (dd, 1H, J=10.5 Hz, 4.2 Hz), 4.72 (d, 1H, J=11.2 Hz), 4.66 (d, 1H, J=11.9 Hz), 4.65 (d, 1H, J=10.5 Hz), 4.53 (d, 1H, J=11.2 Hz), 4.43 (d, 1H, J=11.2 Hz), 4.40 (d, 1H, J=11.2 Hz), 4.26 (d, 1H, J=7 Hz), 4.23 (d, 1H, J=11.9 Hz), 3.96 (dd, 1H, J=8.4 Hz, 8.4 Hz), 3.91 (d, 1H, J=9.1 Hz), 3.86-3.82 (m, 2H), 3.61-3.58 (m, 1H), 3.52-3.50 (m, 1H), 3.46 (s, 3H), 3.45-3.41 (m, 1H), 3.23-3.21 (m, 5H). $^{13}$C NMR: (150 MHz, CDCl$_3$) δ 167.3, 165.4, 165.0, 164.6, 138.7, 138.5, 138.0(2), 133.2(2), 132.9, 129.8 (2), 129.6, 129.4, 128.9, 128.4(3), 128.3(2), 128.2(2), 128.1, 128.0(2), 127.8, 127.6(2), 127.5, 127.4, 127.2, 103.6, 100.4, 97.9, 82.2, 80.9, 78.5, 77.7, 77.5, 75.4(2), 74.2, 73.7, 72.6 (2), 72.5, 72.4, 67.7, 64.0, 60.8, 52.6, 50.8.

Example 42

(2-azidoethyl) 2-O-benzoyl-α-D-xylopyranosyl-(1→3)-2,4-di-O-benzoyl-β-D-glucuronopyranosyl-(1→4)-β-D-xylopyranoside methyl ester (8-26)

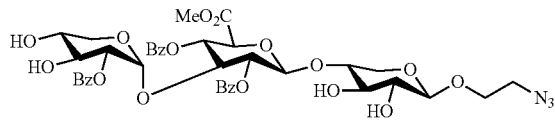

(2-azidoethyl) 2-O-benzoyl-α-D-xylopyranosyl-(1→3)-2,4-di-O-benzoyl-β-D-glucuronopyranosyl-(1-34)-β-D-xylopyranoside methyl ester (8-26): To a solution of 8-25 (0.051 g, 0,042 mmol) in EtOAc (0.56 mL) was added a solution of NaBrO$_3$ (0.057 g, 0.378 mmol in 0.42 mL water). Then a solution of Na$_2$S$_2$O$_4$ (0.059 g, 0.336 mmol in 0.5 mL water) was added dropwise over 5 min while the mixture was stirred vigorously for additional 3.5 h at room temperature. The mixture was then diluted with 3 mL of EtOAc, quenched with 10% Na$_2$S$_2$O$_3$ solution (1 mL), and extracted with EtOAc (5×3 mL), Combined organic layer was dried over MgSO$_4$, filtered, and solvent was evaporated, Flash chromatography yielded 8-26 as a white solid (93% yield). $^1$H NMR: (600 MHz, CDCl$_3$) δ 8.10-8.07 (m, 2H), 7.73-7.72 (m, 2H), 7.60-7.24 (m, 11H), 5.52 (dd, 1H, J=9.6 Hz, 9.6 Hz), 5.42 (dd, 1H, J=7.8 Hz, 7.8 Hz), 5.35 (d, 1H, J=4.2 Hz), 4.99 (d, 1H, J=7.8 Hz), 4.84 (dd, 1H, J=10.2 Hz, 3.6 Hz), 4.43 (dd, 1H, J=9 Hz, 9 Hz), 4.13 (t, 2H, J=7.2 Hz), 4.01 (dd, 1H, J=12 Hz, 6 Hz), 3.96 (dd, 1H, J=8.4 Hz, 8.4 Hz), 3.6 Hz), 3.73 (ddd, 1H, J=9.6 Hz, 4 Hz, 1.6 Hz), 3.65-3.62 (m, 2H), 3.58-3.54 (m, 2H), 3.47-3.44 (m, 2H), 3.43 (s, 3H), 3.42-3.38 (m, 2H), 3.28-3.25 (m, 2H), 3.18 (dd, 11-1, J=11.4 Hz, 11.4 Hz). $^{13}$C NMR: (150 MHz, CDCl$_3$) δ 167.6, 165.9, 165.8, 165.6, 164.8, 133.6, 133.3, 133.1, 130.1, 129.9, 129.8, 129.4, 129.3, 129.2, 128.6(2), 128.4, 128.3, 128.2, 128.1, 103.5, 101.6, 98.2, 87.2, 77.3, 72.9, 72.7, 72.5, 71.8(2), 70.2, 68.6, 68.1, 65.4, 62.0, 52.9, 50.7.

Example 43

(2-azidoethyl) D-xylopyranosyl-α-(1→3)-β-D-glucuronopyranosyl-(1→4)43-n-xylopyranoside (8-27)

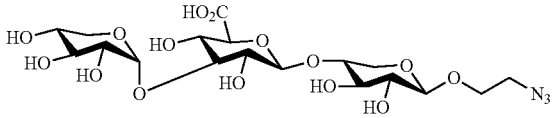

(2-azidoethyl) D-xylopyranosyl-α-(1→3)β-D-glucuronopyranosyl-(1→4)-β-D-xylopyranoside (8-27): To a solution of 8-26 (0.025 g, 0.03 mmol) in MeOH (15 mL) was added 4 N NaOH (0.2 mL) aqueous solution at 0° C. The mixture was stirred at room temperature for 24 h and then neutralized with 1 M HCl. The solvent was lyophilized and crude residue was purified by P-2 biogel affinity column with water as eluent to obtain 8-27 as a white foamy solid in 71% yield. $^1$H NMR: (600 MHz, D$_2$O) δ 5.32 (d, 1H, J=3.6 Hz), 4.77 (d, 1H, J=8.4 Hz), 4.48 (d, 1H, J=7.8 Hz), 4.00 (dd, 1H, J=12 Hz, 4.8 Hz), 3.89 (dd, 1H, J=10.8 Hz, 10.8 Hz), 3.83 (ddd, 1H, J=11.4 Hz, 6 Hz, 4.2 Hz), 336-330 (m, 3H), 3.69-3.57 (m, 7H), 3.53-3.49 (m, 3H), 3.48-3.46 (m, 2H), 3.34 (dd, 1H, J=10.2 Hz, 10.2 Hz). $^{13}$C NMR: (150 MHz, CDCl$_3$) δ 175.5, 102.7, 102.5, 98.8, 84.0, 812, 75.6, 72.9, 72.5, 72.2, 71.6, 69.3, 68.5, 67.8, 64.6, 61.4, 50.4.

It should be understood that while this disclosure has been described herein in terms of specific, preferred embodiments set forth in detail, such embodiments are presented by way of illustration of the general principles of the disclosure, and the disclosure is not necessarily limited thereto. Certain modifications and variations in any given material, process step or chemical formula will be readily apparent to those skilled in the art without departing from the true spirit and scope of the present disclosure, and all such modifications and variations should be considered within the scope of the claims that follow.

REFERENCES 1. (a) Ervasti, J. M.; Ohlendieck, K.; Kahl, S. D.; Gayer, M. G.; Campbell, K. P., *Nature* 1990, 345 (6273), 315-319; (b) Barresi, R.; Campbell, K. P., *Journal of Cell Science* 2006, 119 (2), 199-207.

2. Durbeej, M.; Henry, M. D.; Campbell, K. P., *Current Opinion in Cell Biology* 1998, 10 (5), 594-601.
3. Ervasti, J. M.; Campbell, K. P., *Cell* 1991, 66 (6), 1121-1131.
4. (a) Ibraghimov-Beskrovnaya, O.; Ervasti, J. M.; Leveille, C. J.; Slaughter, C. A.; Sennett, S. W.; Campbell, K. P., *Nature* 1992, 355 (6362), 696-702; (b) Holt, K. H.; Crosbie, R. H.; Venzke, D. P.; Campbell, K. P., *FEBS Letters* 2000, 468 (1), 79-83.
5. Cao, W.; Henry, M. D.; Borrow, P.; Yamada, H.; Elder, J. H.; Ravkov, E. V.; Nichol, S. T.; Compans, R. W.; Campbell, K. P.; Oldstone, M. B. A., *Science* 1998, 282 (5396), 2079-2081.
6. (a) Ervasti, J.; Campbell, K., *The Journal of Cell Biology* 1993, 122 (4), 809-823; (b) Hohenester, E.; Tisi, D.; Talts, J. F.; Timpl, R., *Molecular Cell* 1999, 4 (5), 783-792.
7. Campbell, K. P., *Cell* 1995, 80 (5), 675-679.
8. Singh, J.; Itahana, Y.; Knight-Krajewski, S.; Kanagawa, M.; Campbell, K. P.; Bissell, M. J.; Muschler, J., *Cancer Research* 2004, 64 (17), 6152-6159.
9. Yoshida-Moriguchi, T.; Willer, T.; Anderson, M. E.; Venzke, D.; Whyte, T.; Muntoni, F.; Lee, H.; Nelson, S. F.; Yu, L.; Campbell, K. P., *Science* 2013, 341 (6148), 896-899.
10. (a) Inamori, K.-i.; Yoshida-Moriguchi, T.; Hara, Y.; Anderson, M. E.; Yu, L.; Campbell, K. P., *Science* 2012, 335 (6064), 93-96; (b) Praissman, J. L.; Live, D. H.; Wang, S.; Ramiah, A.; Chinoy, Z. S.; Boons, G.-J.; Moremen, K. W.; Wells, L., *eLife* 2014, 3, e03943.
11. Coutinho, P. M.; Deleury, E.; Davies, G. J.; Henrissat, B., *Journal of Molecular Biology* 2003, 328 (2), 307-317.
12. (a) Gagneux, P.; Varki, A., *Glycobiology* 1999, 9 (8), 747-755; (b) Lewis, A. L.; Desa, N.; Hansen, E. E.; Knirel, Y. A.; Gordon, J. I.; Gagneux, P.; Nizet, V.; Varki, A., *Proceedings of the National Academy of Sciences* 2009, 106 (32), 13552-13557.
13. Werz, D. B.; Ranzinger, R.; Herget, S.; Adibekian, A.; von der Lieth, C.-W.; Seeberger, P. H., *ACS Chemical Biology* 2007, 2 (10), 685-691.
14. van Kuik, J. A.; van Halbeek, H.; Kamerling, J. P.; Vliegenthart, 3. F., *Journal of Biological Chemistry* 1985, 260 (26), 13984-13988.
15. Oscarson, S.; Svahnberg, P., *Journal of the Chemical Society, Perkin Transactions* 1 2001, (8), 873-879.
16. (a) Wang, Z.; Chinoy, Z. S.; Ambre, S. G.; Peng, W.; McBride, R.; de Vries, R. P.; Glushka, J.; Paulson, J. C.; Boons, G.-J., *Science* 2013, 341 (6144), 379-383; (b) Ragupathi, G.; Koide, F.; Livingston, P. O.; Cho, Y. S.; Endo, A.; Wan, Q.; Spassova, M. K.; Keding, S. J.; Allen, J.; Ouerfelli, O.; Wilson, R. M.; Danishefsky, S. J., *Journal of the American Chemical Society* 2006, 128 (8), 2715-2725.
17. (a) Kuraya, N.; Kuraya, N.; Omichi, K.; Omichi, K.; Nishimura, H.; Nishimura, H.; Iwanaga, S.; Iwanaga, S.; Hase, S.; Hase, S., *Journal of Biochemistry* 1993, 114 (6), 763-765; (b) Kitamura, M.; Hojo, H.; Nakahara, Y.; Ishimizu, T.; Hase, S., *Glycoconjugate Journal* 2004, 21 (5), 197-203.
18. (a) Ishiwata, A.; Lee, Y. J.; Ito, Y., *Organic & Biomolecular Chemistry* 2010, 8 (16), 3596-3608; (b) Yasomanee, J. P.; Demchenko, A. V., *Journal of the American Chemical Society* 2012, 134 (49), 20097-20102.
19. Tvaroŝka, I.; Bleha, T., Anomeric and Exo-Anomeric Effects in Carbohydrate Chemistry. In *Advances in Carbohydrate Chemistry and Biochemistry*, Tipson, R. S.; Derek, H., Eds. Academic Press: 1989; Vol. Volume 47, pp 45-123.
20. Werz, D. B.; Castagner, B.; Seeberger, P. H., *Journal of the American Chemical Society* 2007, 129 (10), 2770-2771.
21. Kim, J.-H.; Yang, H.; Boons, G.-J., *Angewandte Chemie International Edition* 2005, 44 (6), 947-949.
22. Lu, S.-R.; Lai, Y.-H.; Chen, J.-H.; Liu, C.-Y.; Mong, K.-K. T., *Angewandte Chemie International Edition* 2011, 50 (32), 7315-7320.
23. Komarova, B. S.; Orekhova, M. V.; Tsvetkov, Y. E.; Nifantiev, N. E., *Carbohydrate Research* 2014, 384, 70-86,
24. Barresi, F.; Hindsgaul, O., *Journal of the American Chemical Society* 1991, 113 (24), 9376-9377.
25. (a) Stork, G.; Suh, H. S.; Kim, G., *Journal of the American Chemical Society* 1991, 113 (18), 7054-7056; (b) Stork, G.; Kim, G., *Journal of the American Chemical Society* 1992, 114 (3), 1087-1088.
26. Fairbanks, A., *Synlett* 2003, 2003 (13), 1945-1958.
27. Ito, Y.; Ogawa, T., *Angewandte Chemie International Edition* in English 1994, 33 (17), 1765-1767.
28. Ishiwata, A.; Munemura, Y.; Ito, Y., *European Journal of Organic Chemistry* 2008, 2008 (25), 4250-4263.
29. (a) Amatore, C.; Jutand, A.; Mallet, J.-M.; Meyer, G.; Sinay, P., *Journal of the Chemical Society, Chemical Communications* 1990, (9), 718-719; (b) Alberto Marra*, J.-M. M., Christian Amatore, Pierre Sinaÿ, *Synlett* 1990, 10, 572-574; (c) Amatore, C.; Jutand, A.; Meyer, G.; Bourhis, P.; Machetto, F.; Mallet, J.-M.; Sinaÿ, P.; Tabeur, C.; Zhang, Y.-M., *Journal of Applied Electrochemistry* 1994, 24 (8), 725-729.
30. van den Bos, L. J.; Codée, J. D. C.; van der Toorn, J. C.; Boltje, T. J.; van Boom, J. H.; Overkleeft, H. S.; van der Marel, G. A., *Organic Letters* 2004, 6 (13), 2165-2168.
31. Li, K.; Helm, R. F., *Carbohydrate Research* 1995, 273 (2), 249-253.
32. (a) Haller, M.; Boons, G.-J., *Journal of the Chemical Society, Perkin Transactions* 1 2001, (8), 814-822; (b) Lefeber, D. J.; Arevalo, E. A.; Kamerling, J. P.; Vliegenthart, J. F. G., *Canadian Journal of Chemistry* 2002, 80 (1), 76-81; (c) Huang, L.; Teumelsan, N.; Huang, X., *Chemistry* 2006, 12 (20), 5246-52; (d) Huang, L.; Huang, X., *Chemistry—A European Journal* 2007, 13 (2), 529-540; (e) Iynkkaran, I.; Bundle, D. R., *Carbohydrate Research* 2013, 378, 26-34.
33. Barbier, M.; Breton, T.; Servat, K.; Grand, E.; Kokoh, B.; Kovensky, J., *Journal of Carbohydrate Chemistry* 2006, 25 (2-3), 253-266.
34. (a) Kato, Y.; Matsuo, R.; Isogai, A., *Carbohydrate Polymers* 2003, 51 (1), 69-75; (b) Isogai, A.; Kato, Y., *Cellulose* 1998, 5 (3), 153-164.
35. Shibuya, M.; Tomizawa, M.; Sasano, Y.; Iwabuchi, Y., *The Journal of Organic Chemistry* 2009, 74 (12), 4619-4622.

36. Schmidt, R. R.; Stumpp, M.; Michel, J., *Tetrahedron Letters* 1982, 23 (4), 405-408.
37. (a) Stachulski, A. V.; Harding, J. R.; Lindon, J. C.; Maggs, J. L.; Park, B. K.; Wilson, I. D., *Journal of Medicinal Chemistry* 2006, 49 (24), 6931-6945; (b) Shipkova, M.; Wieland, E., *Clinica Chimica Acta* 2005, 358 (1-2), 2-23.
38. (a) Wadouachi, A.; Kovensky, J., *Molecules* 2011, 16 (12), 3933-3968; (b) Dhamale, O. P.; Zong, C.; Al-Mafraji, K.; Boons, G. J., *Org Biomol Chem* 2014, 12 (13), 2087-98; (c) Adibekian, A.; Bindschadler, P.; Timmer, M. S.; Noti, C.; Schutzenmeister, N.; Seeberger, P. H., *Chemistry* 2007, 13 (16), 4510-22; (d) Kovensky, J.; Duchaussoy, P.; Petitou, M.; Sinaÿ, P., *Tetrahedron: Asymmetry* 1996, 7 (11), 3119-3128.
39. Willer, T.; Inamori, K.-i.; Venzke, D.; Harvey, C.; Morgensen, G.; Hara, Y.; Beltran Valero de Bernabé D.; Yu, L.; Wright, K. M.; Campbell, K. P., *eLife* 2014, 3, e03941.
40. Sasaki, K.; Kurata-Miura, K.; Ujita, M.; Angata, K.; Nakagawa, S.; Sekine, S.; Nishi, T.; Fukuda, M., *Proceedings of the National Academy of Sciences* 1997, 94 (26), 14294-14299.
41. Praissman, J. L.; Willer, T.; Sheikh, M. O.; Toi, A.; Chitayat, D.; Lin, Y.-Y.; Lee, H.; Stalnaker, S. H.; Wang, S.; Prabhakar, P. K.; Nelson, S. F.; Stemple, D. L.; Moore, S. A.; Moremen, K. W.; Campbell, K. P.; Wells, L., *eLife* 2016, 5, e14473.
42. (a) Adinolfi, M.; Barone, G.; Guariniello, L.; Iadonisi, A., *Tetrahedron Letters* 1999, 40 (48), 8439-8441; (b) Niemietz, M.; Perkams, L.; Hoffman, J.; Eller, S.; Unverzagt, C., *Chemical Communications* 2011, 47 (37), 10485-10487.

What is claimed is:

1. A method for preparing a synthetic dystroglycan oligosaccharide comprising:

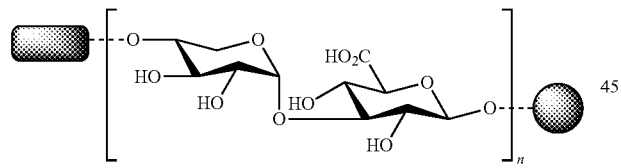

with a repeating disaccharide motif consists of Glucuronic Acid (GlcA) and Xylose (Xyl) having a defined glycosyl connection GlcA-β-(1→4)-Xyl-α-(1→3)-GlcA, comprising:

using a redox mediated one-pot intramolecular aglycon delivery (IAD) reaction comprising activating xylose thioglycoside with 2,3-Dichloro-5,6-dicyano-β-benzoquinone (DDQ) to produce a mixed acetal;

reacting the mixed acetal with tris-(4-bromophenyl) ammoniumyl hexachloroantimonate (BAHA), a single electron transfer reagent and 3-OH glucuronic acid acceptor to produce a 1,2-cis glycosylated product; and using a base mediated deprotection method to remove protecting groups from the 1,2-cis glycosylated product to produce the synthetic dystroglycan oligosaccharide.

2. A method for preparing a synthetic dystroglycan disaccharide having the structure:

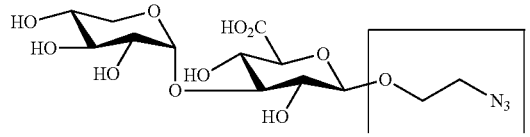

with a disaccharide motif consisting of Glucuronic Acid (GlcA) and Xylose (Xyl) having a defined glycosyl connection Xyl-α-(1→3)-GlcA, comprising:

employing a Schmidt's glycosylation reaction with protected disaccharide [Xyl-α-(1→3)-GlcA] trichloroacetimidate as a donor with a C-2 neighboring participating group on reducing end GlcA;

driving the Schmidt's glycosylation reaction using a 2-azidoethanol acceptor to produce a chemical modulation serving as a handle for further conjugation; and using a base mediated deprotection method to produce the synthetic dystroglycan oligosaccharide having the defined synthetic dystroglycan disaccharide.

3. A method for preparing a synthetic dystroglycan tetrasaccharide having the structure:

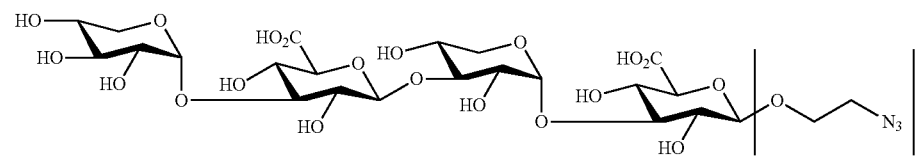

with a tetrasaccharide motif consisting of a repeating disaccharide motif consisting of Glucuronic Acid (GlcA) and Xylose (Xyl) having a defined glycosyl connection Xyl-α-(1→3)-GlcA-β-(1→3)-Xyl-α-(1→3)-GlcA, comprising:
employing a Schmidt's glycosylation reaction with a protected disaccharide [Xyl-α-(1→3)-GlcA] trichloroacetimidate as a donor with a C-2 neighboring participating group on reducing end GlcA;
driving the Schmidt's glycosylation reaction using a protected 2-azidoethyl-2,3-di-hydroxy-Xyl-α-(1→3)-GlcA acceptor to produce a chemical modulation serving as a handle for further conjugation; and
using a base mediated deprotection method to produce the synthetic dystroglycan tetrasaccharide having the defined glycosyl connection Xyl-α-(1→3)-GlcA-β-(1→3)-Xyl-α-(1→3)-GlcA.

4. A method for preparing a synthetic dystroglycan hexasaccharide having the structure:

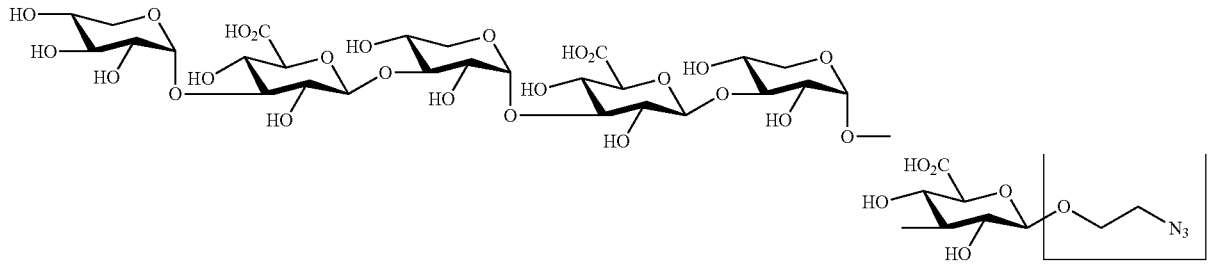

with a hexasaccharide motif consisting of a repeating disaccharide motif consisting of Glucuronic Acid (GlcA) and Xylose (Xyl) having a defined glycosyl connection Xyl-α-(1→3)-GlcA-β-(1→3)-Xyl-α-(1→3)-GlcA-β-(1→3)-Xyl-α-(1→3)-GlcA, comprising:
employing a Schmidt's glycosylation reaction with a protected tetrasaccharide [Xyl-α-(1→3)-GlcA-β-(1→3)-Xyl-α-(1→3)-GlcA] trichloroacetimidate as a donor with a C-2 neighboring participating group on reducing end GlcA;
driving the Schmidt's glycosylation reaction using a protected 2-azidoethyl-2,3-di-hydroxy-Xyl-α-(1→3)-GlcA acceptor to produce a chemical modulation serving as a handle for further conjugation; and
using a base mediated deprotection method to produce the synthetic dystroglycan hexasaccharide having the defined glycosyl connection Xyl-α-(1→3)-GlcA-β-(1→3)-Xyl-α-(1→3)-GlcA-β-(1→3)-Xyl-α-(1→3)-GlcA.

5. A method for preparing a synthetic dystroglycan trisaccharide having the structure:

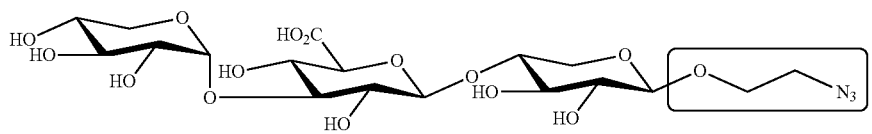

with a trisaccharide motif consisting of Glucuronic Acid (GlcA) and Xylose (Xyl) having a defined glycosyl connection Xyl-α-(1→3)-GlcA-β-(1→4)-Xyl, comprising:

employing a Schmidt's glycosylation reaction with a protected disaccharide [Xyl-α-(1→3)-GlcA] trichloroacetimidate as a donor with a C-2 neighboring participating group on the reducing end GlcA;

driving the Schmidt's glycosylation reaction using a protected 2-azidoethyl-4-hydroxy-Xyl acceptor to produce a chemical modulation serving as a handle for further conjugation; and using a oxidative debenzylation (sodium bromate+sodium dithionate) followed by the base mediated deprotection method to produce the synthetic dystroglycan trisaccharide having the defined glycosyl connection Xyl-α-(1→3)-GlcA-β-(1→4)-Xyl.

\* \* \* \* \*